(12) United States Patent
Zinzalla et al.

(10) Patent No.: US 11,952,418 B2
(45) Date of Patent: Apr. 9, 2024

(54) BIPARATOPIC POLYPEPTIDES ANTAGONIZING WNT SIGNALING IN TUMOR CELLS

(71) Applicant: Boehringer Ingelheim International GmbH, Ingelheim am Rhein (DE)

(72) Inventors: Vittoria Zinzalla, Vienna (AT); Klaus-Peter Kuenkele, Perchtoldsdorf (AT); Marie-Ange Buyse, Merelbeke (BE); Karen Cromie, Zwijnaarde (BE); Stephanie Staelens, Zwijnaarde (BE); Beatrijs Strubbe, Zwijnaarde (BE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 598 days.

(21) Appl. No.: 16/788,329

(22) Filed: Feb. 12, 2020

(65) Prior Publication Data

US 2020/0199222 A1 Jun. 25, 2020

Related U.S. Application Data

(63) Continuation of application No. 15/367,323, filed on Dec. 2, 2016, now Pat. No. 10,597,449.

(30) Foreign Application Priority Data

Dec. 4, 2015 (EP) ..................................... 15197999

(51) Int. Cl.
*A61K 39/00* (2006.01)
*C07K 16/18* (2006.01)
*C07K 16/28* (2006.01)

(52) U.S. Cl.
CPC .............. *C07K 16/28* (2013.01); *C07K 16/18* (2013.01); *A61K 2039/505* (2013.01); *A61K 2039/545* (2013.01); *C07K 2317/22* (2013.01); *C07K 2317/24* (2013.01); *C07K 2317/31* (2013.01); *C07K 2317/33* (2013.01); *C07K 2317/40* (2013.01); *C07K 2317/565* (2013.01); *C07K 2317/567* (2013.01); *C07K 2317/569* (2013.01); *C07K 2317/62* (2013.01); *C07K 2317/70* (2013.01); *C07K 2317/73* (2013.01); *C07K 2317/76* (2013.01); *C07K 2317/92* (2013.01); *C07K 2317/94* (2013.01); *C07K 2319/31* (2013.01)

(58) Field of Classification Search
CPC .................................................. A61K 2039/505
See application file for complete search history.

(56) References Cited

U.S. PATENT DOCUMENTS

| | | | |
|---|---|---|---|
| 10,597,449 B2 | 3/2020 | Zinzalla et al. | |
| 2010/0254980 A1 | 10/2010 | Cong et al. | |
| 2011/0119661 A1 | 5/2011 | Agrawal et al. | |
| 2011/0138391 A1 | 6/2011 | Cho et al. | |
| 2012/0276089 A1 | 11/2012 | Lee | |
| 2013/0058934 A1 | 3/2013 | Cong et al. | |
| 2014/0029752 A1 | 1/2014 | Kishi et al. | |

FOREIGN PATENT DOCUMENTS

| | | |
|---|---|---|
| WO | 9404678 A1 | 3/1994 |
| WO | 9634103 A1 | 10/1996 |
| WO | 0179286 A2 | 10/2001 |
| WO | 200179271 A1 | 10/2001 |
| WO | 2003002609 A2 | 1/2003 |
| WO | 03059934 A2 | 7/2003 |
| WO | 2004041867 A2 | 5/2004 |
| WO | 2006040153 A2 | 4/2006 |
| WO | 2006122786 A2 | 11/2006 |
| WO | 2006122787 A1 | 11/2006 |
| WO | 2007142298 | 12/2007 |
| WO | 2008020079 A1 | 2/2008 |
| WO | 2008028977 A2 | 3/2008 |
| WO | 2008040153 A1 | 4/2008 |
| WO | 2008068280 A1 | 6/2008 |
| WO | 2009056634 A2 | 5/2009 |
| WO | 2009109635 A2 | 9/2009 |
| WO | 2009127691 A1 | 10/2009 |
| WO | 2011075861 A1 | 6/2011 |
| WO | 2011095545 A1 | 8/2011 |
| WO | 2011119661 | 9/2011 |
| WO | 2011138391 | 11/2011 |
| WO | 2011138392 A1 | 11/2011 |
| WO | 2012175741 A2 | 12/2012 |
| WO | 2013024059 A2 | 2/2013 |
| WO | 2013067355 A1 | 5/2013 |
| WO | 2014029752 | 2/2014 |

OTHER PUBLICATIONS

Jackson et al. (Mol. Cancer Res. Sep. 2016; 14 (9): 859-68).*
Ettenberg et al. (Proc. Natl. Acad. Sci. USA. Aug. 31, 2010; 107 (35): 15473-8).*
International Search Report for PCT/EP2016/079575 dated Feb. 15, 2017.
Jahnichen, Sven et al. "CXCR4 nanobodies (VHH-based single variable domains) potently inhibit chemotaxis and HIV-1 replication and mobilize stem cells" PNAS, (2010) vol. 107, No. 47, pp. 20565-20570.
Joiner, Danese M. et al. "Lrp5 and Lrp6 in Development and Disease" (2013) Trends Endocrinology and Metabolism, vol. 24(1), pp. 31-39.

(Continued)

*Primary Examiner* — Stephen L Rawlings
(74) *Attorney, Agent, or Firm* — Wendy M. Gombert

(57) ABSTRACT

The invention provides novel biparatopic LRP5/LRP6 cross-reactive binding polypeptides, and more specifically novel biparatopic LRP5/LRP6 cross-reactive immunoglobulin single variable domain constructs which can inhibit Wnt signaling pathways. The invention also relates to specific sequences of such polypeptides, methods of their production, and methods of using them, including methods of treatment of diseases such as cancer.

3 Claims, 17 Drawing Sheets

Specification includes a Sequence Listing.

(56) References Cited

OTHER PUBLICATIONS

Alarcon, Marcelo A. et al. "A novel functional low-density lipoprotein receptor-related protein 6 gene alternative splice variant is associated with Alzheimer's disease" (2013) Neurobiology of Aging, 34, 1709.e9-1709.e18.
Pospisil, Heike et al. "Verification of predicted alternatively splice Wnt genes reveals two new splice variants (CTNNBI and LRP5) and altered Axin-I expression during tumour progression" BMC Genomics, (2006) 7:148, 14 pgs.
Ettenberg, PNAS, vol. 107, Inhibition of tumorgenesis driven by different Wnt proteins requires blockade of distinct ligand-binding regions by LRP6 antibodies, 2010.
Ahn et al., "Structural basis of Wnt signaling inhibition by Dickkopf binding to LRP5/6", Development Cell, 2011, vol. 21, No. 5, pp. 862-873.
Akiri et al., "Wnt pathway aberrations including autocrine Wnt activation occur at high frequency in human non-small- cell lung carcinoma", Oncogene, 2009, vol. 28, No. 21, pp. 2163-2172.
Atwell et al., "Stable heterodimers from remodeling the domain interface of a homodimer using a phage display library", Journal of Molecular Biology, 1997, vol. 270, No. 1, pp. 26-35.
Bafico et al., "An autocrine mechanism for constitutive Wnt pathway activation in human cancer cells", Cancer Cell, 2004, vol. 6, No. 5, pp. 497-506.
Barbas et al., "In vitro evolution of a neutralizing human antibody to human immunodeficiency virus type 1 to enhance affinity and broaden strain cross-reactivity", Proc. Natl. Acad. Sci., 1994; vol. 91; pp. 3809-3813.
Bourhis, Wnt Antagonists bind through a short peptide to the first B-propeller domain of LRP5/6, Cell Press, vol. 19, 2011, 10 pages.
Chen et al., "Activation of the Wnt pathway plays a pathogenic role in diabetic retinopathy in humans and animal models", The American Journal of Pathology, 2009, vol. 175, No. 6, pp. 2676-2685.
De Lau et al., "The R-spondin/Lgr5/Rnf43 module: regulator of Wnt signal strength", Genes & Development, 2014, vol. 28, No. 4, pp. 305-316.
DeAlmeida et al., "The Soluble Wnt Receptor Frizzled8CRD-hFc Inhibits the Growth of Teratocarcinomas In vivo", Cancer Research, 2007, vol. 67, No. 11, pp. 5371-5379.
DeLisa et al., "Monitoring GFP-operon fusion protein expression during high cell density cultivation of Escherichia coli using an on-line optical sensor", Biotechnology and Bioengineering, 1999, vol. 65, pp. 54-64.
Gao et al., "Elevated LRP6 levels correlate with vascular endothelial growth factor in the vitreous of proliferative diabetic 20 retinopathy", Molecular Vision, 2015, vol. 21, No. 21, pp. 665-672.
Giannakis et al., "RNF43 is frequently mutated in colorectal and endometrial cancers", Nat Genet., 2014; vol. 46, No. 12, pp. 1264-1266.
Hamers-Casterman et al., "Naturally occurring antibodies devoid of light chains", Nature, 1993, vol. 363, pp. 446-448.
Hawkins et al., "Selection of Phage Antibodies by Biding Affinity Mimicking Affinity Maturation", J. Mol. Biol., 1992, vol. 226, pp. 889-896.
Holt et al., "Domain antibodies: proteins for therapy", Trends in Biotechnology, 2003, vol. 21, No. 11, pp. 484-490.

Hong et al., "Catenin promotes T regulatory cell responses in tumors by inducing vitamin A metabolism in dendritic cells", Cancer Research, 2015, vol. 75, No. 4, pp. 656-665.
Jackson et al., "In vitro antibody maturation. Improvement of a high affinity, neutralizing antibody against IL-1 beta", The Journal of Immunology, 1995, vol. 154, No. 7, pp. 3310-3319.
Jiang et al., "Inactivating mutations of RNF43 confer Wnt dependency in pancreatic ductal; adenocarcinoma", PNAS, 2013, vol. 110, No. 31, pp. 12649-12654.
Johnson, K.S. et al., "Affinity maturation of antibodies using phage display", in McCafferty, Hoogenboom & Chiswell (Eds.), A Practical Approach: Antibody Engineering, IRL Press, vol. 256, 1996, pp. 41-58.
Khramtsov et al., "Wnt/beta-catenin pathway activation is enriched in basal-like breast cancers and predicts poor butcome", The American Journal of Pathology, 2010, vol. 176, No. 6, pp. 2911-2920.
Königshoff et al., "Functional Wnt Signaling Is Increased in Idiopathic Pulmonary Fibrosis", PLoS One, 2008, vol. 3, No. 5, pp. 21-42.
Lam et al., "Wnt coreceptor Lrp5 is a driver of idiopathic 10 pulmonary fibrosis", Am J Respir Crit Care Med., 2014, vol. 190, No. 2, pp. 185-195.
Liu et al., "LRP6 overexpression defines a class of breast cancer 20 subtype and is a target for therapy", PNAS, 2010, vol. 107, No. 11, pp. 5136-5141.
Marks et al., "By-Passing Immunization: Building High Affinity Human Antibodies by Chain Shuffling", Biotechnology, 1992, vol. 10, pp. 779-783.
Muyldermans Serge, "Nanobodies: Natural Single-Domain Antibodies", The Annual Review of Biochemistry, 2013, vol. 82, pp. 775-797.
Nakashima et al., "Wnt1 overexpression associated with tumor proliferation and a poor prognosis in non-small cell lung cancer patients", Oncology Reports, 2008, vol. 19, No. 1, pp. 203-209.
Oderup et al., "Canonical and Noncanonical Wnt Proteins Program Dendritic Cell Responses for Tolerance", Journal of Immunology, 2013, vol. 190, No. 12, pp. 6162-6134.
Riechmann et al., "Single domain antibodies: comparison of camel VH and camelised human VH domains", Journal of Immunological Methods, 1999, vol. 231, pp. 25-38.
Seshagiri et al., "Recurrent R-spondin fusions in colon cancer", Nature, 2012; vol. 488, No. 7413, pp. 660-664.
Shier et al., "Identification of functional and structural amino-acid residues by parsimonious mutagenesis", Gene, 1996, vol. 169, pp. 147-155.
Ward et al., "Binding activities of a repertoire of single immunoglobulin variable domains secreted from *Escheria coli*", Nature, 1989, vol. 341, pp. 544-546.
Wilms B. et al., "High cell density fermentation for production of L Ncarbamoylase using anexpression system based on the *Escherichia coli* rhaBAD promoter", Biotechnology and Bioengineering; 2001, vol. 73, pp. 95-103.
Yelton et al., "Affinity Maturation of the BR96 Anti-Carcinoma Antibody by Codon-Based Mutagenesis", The Journal of Immunology, 1995, vol. 155, pp. 1994-2004.
Zhang et al., "Canonical Wnt Signaling Is Required for Pancreatic Carcinogenesis", Cancer Research, 2013; vol. 73, No. 15, pp. 4909-4922.
Zhong et al., "Lrp5 and Lrp6 play compensatory roles in mouse intestinal Development", J Cell Biochem, 2012, vol. 113, No. 1, pp. 31-38.

* cited by examiner

US 11,952,418 B2

BIPARATOPIC POLYPEPTIDES ANTAGONIZING WNT SIGNALING IN TUMOR CELLS

SEQUENCE LISTING

The instant application contains a Sequence Listing which has been submitted in ASCII format via EFS-Web and is hereby incorporated by reference in its entirety. Said ASCII copy, created on Feb. 23, 2023, is named 12-0401-US-2_SL.txt and is 82,936 bytes in size.

FIELD OF THE INVENTION

The present invention relates to novel low-density lipoprotein receptor-like protein 5 (LRP5) and low-density lipoprotein receptor-like protein 6 (LRP6) binding polypeptides. The invention also relates to nucleic acids encoding such polypeptides; to methods for preparing such polypeptides; to host cells expressing or capable of expressing such polypeptides; to compositions comprising such polypeptides; and to uses of such polypeptides or such compositions, in particular for therapeutic purposes in the field of cancer diseases.

BACKGROUND OF THE INVENTION

Activation of the Wnt signaling pathway requires binding of extracellular Wnt ligands to the Frizzled receptor and to the co-receptor LRP5 (Accession number: UniProtKB-O75197/LRP5_HUMAN) or its closely related homologue LRP6 (Accession number: UniProtKB-O75581/LRP6_HUMAN). There are 19 Wnt 30 proteins and 10 Frizzled receptors in mammalian cells. In the absence of Wnt ligand, cytoplasmic beta-catenin is phosphorylated by a protein complex consisting of the scaffolding proteins Axin and APC and the kinases GSK3beta and CK1a. Subsequent recognition by the ubiquitin ligase beta-TrcP leads to ubiquitin-mediated degradation of beta-catenin. In the presence of Wnt ligand, binding of Wnt to Frizzled and LRP5 or LRP6 leads to recruitment of the cytoplasmic effector protein Dvl and phosphorylation of the LRP5 or LRP6 cytoplasmic tail, which provides the docking site for Axin. Axin sequestration by LRP5 or LRP6 leads to the inactivation of the Axin-APC-GSK3beta complex and, therefore, intracellular beta-catenin stabilization and accumulation. Hence, cytoplasmic levels of beta-catenin rise, and beta-catenin migrates to the nucleus and complexes with members of the T-cell factor (TCF)/Lymphoid enhancer-binding factor (LEF) family of transcription factors. Basal transcription machinery and transcriptional co-activators are then recruited, including cAMP response element-binding protein (CREB)-binding protein (CBP) or its homolog p300, leading to expression of various target genes, including Axin2, cyclin D1 and c-Myc.

An additional level of ligand-dependent Wnt pathway regulation is mediated by the E3 ligase RNF43, and its closely related homologue ZNRF3, and by the secreted R-Spondin proteins (de Lau et al. "The R-spondin/Lgr5/Rnf43 module: regulator of Wnt signal strength". *Genes Dev.* 2014; 28(4):305-16). RNF43 mediates the ubiquitination of the Frizzled/LRP5 or LRP6 receptor complex at the cell surface, leading to its degradation and, thereby, inhibiting ligand-dependent Wnt pathway activity. The activity of RNF43 is counteracted by the R spondin family members (R-spondin 1 to 4 ligands). When R-Spondin ligand is present, it removes RNF43 from the cell surface, allowing Frizzled/LRP5 or LRP6 complex accumulation and enhancement of Wnt signaling in the presence of Wnt ligands.

LRP5 and LRP6 function as gatekeepers of ligand dependent Wnt signaling activation and, therefore, may be considered as targets to achieve complete blockade of the pathway mediated by all 19 Wnt ligands and 10 Frizzled receptors and enhanced by R-spondin ligands. In particular, Wnt ligands can be divided into a Wnt1 class and a Wnt3a class, each binding to different epitopes/regions of LRP5 and LRP6 for signaling. The ectodomain of LRP5 and LRP6 comprises four repeating units of a beta-propeller connected to an EGF-like domain, followed by three LDLR-type A repeats. Combined structural and functional analyses of LRP5 and LRP6 suggest that Wnt1 (Wnt1-class ligand) binds to a fragment containing beta-propeller 1 and 2 and Wnt3a binds to a fragment containing beta-propeller 3 and 4 of LRP6. So far, only a low-resolution picture of LRP6 ectodomain containing beta-propeller from 1 to 4 regions is reported (Ahn et al. "Structural basis of Wnt signaling inhibition by Dickkopf binding to LRP5/6". *Dev Cell.* 2011; 21(5):862-73). However, the uncertainties of these low-resolution reconstructions (40 A°) and the absence of structural data of the LRP6 ectodomain in complex with the Wnt ligands do not allow defining the exact epitopes involved in Wnt1 or Wnt3a ligand binding.

Hyperactivation of Wnt signaling is involved in the pathogenesis of various types of cancer. In some cancer types frequent mutations in downstream signaling molecules contribute to constitutively activated Wnt pathway (e.g. APC mutations in colorectal cancer; beta-catenin activating mutation in hepatocellular carcinoma). In contrast, in Triple Negative Breast Cancer (TNBC), Non Small Cell Lung Cancer (NSCLC), pancreatic adenocarcinoma and in a subset of Colo-Rectal Cancer (CRC) and endometrial cancers, Wnt signaling activation is driven by a ligand dependent mechanism (i.e. by an autocrine/paracrine Wnt activation), as detected by beta-catenin intracellular accumulation. In NSCLC, TNBC and pancreatic adenocarcinoma, ligand dependent Wnt activation is mediated by multiple mechanisms, including increased expression of the Wnt ligands and/or of LRP5 and LRP6 receptors, or silencing of LRP5 and LRP6 negative regulator DKK1 (TNBC: Liu et al. "LRP6 overexpression defines a class of breast cancer subtype and is a target for therapy". *Proc Natl Acad Sci USA* 2010; 107 (11):5136-41; Khramtsov et al. "Wnt/beta-catenin pathway activation is enriched in basal-like breast cancers and predicts poor outcome". *Am J Pathol.* 2010; 176(6): 2911-20; NSCLC: Nakashima et al. "Wnt1 overexpression associated with tumor proliferation and a poor prognosis in non-small cell lung cancer patients". *Oncol Rep.* 2008; 19(1):203-9; Pancreatic cancer: Zhang et al. "Canonical wnt signaling is required for pancreatic carcinogenesis". *Cancer Res.* 2013; 73(15):4909-22). In particular, published data have shown that in healthy tissues (e.g. mammary and lung epithelium), beta-catenin is localized solely at the plasma membrane. In contrast, the majority of TNBC, NSCLC and pancreatic adenocarcinoma primary clinical samples showed beta-catenin intracellular accumulation (i.e. in the cytoplasm/nucleus; biomarker of Wnt signaling activation), due to aberrant Wnt signaling. Recent publications have shown that ligand dependent Wnt signaling activation is mediated by mutated/inactivated RNF43 (Giannakis et al. "RNF43 is frequently mutated in colorectal and endometrial cancers". *Nat Genet.* 2014; 46(12):1264-6) or by activating R-Spondin fusion transcripts (encoding R-spondin2 or R-spondin3 proteins driven by constitutively active strong promoters; Seshagiri et al. "Recurrent R-spondin fusions in colon cancer". *Nature* 2012; 488(7413):660-4) in a subset of CRC and endometrial cancers. Inactivating RNF43 mutations and R-Spondin fusion transcripts have both been shown to augment ligand dependent Wnt signaling in vitro by increasing the abundance of Frizzled on the cell surface. Ligand dependent Wnt activation in tumors was shown to drive tumor growth and resistance to chemotherapy or immunotherapy, and is linked to recurrence in pre-clinical models.

Some LRP5 or LRP6 binding molecules, able to modulate the Wnt signaling pathway, are known in the art:

Dickkopf-1 (DKK1) is a LRP5 and LRP6 inhibitor. DKK1 associates with both the Wnt co-receptors, LRP5 and 6, and the transmembrane protein, Kremen, inhibits Wnt signaling and leads to rapid LRP5 and LRP6 internalization. It is shown that DKK1 inhibits both Wnt1 and Wnt3a mediated signaling. Structural modeling studies show that a single DKK1 molecule cooperatively binds to an extended region of the LRP6 ectodomain (from beta-propeller 1 to 3). The structural analyses suggest a DKK1 cooperative binding-interaction with LRP6 with an initial binding to the beta-propeller 3 region that facilitates the interaction/binding to the beta-propeller 1 and 2 region via a conformation change of the LRP6 ectodomain. However, elucidation of the defined epitopes within the beta-propeller 1, 2 and 3 domains involved in the DKK1 binding to LRP6 is lacking due to the low resolution of the structural reconstructions of the full LRP6 ectodomain bound to DKK1, as mentioned.

It was shown that DKK1 treatment in vivo causes severe toxicity in the gastrointestinal tract. In particular, it was shown that adenovirus mediated expression of DKK1 in adult mice markedly inhibited proliferation in small intestine and colon, accompanied by progressive architectural degeneration, severe body weight loss and mortality from colitis and systemic infection. In particular, LRP5 and LRP6 are expressed in the intestine in the proliferative epithelial cells and are required for proliferation of the intestinal epithelium, suggesting that LRP5 and LRP6 inhibition may be toxic for this and other normal tissues (Zhong et al. "Lrp5 and Lrp6 play compensatory roles in mouse intestinal development". *J Cell Biochem.* 2012; 113(1):31-8). This makes it doubtful whether agents which inhibit LRP5 and LRP6, or which inhibit the Wnt (Wnt1 and Wnt3a) signaling pathway in general, can be used for therapeutic purposes, e.g. can be developed as anti-cancer drugs.

WO2009/056634 refers to LRP6 binding molecules that may either interact with the Wnt1 signaling pathway or with the Wnt3/3a signaling pathway, which may be antagonistic or agonistic, and which may be used for diagnostic purposes or to treat "Wnt signaling-related disorders", such as osteoarthritis, polycystic kidney disease, or cancer. No specific examples for such binding molecules, defined by their amino acid sequence, are provided in this document.

WO2011/138391 and WO2011/138392 are disclosing multivalent LRP6 binding antibodies. WO2011/138391 is claiming antibodies which are blocking one Wnt signaling pathway (Wnt1 or Wnt3) without potentiating the other pathway (Wnt3 or Wnt1, respectively). WO2011/138392 i.a. provides antibodies or antibody fragments which potentiate Wnt signaling by LRP6 receptor clustering.

WO2011/138391 explains that for achieving the desired effect, LRP6 binding molecules need to be formatted into full length IgG antibodies. Examples of LRP6 biparatopic molecules are provided which include an IgG molecule, having a first binding specificity, coupled to a single chain Fv portion, having the second binding specificity. Some formats are described as having significantly reduced thermal stability (Tm of 50 to 52° C.). An Fc portion may impart effector functions on an IgG molecule, such as complement-dependent cytotoxicity (CDC) or antibody-dependent cellular toxicity (ADCC).

WO2013/067355 discloses half-life extended biparatopic LRP6 binding scFv immunoglobulin constructs, derived from IgG molecules disclosed in WO2011/138391.

WO2011/119661 discloses antibodies that bind to LRP6 and inhibit the signaling induced by a first Wnt isoform, esp. by Wnt3 or Wnt3a, but potentiate signaling induced by a second Wnt isoform, which may be a Wnt1, 2, 2b, 4, 6, 7a, 7b, 8a, 9a, 9b, 10a or 10b isoform. Bispecific molecules are disclosed which bind to the E1-E2 region of LRP6 as well as to the E3-E4 region of LRP6. The knob-in-hole technique was used to generate bispecific antibodies.

Identification of the binding epitopes (defined amino acid residues within the LRP6 ectodomain/beta-propeller regions) involved in the binding of the LRP6 antibodies is not provided in WO2009/056634, nor in WO2011/138391 or WO2013/067355, and only partially in WO2011/119661. In particular, LRP6 binding antibodies can inhibit Wnt signaling via alternative mechanisms according to binding to different regions of LRP6, including competing with Wnts directly or inhibiting formation of ternary receptor complexes (Wnt-LRP6-Frizzled), whereas others enhance signaling, possibly by receptor clustering (Ahn et al. "Structural basis of Wnt signaling inhibition by Dickkopf binding to LRP5/6". *Dev Cell.* 2011; 21(5):862-73).

However, none of the binding molecules described in the art has so far been authorized by health authorities for the use as a medicament to treat any disease. Specifically, such use requires very specific binding properties, the right specificity, so that such molecules does or does not bind, activate or inhibit other targets (e.g. resulting in undesired activation or inhibition of other signaling pathways, or lack of activation or inhibition with respect to target isoforms), in the case of bi- or multispecific agents the right balance between the two or more binding specificities, suitable pharmacokinetic and -dynamic properties, an acceptable toxicological profile, and of course in vivo efficacy.

In view of the above, there is a need for novel therapeutic agents that allow an efficient treatment of several types of cancer diseases and tumors. It is thus an object of the invention to provide such pharmacologically active agents that can be used in the treatment of several cancer diseases, including NSCLC and TNBC.

In particular, it is an object of the invention to provide such pharmacologically active agents, compositions and/or methods of treatment that provide certain advantages compared to the agents, compositions and/or methods currently used and/or known in the art. These advantages include in vivo efficacy, improved therapeutic and pharmacological properties, less side effects, and other advantageous properties such as improved ease of preparation or reduced costs of goods, especially as compared to candidate drugs already known in the art.

BRIEF SUMMARY OF THE INVENTION

According to a first aspect of the invention, the present invention provides polypeptides which specifically bind to LRP5 or LRP6, wherein such polypeptide of the invention comprises a first immunoglobulin single variable domain (a) selected from the group of immunoglobulin single variable domains (i) to (iii) defined by having the following CDR sequences:

(i):
CDR1: (=SEQ ID NO: 1)
TYTVG

CDR2: (=SEQ ID NO: 2)
AIRRRGSSTYYADSVKG

CDR3: (=SEQ ID NO: 3)
DTRTVALLQYRYDY (ii):
CDR1: (=SEQ ID NO: 4)
SYAMG

CDR2: (=SEQ ID NO: 5)
AIRRSGRRTYYADSVKG

CDR3: (=SEQ ID NO: 6)
ARRVRSSTRYNTGTWWWEY (iii):
CDR1: (=SEQ ID NO: 7)
RYTMG

CDR2: (=SEQ ID NO: 8)
AIVRSGGSTYYADSVKG

CDR3: (=SEQ ID NO: 9)
DRRGRGENYILLYSSGRYEY, and a second immunoglobulin single variable domain (b) selected from the group of immunoglobulin single variable domains (iv) and (v) defined by having the following CDR sequences:

(iv):
CDR1: (=SEQ ID NO: 10)
SYAMG

CDR2: (=SEQ ID NO: 11)
AISWSGGSTYYADSVKG

CDR3: (=SEQ ID NO: 12)
SPIPYGSLLRRRNNYDY (v):
CDR1: (=SEQ ID NO: 13)
SYAMG

CDR2: (=SEQ ID NO: 14)
AISWRSGSTYYADSVKG

CDR3: (=SEQ ID NO: 15)
DPRGYGVAYVSAYYEY.

The terms "first" and "second" with respect to such immunoglobulin single variable domains is solely intended to indicate that these domains are two different domains (as they will at least include different CDR sequences). Thus, these terms shall not be understood to refer to the exact order or sequence of the domains within such polypeptide chain.

The polypeptides of the invention optionally comprise a third immunoglobulin single variable domain, such as especially an albumin binding immunoglobulin single variable domain, such as the Alb11 domain, comprising the following CDRs:

CDR1(Alb11): (=SEQ ID NO: 16)
SFGMS

CDR2(Alb11): (=SEQ ID NO: 17)
SISGSGSDTLYADSVKG

CDR3(Alb11): (=SEQ ID NO: 18)
GGSLSR.

According to a more specific embodiment, the polypeptides of the invention include immunoglobulin single variable domains which are VHH domains, and preferably humanized VHH domains.

According to an even more specific embodiment, the polypeptides of the invention include a first immunoglobulin single variable domain (a) selected from the group of immunoglobulin single variable domains (i) to (iii) having the following sequences:

(i): (=SEQ ID NO: 19)
AVQLVESGGGLVQPGGSLRLSCAASGRTFSTYTVGWFRQAPGKEREF
VAAIRRRGSSTYYADSVKGRFTISRDNSKNTVYLQMNSLRPEDTAVYY
CAADTRTVALLQYRYDYWGQGTLVTVSS (ii): (=SEQ ID NO: 20)
AVQLVESGGGLVQPGGSLRLSCAASGGTFSSYAMGWFRQAPGKERE
FVAAIRRSGRRTYYADSVKGRFTISRDNSKNTVYLQMNSLRPEDTAVYY
CAAARRVRSSTRYNTGTWWWEYWGQGTLVTVSS (iii): (=SEQ ID NO: 21)
AVQLVESGGGLVQPGGSLRLSCAASGLTFSRYTMGWFRQAPGKEREF
VAAIVRSGGSTYYADSVKGRFTISRDNSKNTVYLQMNSLRPEDTAVYY
CAADRRGRGENYILLYSSGRYEYWGQGTLVTVSS, and a second immunoglobulin single variable domain (b) selected from the group consisting of immunoglobulin single variable domains (iv) and (v) having the following sequences:

(iv): (=SEQ ID NO: 22)
EVQLVESGGGLVQPGGSLRLSCAASGRTFSSYAMGWFRQAPGKERE
FVAAISWSGGSTYYADSVKGRFTISRDNSKNTVYLQMNSLRPEDTAVY
YCAASPIPYGSLLRRRNNYDYWGQGTLVTVSS,
and (v): (=SEQ ID NO: 23)
EVQLVESGGGLVQPGGSLRLSCAASGGTFSSYAMGWFRQAPGKERE
FVAAISWRSGSTYYADSVKGRFTISRDNSKNTVYLQMNSLRPEDTAVY
YCAADPRGYGVAYVSAYYEYWGQGTLVTVSS.

According to a specifically preferred embodiment, the polypeptides of the invention additionally include a half-life extending moiety, wherein said half-life extending moiety is covalently linked to said polypeptide and is optionally selected from the group consisting of an albumin binding moiety, such as an albumin binding peptide or an albumin binding immunoglobulin domain, preferably an albumin binding immunoglobulin single variable domain, more preferably the Alb11 domain, a transferrin binding moiety, such as an anti-transferrin immunoglobulin domain, a polyethylene glycol molecule, human serum albumin, and a fragment of human serum albumin.

Specifically preferred are polypeptides which include, in addition to the two immunoglobulin single variable domains (a) and (b) as outlined above, an Alb11 domain having the following sequence:

```
                                        (=SEQ ID NO: 24)
EVQLVESGGGLVQPGNSLRLSCAASGFTFSSFGMSWVRQAPGKGLEW

VSSISGSGSDTLYADSVKGRFTISRDNAKTTLYLQMNSLRPEDTAVYYC

TIGGSLSRSSQGTLVTVSS
```

According to a further embodiment, the invention specifically includes polypeptides comprising or consisting of any of the following three polypeptide chains:
F13500575, having the sequence SEQ ID NO:25,
F13500571, having the sequence SEQ ID NO:26, and
F13500720, having the sequence SEQ ID NO:27.

According to further aspects, the invention relates to nucleic acid molecules, expression vectors, host cells, and methods of manufacturing used in the production of a polypeptide of the invention. Nucleic acid molecules encoding the polypeptides of the invention can be used, in an isolated form, for constructing respective expression vectors, which then may be transfected into host cells used for biopharmaceutical production of the polypeptides of the invention. Such method of manufacturing typically comprises the steps of culturing the host cell under conditions that allow expression of the polypeptide, recovering the polypeptide and purifying it according to methods known in the art.

Further aspects, embodiments, uses and methods involving the polypeptides of the invention will become clear from the following detailed description of the invention and from the appended claims.

The invention provides for novel molecules that allow a more efficient treatment of several cancer types, such as TNBC, CRC, and NSCLC, with less side effects. The polypeptides of the invention provide for a surprising therapeutic effect (i.e. efficacy) in the treatment of cancer patients, in that they may induce tumor regression resulting in pathological complete response (pCR). This, in turn, is expected to result in significant improvement of progression free survival and overall survival, especially in high unmet medical need indications such as e.g. in breast cancer. Thus, the polypeptides of the invention provide for novel therapeutic options in the treatment of several cancer types, esp. those showing a deregulated Wnt signaling pathway and beta-catenin accumulation.

Furthermore, the polypeptides of the invention are easy to manufacture, have a high stability and low antigenicity, and offer a variety of options regarding administration routes, in addition to injection and infusion.

BRIEF DESCRIPTION OF THE DRAWINGS

FIG. 3A shows the binding of three half-life extended biparatopic LRP5/LRP6 cross-reactive VHH constructs to human LRP5 overexpressing HEK293 cell lines when compared to the negative control consisting of a non-targeting binder (VHH construct that binds to a bacterial protein which is not expressed in HEK293 cells). FIG. 3B shows the binding of three half-life extended biparatopic LRP5/LRP6 cross-reactive VHH constructs to human LRP6 overexpressing HEK293 cell lines when compared to the negative control consisting of a non-targeting binder (VHH construct that binds to a bacterial protein which is not expressed in HEK293 cells).

FIG. 4A shows complete DKK1 competition of three half-life extended biparatopic LRP5/LRP6 cross-reactive VHH constructs for binding to human LRP5 overexpressing HEK293 cell lines, as detected by a FACS-based DKK1 competition assay. FIG. 4B shows complete DKK1 competition of three half-life extended biparatopic LRP5/LRP6 cross-reactive VHH constructs for binding to human LRP6 overexpressing HEK293 cell lines, as detected by a FACS-based DKK1 competition assay.

FIG. 5A shows complete inhibition of Wnt1 and Wnt3a pathway of three half-life extended biparatopic LRP5/LRP6 cross-reactive VHH constructs in a combined Wnt1 and Wnt3a reporter assay. FIG. 5B shows comparison of inhibition of Wnt1 and Wnt3a of other LRP6 binding molecules, Knob HC YW210.09 and MOR08168IgG1LALA 6475 scfv, in the combined Wnt1 and Wnt3a reporter assay. FIG. 5C shows comparison of inhibition of the Wnt1 and Wnt3a pathway of other LRP6 binding molecule, 802T, in the combined Wnt1 and Wnt3a reporter assay.

FIG. 6A shows inhibition of Wnt signaling in cancer cells, as detected by inhibition of relative Axin2 mRNA expression with three half-life extended biparatopic LRP5/LRP6 cross-reactive VHH constructs (final concentration of 1 mM). FIG. 6B shows inhibition of Wnt signaling in cancer cells, as detected by inhibition of relative cell proliferation as detected by decreased percentage (%) of viable cells, after treatment with three half-life extended biparatopic LRP5/LRP6 cross-reactive VHH constructs (final concentration of 1 mM) and by treatment with 802T, compared to F013500571 and untreated (control) cells (left-hand side/right-hand side diagram of FIG. 6B). FIG. 6C shows dose-response curve of PA-TU-8988S after treatment with one half-life extended biparatopic LRP5/LRP6 construct and 802T. FIG. 6D shows dose-response curve of YAPC after treatment with one half-life extended biparatopic LRP5/LRP6 construct and 802T.

FIG. 7A shows in vivo efficacy of the half-life extended biparatopic LRP5/LRP6 cross-reactive VHH construct F013500571 at 2, 4 and 10 mg/kg as compared to control in a Wnt driven tumor model (MMTV-Wnt1 xenograft model) (as measured by tumor volume [mm3]). FIG. 7B shows in vivo efficacy of the half-life extended biparatopic LRP5/LRP6 cross-reactive VHH construct F013500720 at 0.2, 0.4 and 1.0 mg/kg as compared to control in a Wnt driven tumor model (MMTV-Wnt1 xenograft model) (as measured by tumor volume [mm3]). FIG. 7C shows in vivo efficacy of the of Knob HC YW210.09 construct at 30 and 45 mg/kg as compared to control in a Wnt driven tumor models (MMTV-Wnt1 xenograft model) (as measured by tumor volume [mm3]).

FIG. 8A shows Wnt pathway inhibition in tumors treated with the half-life extended biparatopic LRP5/LRP6 cross-reactive VHH construct F013500571 as detected by reduction of Axin2 mRNA expression relative to the control group. FIG. 8B shows Wnt pathway inhibition in tumors treated with the half-life extended biparatopic LRP5/LRP6 cross-reactive VHH construct F013500720, as detected by reduction of Axin2 mRNA expression relative to the control group.

FIG. 9A shows the effect of Wnt3a driven signaling inhibition on pro-inflammatory cytokine TNFalpha release by dendritic cells upon treatment with a half-life extended biparatopic LRP5/LRP6 cross-reactive VHH construct. Each symbol represents a unique dendritic cell (DC) donor. Data shown are normalized to TNFalpha levels of the untreated control. FIG. 9B shows the effect of Wnt3a driven signaling inhibition on on T-cell activation, as determined by interferon-gamma release upon treatment with a half-life extended biparatopic LRP5/LRP6 cross-reactive VHH construct and each symbol represents a unique donor pair for DC and T cells.

DETAILED DESCRIPTION OF THE INVENTION

Definitions

Figure 1:
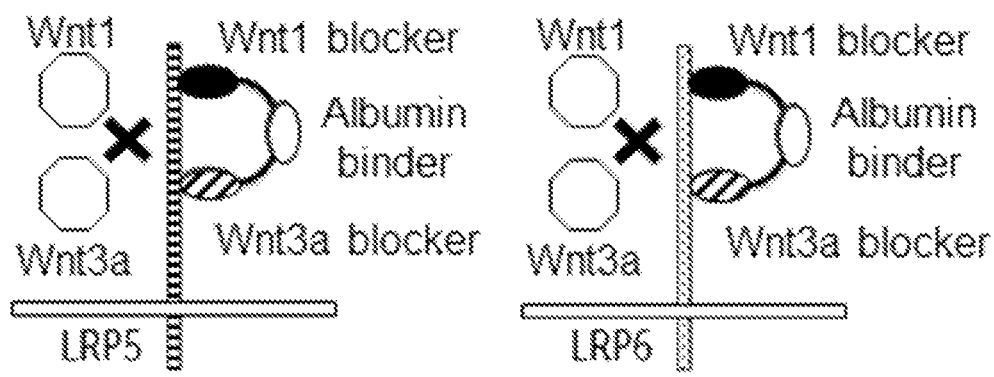
FIG. 1 shows a schematic representation of biparatopic polypeptides antagonizing Wnt1 and Wnt3a signaling. They consist of three domains, with two domains binding to distinct epitopes of LRP5 and LRP6 (Wnt1 and Wnt3a blocker) and one domain for half-life extension (human serum albumin binder).

The above and other aspects and embodiments of the invention will become clear from the further description herein, in which:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

b) Unless indicated otherwise, the terms "immunoglobulin" and "immunoglobulin sequence"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation;

c) The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

d) The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

e) The term "immunoglobulin variable domain" as used herein means an immunoglobulin domain essentially consisting of four "framework regions" which are referred to in the art and hereinbelow as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

f) The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the present invention are "domain antibodies", such as the immunoglobulin single variable domains VH and VL (VH domains and VL domains). Another important example of immunoglobulin single variable domains are "VHH domains" (or simply "VHHs") from camelids, as defined hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

f1) "VHH domains", also known as VHHs, VHH domains, VHH antibody fragments, and VHH antibodies, have originally been described as the antigen binding immunoglobulin (variable) domain of "heavy chain antibodies" (i.e. of "antibodies devoid of light chains"; Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "VH domains" or "VH domains") and from the light chain variable domains that are present in conventional 4-chain antibodies (which are referred to herein as "VL domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, VHH domain, VHH antibody fragment, VHH antibody, as well as "Nanobody®" and "Nanobody® domain" ("Nanobody" being a trademark of the company Ablynx N.V.; Ghent; Belgium) are used interchangeably and are representatives of immunoglobulin single variable domains (having the structure: FR1-CDR1-FR2-CDR2-FR3-CDR3-FR4 and specifically binding to an epitope without requiring the presence of a second immunoglobulin variable domain), and which may also be distinguished from VH domains by the so-called "hallmark residues", as defined in e.g. WO2009/109635, FIG. 1.

The amino acid residues of a VHH domain are numbered according to the general numbering for VH domains given by Kabat et al. ("Sequence of proteins of immunological interest", US Public Health Services, NIH Bethesda, MD, Publication No. 91), as applied to VHH domains from Camelids, as shown e.g. in FIG. 2 of Riechmann and Muyldermans, J. Immunol. Methods 231, 25-38 (1999). According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for VH domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Further structural characteristics and functional properties of VHH domains and polypeptides containing the same can be summarized as follows:

VHH domains (which have been "designed" by nature to functionally bind to an antigen without the presence of, and without any interaction with, a light chain variable domain) can function as a single, relatively small, functional antigen-binding structural unit, domain or polypeptide. This distinguishes the VHH domains from the VH and VL domains of conventional 4-chain antibodies, which by themselves are generally not suited for practical application as single antigen-binding proteins or immunoglobulin single variable domains, but need to be combined in some form or another to provide a functional antigen-binding unit (as in for example conventional antibody fragments such as Fab fragments; in scFv's, which consist of a VH domain covalently linked to a VL domain).

Because of these unique properties, the use of VHH domains—either alone or as part of a larger polypeptide—offers a number of significant advantages over the use of conventional VH and VL domains, scFv's or conventional antibody fragments (such as Fab- or F(ab')2-fragments):

only a single domain is required to bind an antigen with high affinity and with high selectivity, so that there is no need to have two separate domains present, nor to assure that these two domains are present in the right spacial conformation and configuration (i.e. through the use of especially designed linkers, as with scFv's);

VHH domains can be expressed from a single gene and require no post-translational folding or modifications;

VHH domains can easily be engineered into multivalent and multispecific formats (as further discussed herein);

VHH domains are highly soluble and do not have a tendency to aggregate (as with the mouse-derived antigen-binding domains described by Ward et al., Nature 341: 544-546 (1989));

VHH domains are highly stable to heat, pH, proteases and other denaturing agents or conditions and, thus, may be prepared, stored or transported without the use of refrigeration equipments, conveying a cost, time and environmental savings;

VHH domains are easy and relatively cheap to prepare, even on a scale required for production. For example, VHH domains and polypeptides containing the same can be produced using microbial fermentation (e.g. as further described below) and do not require the use of mammalian expression systems, as with for example conventional antibody fragments;

VHH domains are relatively small (approximately 15 kDa, or 10 times smaller than a conventional IgG)

compared to conventional 4-chain antibodies and antigen-binding fragments thereof, and therefore show high(er) penetration into tissues and can be administered in higher doses than such conventional 4-chain antibodies and antigen-binding fragments thereof;

VHH domains can show so-called cavity-binding properties (inter alia due to their extended CDR3 loop, compared to conventional VH domains) and can therefore also access targets and epitopes not accessible to conventional 4-chain antibodies and antigen-binding fragments thereof.

Methods of obtaining VHH domains binding to a specific antigen or epitope have been described earlier, e.g. in WO2006/040153 and WO2006/122786. As also described therein in detail, VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more fully human framework region sequences, and, in an even more specific embodiment, can contain human framework region sequences derived from DP-29, DP-47, DP-51, or parts thereof, optionally combined with JH sequences, such as JH5.

f2) "Domain antibodies", also known as "Dab"s, "Domain Antibodies", and "dAbs" (the terms "Domain Antibodies" and "dAbs" being used as trademarks by the GlaxoSmithKline group of companies) have been described in e.g. Ward, E. S., et al.: "Binding activities of a repertoire of single immunoglobulin variable domains secreted from *Escherichia coli*"; Nature 341: 544-546 (1989); Holt, L. J. et al.: "Domain antibodies: proteins for therapy"; TRENDS in Biotechnology 21(11): 484-490 (2003); and WO2003/002609.

Domain antibodies essentially correspond to the VH or VL domains of non-camelid mammalians, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans. As in the case of VHH domains, they are well expressed also in prokaryotic expression systems, providing a significant reduction in overall manufacturing cost.

Domain antibodies, as well as VHH domains, can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al., 1992, Biotechnology 10:779-783, or Barbas, et al., 1994, Proc. Nat. Acad. Sci, USA 91: 3809-3813.; Shier et al., 1995, Gene 169:147-155; Yelton et al., 1995, Immunol. 155: 1994-2004; Jackson et al., 1995, J. Immunol. 154(7):3310-9; and Hawkins et al., 1992, J. Mol. Biol. 226(3): 889 896; KS Johnson and RE Hawkins, "Affinity maturation of antibodies using phage display", Oxford University Press 1996.

f3) Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting are known in the art.

g) The terms "epitope" and "antigenic determinant", which can be used interchangeably, refer to the part of a macromolecule, such as a polypeptide, that is recognized by antigen-binding molecules, such as conventional antibodies or the polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as a conventional antibody or a polypeptide of the invention) that recognizes the epitope is called a paratope.

h) The term "biparatopic" (antigen-)binding molecule or "biparatopic" polypeptide as used herein shall mean a polypeptide comprising a first immunoglobulin single variable domain and a second immunoglobulin single variable domain as herein defined, wherein these two variable domains are capable of binding to two different epitopes of one antigen, which epitopes are not normally bound at the same time by one monospecific immunoglobulin, such as e.g. a conventional antibody or one immunoglobulin single variable domain. The biparatopic polypeptides according to the invention are composed of variable domains which have different epitope specificities, and do not contain mutually complementary variable domain pairs which bind to the same epitope. They do therefore not compete with each other for binding to LRP5 or LRP6.

i) A polypeptide (such as an immunoglobulin, an antibody, an immunoglobulin single variable domain, a polypeptide of the invention, or generally an antigen binding molecule or a fragment thereof) that can "bind", "bind to", "specifically bind", or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein.

k) Generally, the term "specificity" refers to the number of different types of antigens or epitopes to which a particular antigen-binding molecule or antigen-binding protein (such as an immunoglobulin, an antibody, an immunoglobulin single variable domain, or a polypeptide of the invention) can bind. The specificity of an antigen-binding protein can be determined based on its affinity and/or avidity. The affinity, represented by the equilibrium constant for the dissociation of an antigen with an antigen-binding protein ($K_D$), is a measure for the binding strength between an epitope and an antigen-binding site on the antigen-binding protein: the lesser the value of the $K_D$, the stronger the binding strength between an epitope and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an immunoglobulin single variable domain, or a polypeptide of the invention) and the pertinent antigen. Avidity is related to both the affinity between an epitope and its antigen binding site on the antigen-binding molecule and the number of pertinent binding sites present on the antigen-binding molecule.

Typically, antigen-binding proteins (such as the polypeptides of the invention) will bind with a dissociation constant ($K_D$) of 10E-5 to 10E-14 moles/liter (M) or less, and preferably 10E-7 to 10E-14 moles/liter (M) or less, more preferably 10E-8 to 10E-14 moles/liter, and even more preferably 10E-11 to 10E-13 (as measured e.g. in a Kinexa assay; known in the art), and/or with an association constant ($K_A$) of at least 10E7 ME-1, preferably at least 10E8 ME-1, more preferably at least 10E9 ME-1, such as at least 10E11 ME-1. Any $K_D$ value greater than 10E-4 M is generally considered to indicate non-specific binding. Preferably, a polypeptide of the invention will bind to the desired antigen with a $K_D$ less than 500 nM, preferably less than 200 nM, more preferably less than 10 nM, such as less than 500 pM. Specific binding of an antigen-binding protein to an antigen or epitope can be determined in any suitable manner known per se, including, for example, the assays described herein, Scatchard analysis and/or competitive binding assays, such as radioimmunoassays (RIA), enzyme immunoassays (EIA) and sandwich competition assays, and the different variants thereof known per se in the art.

l) The term "cross-reactive" in connection with binding molecules which are able to bind to LRP5 as well as to LRP6 ("LRP5/LRP6 cross-reactive") is intended to mean that such binding molecules can specifically bind to an epitope comprised in the LRP5 molecule, and can, alternatively, also specifically bind to an epitope comprised in the LRP6 molecule. Usually, such cross-reactivity may arise in case that the epitopes of the different proteins bound by such binding molecule have a similar structure and/or sequence, e.g. represent conserved epitopes, e.g. are shared by proteins belonging to the same protein family (e.g. LRP5 and LRP6, belonging to the LRP protein family).

m) Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO 98/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, lie, Val and Cys; and (v) aromatic residues: Phe, Tyr and Trp. Particularly preferred conservative amino acid substitutions are as follows:

Ala into Gly or into Ser;
Arg into Lys;
Asn into Gln or into His;
Asp into Glu;
Cys into Ser;
Gln into Asn;
Glu into Asp;
Gly into Ala or into Pro;
His into Asn or into Gln;
Ile into Leu or into Val;
Leu into lie or into Val;
Lys into Arg, into Gln or into Glu;
Met into Leu, into Tyr or into lie;
Phe into Met, into Leu or into Tyr;
Ser into Thr;
Thr into Ser;
Trp into Tyr;
Tyr into Trp or into Phe;
Val into lie or into Leu.

n) A nucleic acid or polypeptide molecule is considered to be "(in) essentially isolated (form)"—for example, when compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or polypeptide molecule is considered "essentially isolated" when it has been purified at least 2-fold, in particular at least 10-fold, more in particular at least 100-fold, and up to 1000-fold or more. A nucleic acid or polypeptide molecule that is "in essentially isolated form" is preferably essentially homogeneous, as determined using a suitable technique, such as a suitable chromatographical technique, such as polyacrylamide-gelelectrophoresis;

o) "Sequence identity" between e.g. two immunoglobulin single variable domain sequences indicates the percentage of amino acids that are identical between these two sequences. It may be calculated or determined as described in paragraph f) on pages 49 and 50 of WO2008/020079. "Sequence similarity" indicates the percentage of amino acids that either are identical or that represent conservative amino acid substitutions.

Target Specificity

The polypeptides of the invention have specificity for LRP5 as well as LRP6, in that they comprise immunoglobulin single variable domains specifically binding to epitopes included in both of these molecules (LRP5/LRP6 cross-reactive binding molecules).

The molecules of the invention shall bind to the human forms of LRP5 and LRP6, and preferably also to counterparts in other species relevant for drug development, i.e. cynomolgus and mouse LRP5 and LRP6.

Polypeptides of the Invention

In its broadest sense, the invention provides novel pharmacologically active agents for the treatment of cancer diseases. The agents according to the invention belong to a novel class of binding molecules, namely LRP5/LRP6 cross-reactive biparatopic polypeptides, comprising two or more immunoglobulin single variable domains binding to LRP5 and/or LRP6 at different epitopes. The terms "cross-reactive" and "biparatopic" are explained above, so that LRP5/LRP6 cross-reactive biparatopic molecules can be defined as molecules being able to bind to LRP5 at two different epitopes comprised in the LRP5 protein, and also being able to bind to LRP6 at the corresponding two epitopes comprised in the LRP6 protein.

More specifically, the polypeptides of the invention include:
- a first immunoglobulin single variable domain which is able to specifically bind to LRP5 as well as to LRP6 (LRP5/LRP6 cross-reactive) via an epitope/in a manner that results in inhibition of the Wnt1 signaling pathway, so that Wnt1-driven target gene transcription is inhibited, and
- a second immunoglobulin single variable domain which is able to specifically bind to LRP5 as well as to LRP6 (LRP5/LRP6 cross-reactive) via an epitope/in a manner that results in inhibition of the Wnt3a signaling pathway, so that Wnt3a-driven target gene transcription is inhibited.

Due to the two immunoglobulin single variable domains present in such polypeptide, wherein the two domains are binding to different epitopes (Wnt1/Wnt3a signaling related), these molecules are biparatopic binding molecules. This biparatopic binding mode is schematically shown in FIG. 1.

In this context, it should be noted that it is assumed that the polypeptides of the invention can bind to one single LRP5 or LRP6 molecule via both of its LRP5/LRP6 binding domains, as shown in FIG. 1 (intramolecular binding mode). However, other binding modes may occur as well.

Finally, it is assumed that the polypeptides of the invention are able to compete with DKK1—a natural ligand of LRP5 and LRP6, and interfering with Wnt1 and Wnt3a signaling—for binding to LRP5 and LRP6, thereby inhibiting the Wnt1 as well as the Wnt3a signaling pathway. However, also this theory should not be understood as limiting the scope of the invention.

More specifically, the polypeptides according to the invention specifically bind to LRP5 or LRP6, wherein such polypeptides comprise a first immunoglobulin single variable domain (a) selected from the group of immunoglobulin single variable domains (i) to (iii) defined by having the following CDR sequences:

```
(i):
CDR1:
                                     (=SEQ ID NO: 1)
TYTVG

CDR2:
                                     (=SEQ ID NO: 2)
AIRRRGSSTYYADSVKG

CDR3:
                                     (=SEQ ID NO: 3)
DTRTVALLQYRYDY
[=CDRs of the Wnt1-333E06mod domain]

(ii):
CDR1:
                                     (=SEQ ID NO: 4)
SYAMG

CDR2:
                                     (=SEQ ID NO: 5)
AIRRSGRRTYYADSVKG
```

```
-continued
CDR3:
                                     (=SEQ ID NO: 6)
ARRVRSSTRYNTGTWWWEY
[=CDRs of the Wnt1-333G06 domain]

(iii):
CDR1:
                                     (=SEQ ID NO: 7)
RYTMG

CDR2:
                                     (=SEQ ID NO: 8)
AIVRSGGSTYYADSVKG

CDR3:
                                     (=SEQ ID NO: 9)
DRRGRGENYILLYSSGRYEY
[=CDRs of the Wnt1-332D03mod domain],
``` and a second immunoglobulin single variable domain (b) selected from the group of immunoglobulin single variable domains (iv) and (v) defined by having the following CDR sequences:

```
(iv):
CDR1:
                                     (=SEQ ID NO: 10)
SYAMG

CDR2:
                                     (=SEQ ID NO: 11)
AISWSGGSTYYADSVKG

CDR3:
                                     (=SEQ ID NO: 12)
SPIPYGSLLRRRNNYDY
[=CDRs of the Wnt3a-093A01 domain]

(v):
CDR1:
                                     (=SEQ ID NO: 13)
SYAMG
CDR2:
                                     (=SEQ ID NO: 14)
AISWRSGSTYYADSVKG

CDR3:
                                     (=SEQ ID NO: 15)
DPRGYGVAYVSAYYEY
[=CDRs of the Wnt3a-367610 domain].
```

The use of the terms "first" and "second" with respect to such immunoglobulin single variable domains is solely intended to indicate that these domains are different domains, as they will include different CDR sequences and will bind to different epitopes. These terms shall, however, not be understood to refer to the exact order or sequence of the domains within such polypeptide chain. In other words, the above immunoglobulin single variable domains (a) and (b) may either be arranged in the order (a)-(b) or in the order (b)-(a) within such polypeptide of the invention.

The term "specifically bind to LRP5 or LRP6" is intended to mean that the immunoglobulin single variable domains (a) and (b) are cross-reactive with respect to LRP5 and LRP6. Of course, the binding properties of such molecules are determined by their (CDR) sequences, so that the feature "specifically binding to LRP5 or LRP6" set out above and in the claims is only intended to illustrate the utility of the invention, and not to limit the scope of this invention.

Immunoglobulin single variable domains typically essentially consist of four framework regions (FR1 to FR4, respectively) and three complementarity determining regions (CDR1 to CDR3, respectively). To be located within one polypeptide, or polypeptide chain, said first and said second immunoglobulin single variable domains need to be covalently linked, either directly or by a linker peptide.

Thus, the general structure of the molecules of the invention can also be depicted as follows:

FR(a)1-CDR(a)1-FR(a)2-CDR(a)2-FR(a)3-CDR(a)3-FR(a)4-[linker peptide]-FR(b)1-CDR(b)1-FR(b)2-CDR(b)2-FR(b)3-CDR(b)3-FR(b)4 wherein
FR(a) denotes a framework region of the first immunoglobulin single variable domain,
FR(b) denotes a framework region of the second immunoglobulin single variable domain,
CDR(a) denotes a CDR of the first immunoglobulin single variable domain,
CDR(b) denotes a CDR of the second immunoglobulin single variable domain,
[linker peptide] denotes a linker peptide that may optionally be present, wherein the CDRs are having the sequences as set out above.

Again, it shall be understood that (a) and (b) can be exchanged, i.e. that molecules having the general structure FR(b)1-CDR(b)1-FR(b)2-CDR(b)2-FR(b)3-CDR(b)3-FR(b)4-[linker peptide]-FR(a)1-CDR(a)1-FR(a)2-CDR(a)2-FR(a)3-CDR(a)3-FR(a)4 shall also be encompassed by the present invention.

The linker peptide optionally comprises or consists of a third domain, such as e.g. an albumin binding immunoglobulin single variable domain, such as the Alb11 domain, comprising the following CDRs:

```
CDR(Alb11)1:
                          (=SEQ ID NO: 16)
SFGMS

CDR(Alb11)2:
                          (=SEQ ID NO: 17)
SISGSGSDTLYADSVKG

CDR(Alb11)3:
                          (=SEQ ID NO: 18)
GGSLSR
```

This results in a group of polypeptides of the invention having the following general structure:

FR(a)1-CDR(a)1-FR(a)2-CDR(a)2-FR(a)3-CDR(a)3-FR(a)4-[linker peptide]-FR(Alb11)1-CDR(Alb11)1-FR(Alb11)2-CDR(Alb11)2-FR(Alb11)3-CDR(Alb11)3-FR(Alb11)4-[linker peptide]-FR(b)1-CDR(b)1-FR(b)2-CDR(b)2-FR(b)3-CDR(b)3-FR(b)4.

Again, the order of the three immunoglobulin single variable domains (a), (b), and Alb11 is not fixed but polypeptides in which the above domains are arranged in the order:

(b)-Alb11-(a)

shall be encompassed as well.

Furthermore, polypeptides having the Alb11 domain at the N- or C-terminal end of the polypeptide (e.g. Alb11-(a)-(b), Alb11-(b)-(a), (a)-(b)-Alb11, or (b)-(a)-Alb11) shall also be encompassed by the invention.

In three preferred embodiments, the polypeptides of the invention include immunoglobulin single variable domains defined as follows:

First preferred embodiment: Polypeptides comprising a first immunoglobulin single variable domain having the following CDR sequences:

```
                          (=SEQ ID NO: 1)
CDR1: TYTVG (=SEQ ID NO: 2)
CDR2: AIRRRGSSTYYADSVKG (=SEQ ID NO: 3)
CDR3: DTRTVALLQYRYDY
``` and a second immunoglobulin single variable domain having the following CDR sequences:

```
                          (=SEQ ID NO: 10)
CDR1: SYAMG (=SEQ ID NO: 11)
CDR2: AISWSGGSTYYADSVKG (=SEQ ID NO: 12)
CDR3: SPIPYGSLLRRRNNYDY.
```

Second preferred embodiment: Polypeptides comprising a first immunoglobulin single variable domain having the following CDR sequences:

```
                          (=SEQ ID NO: 4)
CDR1: SYAMG (=SEQ ID NO: 5)
CDR2: AIRRSGRRTYYADSVKG (=SEQ ID NO: 6)
CDR3: ARRVRSSTRYNTGTWWWEY
``` and a second immunoglobulin single variable domain having the following CDR sequences:

```
                          (=SEQ ID NO: 13)
CDR1: SYAMG (=SEQ ID NO: 14)
CDR2: AISWRSGSTYYADSVKG (=SEQ ID NO: 15)
CDR3: DPRGYGVAYVSAYYEY.
```

Third preferred embodiment: Polypeptides comprising a first immunoglobulin single variable domain having the following CDR sequences:

```
                          (=SEQ ID NO: 7)
CDR1: RYTMG (=SEQ ID NO: 8)
CDR2: AIVRSGGSTYYADSVKG (=SEQ ID NO: 9)
CDR3: DRRGRGENYILLYSSGRYEY
``` and a second immunoglobulin single variable domain having the following CDR sequences:

```
                          (=SEQ ID NO: 13)
CDR1: SYAMG (=SEQ ID NO: 14)
CDR2: AISWRSGSTYYADSVKG (=SEQ ID NO: 15)
CDR3: DPRGYGVAYVSAYYEY.
```

Of course, the variants as set out above—i.e. optionally including linker peptides and/or further domains, esp.

including an Alb11 domain, different orders of the immunoglobulin single variable domains—shall apply to these three preferred embodiments as well.

In a specifically preferred embodiment, the albumin binding immunoglobulin single variable domain is located between the two LRP5/LRP6 binding immunoglobulin single variable domains. Thus, three specifically preferred embodiments can be envisaged as follows:

First specifically preferred embodiment: Polypeptides comprising a first (LRP5/LRP6 binding) immunoglobulin single variable domain having the following CDR sequences:

```
                            (=SEQ ID NO: 1)
    CDR1: TYTVG (=SEQ ID NO: 2)
    CDR2: AIRRRGSSTYYADSVKG (=SEQ ID NO: 3)
    CDR3: DTRTVALLQYRYDY
``` an albumin binding immunoglobulin single variable domain having the following CDR sequences:

```
                            (=SEQ ID NO: 16)
    CDR1: SFGMS (=SEQ ID NO: 17)
    CDR2: SISGSGSDTLYADSVKG (=SEQ ID NO: 18)
    CDR3: GGSLSR;
``` and a second (LRP5/LRP6 binding) immunoglobulin single variable domain having the following CDR sequences:

```
                            (=SEQ ID NO: 10)
    CDR1: SYAMG (=SEQ ID NO: 11)
    CDR2: AISWSGGSTYYADSVKG (=SEQ ID NO: 12)
    CDR3: SPIPYGSLLRRRNNYDY;
``` either in this order, or the order of the above domains being changed.

Second specifically preferred embodiment: Polypeptides comprising a first (LRP5/LRP6 binding) immunoglobulin single variable domain having the following CDR sequences:

```
                            (=SEQ ID NO: 4)
    CDR1: SYAMG (=SEQ ID NO: 5)
    CDR2: AIRRSGRRTYYADSVKG (=SEQ ID NO: 6)
    CDR3: ARRVRSSTRYNTGTWWWEY;
``` an albumin binding immunoglobulin single variable domain having the following CDR sequences:

```
                            (=SEQ ID NO: 16)
    CDR1: SFGMS (=SEQ ID NO: 17)
    CDR2: SISGSGSDTLYADSVKG (=SEQ ID NO: 18)
    CDR3: GGSLSR;
``` and a second (LRP5/LRP6 binding) immunoglobulin single variable domain having the following CDR sequences:

```
                            (=SEQ ID NO: 13)
    CDR1: SYAMG (=SEQ ID NO: 14)
    CDR2: AISWRSGSTYYADSVKG (=SEQ ID NO: 15)
    CDR3: DPRGYGVAYVSAYYEY;
``` either in this order, or the order of the above domains being changed.

Third specifically preferred embodiment: Polypeptides comprising first (LRP5/LRP6 binding) immunoglobulin single variable domain having the following CDR sequences:

```
                            (=SEQ ID NO: 7)
    CDR1: RYTMG (=SEQ ID NO: 8)
    CDR2: AIVRSGGSTYYADSVKG (=SEQ ID NO: 9)
    CDR3: DRRGRGENYILLYSSGRYEY;
``` an albumin binding immunoglobulin single variable domain having the following CDR sequences:

```
                            (=SEQ ID NO: 16)
    CDR1: SFGMS (=SEQ ID NO: 17)
    CDR2: SISGSGSDTLYADSVKG (=SEQ ID NO: 18)
    CDR3: GGSLSR;
``` and a second (LRP5/LRP6 binding) immunoglobulin single variable domain having the following CDR sequences:

```
                            (=SEQ ID NO: 13)
    CDR1: SYAMG (=SEQ ID NO: 14)
    CDR2: AISWRSGSTYYADSVKG (=SEQ ID NO: 15)
    CDR3: DPRGYGVAYVSAYYEY;
``` either in this order, or the order of the above domains being changed.

The CDR sequences mentioned above are summarized in Tables IA, IB, and IC:

TABLE IA

CDR sequences of immunoglobulin single variable domains interfering with Wnt1 signaling:

|  | Wnt1-333E06mod | Wnt1-333G06 | Wnt1-332D03mod |
|---|---|---|---|
| CDR1 | TYTVG (SEQ ID NO: 1) | SYAMG (SEQ ID NO: 4) | RYTMG (SEQ ID NO: 7) |
| CDR2 | AIRRRGSSTYYADSVKG (SEQ ID NO: 2) | AIRRSGRRTYYADSVKG (SEQ ID NO: 5) | AIVRSGGSTYYADSVKG (SEQ ID NO: 8) |
| CDR3 | DTRTVALLQYRYDY (SEQ ID NO: 3) | ARRVRSSTRYNTGTWWWEY (SEQ ID NO: 6) | DRRGRGENYILLYSSGRYEY (SEQ ID NO: 9) |

TABLE IB

CDR sequences of immunoglobulin single variable domains interfering with Wnt3a signaling:

|  | Wnt3a-093A01 | Wnt3a-367B10 |
|---|---|---|
| CDR1 | SYAMG (SEQ ID NO: 10) | SYAMG (SEQ ID NO: 13) |
| CDR2 | AISWSGGSTYYADSVKG (SEQ ID NO: 11) | AISWRSGSTYYADSVKG (SEQ ID NO: 14) |
| CDR3 | SPIPYGSLLRRRNNYDY (SEQ ID NO: 12) | DPRGYGVAYVSAYYEY (SEQ ID NO: 15) |

TABLE IC

CDR sequences of immunoglobulin single variable domain binding to serum albumin (Alb11 domain):

|  | Alb11 domain |
|---|---|
| CDR1 | SFGMS (SEQ ID NO: 16) |
| CDR2 | SISGSGSDTLYADSVKG (SEQ ID NO: 17) |
| CDR3 | GGSLSR (SEQ ID NO: 18) |

In addition to the CDR sequences as set out above, the immunoglobulin single variable domains comprised in the polypeptides of the invention include immunoglobulin framework region (FR) sequences. These sequences are preferably not immunogenic in humans, and are therefore preferably human or humanized FR sequences. Suitable human or humanized FR sequences are known in the art. Specifically preferred FR sequences can be taken from the embodiments shown below, disclosing the complete immunoglobulin single variable domains and thereby CDR sequences as well as FR sequences.

According to a more specific embodiment, the polypeptides of the invention include immunoglobulin single variable domains which are VHH domains, and preferably humanized VHH domains.

According to an even more specific embodiment, the polypeptides of the invention include a first immunoglobulin single variable domain (a) selected from the group consisting of immunoglobulin single variable domains (i) to (iii) having the following sequences:

(i)
AVQLVESGGGLVQPGGSLRLSCAASGRTFS<u>TYTVG</u>WFRQAPGKEREFVAAI<u>RRRGSSTYYADSVKG</u>RFTISRDNSKNTVYLQMNSLRPEDTAVYYCAA<u>DTRTVALLQYRYDY</u>WGQGTLVTVSS
[=Wnt1-333E06mod domain; =SEQ ID NO: 19]

(ii)
AVQLVESGGGLVQPGGSLRLSCAASGGTFS<u>SYAMG</u>WFRQAPGKEREFVAAI<u>RRSGRRTYYADSVKG</u>RFTISRDNSKNTVYLQMNSLRPEDTAVYYCAA<u>ARRVRSSTRYNTGTWWWEY</u>WGQGTLVTVSS
[=Wnt1-333G06 domain; =SEQ ID NO: 20],
and (iii)
AVQLVESGGGLVQPGGSLRLSCAASGLTFS<u>RYTMG</u>WFRQAPGKEREFVAAI<u>VRSGGSTYYADSVKG</u>RFTISRDNSKNTVYLQMNSLRPEDTAVYYCAA<u>DRRGRGENYILLYSSGRYEY</u>WGQGTLVTVSS
[=Wnt1-332D03mod domain; =SEQ ID NO: 21], and a second immunoglobulin single variable domain (b) selected from the group consisting of immunoglobulin single variable domains (iv) and (v) having the following sequences:

(iv)
EVQLVESGGGLVQPGGSLRLSCAASGRTFS<u>SYAMG</u>WFRQAPGKEREFVAAI<u>SWSGGSTYYADSVKG</u>RFTISRDNSKNTVYLQMNSLRPEDTAVYYCAA<u>SPIPYGSLLRRRNNYDY</u>WGQGTLVTVSS
[=Wnt3a-093A01 domain; =SEQ ID NO: 22],
and (v)
EVQLVESGGGLVQPGGSLRLSCAASGGTFS<u>SYAMG</u>WFRQAPGKEREFVAAI<u>SWRSGSTYYADSVKG</u>RFTISRDNSKNTVYLQMNSLRPEDTAVYYCAA<u>DPRGYGVAYVSAYYEY</u>WGQGTLVTVSS
[=Wnt3a-367B10 domain; =SEQ ID NO: 23].

Preferred embodiments are polypeptides comprising
a first immunoglobulin single variable domain having the amino acid sequence as shown in SEQ ID NO:19 and a second immunoglobulin single variable domain having the amino acid sequence as shown in SEQ ID NO:22; or
a first immunoglobulin single variable domain having the amino acid sequence as shown in SEQ ID NO:20 and a second immunoglobulin single variable domain having the amino acid sequence as shown in SEQ ID NO:23; or
a first immunoglobulin single variable domain having the amino acid sequence as shown in SEQ ID NO:21 and a second immunoglobulin single variable domain having the amino acid sequence as shown in SEQ ID NO:23.

Thus, the above embodiments can schematically be presented as isvd(a)-[linker peptide]-isvd(b), wherein "isvd" denotes the respective immunoglobulin single variable domain, and wherein otherwise the same definitions and variants shall apply as set out above, esp. with respect to the presence of optional linker peptides and/or further domains, esp. an Alb11 domain, and with respect to different orders of the immunoglobulin single variable domains.

According to specific embodiments of the invention, the above polypeptides may additionally include a half-life extending moiety, wherein said half-life extending moiety is covalently linked to said polypeptide and is optionally selected from the group consisting of an albumin binding moiety, such as an albumin binding peptide or an albumin binding immunoglobulin domain, preferably an albumin binding immunoglobulin single variable domain, more preferably the Alb11 domain, a transferrin binding moiety, such as an anti-transferrin immunoglobulin domain, a polyethylene glycol molecule, serum albumin, preferably human serum albumin, and a fragment of (human) serum albumin.

The sequence of the above-mentioned Alb11 immunoglobulin single variable domain is as follows:

EVQLVESGGGLVQPGNSLRLSCAASGFTFS<u>SFGMS</u>WVRQAPGKGLEWVSSI

SGSGSDTLYADSVKGRFTISRDNAKTTLYLQMNSLRPEDTAVYYCTI<u>GGSL</u>

<u>SRSS</u>QGTLVTVSS
(=Alb11 domain; =SEQ ID NO: 24)

Further examples of immunoglobulin single variable domains binding to human serum albumin are known in the art, and are described in further detail in e.g. international patent publications WO2006/122787 and WO2008/028977. Other peptides binding to human serum albumin are described e.g. in WO2008/068280, WO2009/127691, and WO2011/095545.

Thus, three preferred specific embodiments of the invention are as follows:

First preferred specific embodiment: Polypeptides comprising
- a first (LRP5/LRP6 binding) immunoglobulin single variable domain having the amino acid sequence as shown in SEQ ID NO:19;
- an albumin binding immunoglobulin single variable domain having the amino acid sequence as shown in SEQ ID NO:24;
- a second (LRP5/LRP6 binding) immunoglobulin single variable domain having the amino acid sequence as shown in SEQ ID NO:22;

either in this order, or the order of the above three domains being changed.

Second preferred specific embodiment: Polypeptides comprising
- a first (LRP5/LRP6 binding) immunoglobulin single variable domain having the amino acid sequence as shown in SEQ ID NO:20;
- an albumin binding immunoglobulin single variable domain having the amino acid sequence as shown in SEQ ID NO:24;
- a second (LRP5/LRP6 binding) immunoglobulin single variable domain having the amino acid sequence as shown in SEQ ID NO:23;

either in this order, or the order of the above three domains being changed.

Third preferred specific embodiment: Polypeptides comprising
- a first (LRP5/LRP6 binding) immunoglobulin single variable domain having the amino acid sequence as shown in SEQ ID NO:21;
- an albumin binding immunoglobulin single variable domain having the amino acid sequence as shown in SEQ ID NO:24;
- a second (LRP5/LRP6 binding) immunoglobulin single variable domain having the amino acid sequence as shown in SEQ ID NO:23;

either in this order, or the order of the above three domains being changed.

In even more specifically preferred embodiments, the albumin binding immunoglobulin single variable domain is located between the two LRP5/LRP6 binding immunoglobulin single variable domains.

The sequences of the immunoglobulin single variable domains mentioned above are summarized in Tables IIA, IIB, and IIC:

TABLE IIA

Sequences of immunoglobulin single variable domains interfering with Wnt1 signaling.

| VHH ID SEQ ID NO: | FR1 | CDR1 | FR2 | CDR2 | FR3 | CDR3 | FR4 |
|---|---|---|---|---|---|---|---|
| Wnt1-333E06 mod SEQ ID NO: 19 | AVQL VESG GGLV QPGG SLRL SCAA SGRT FS | TYTV G | WFR QAP GKE REF VA | AIRR RGSS TYYA DSVK G | RFTI SRDN SKNT VYLQ MNSL RPED TAVY YCAA | DTRT VALL QYRY DY | WGQ GTL VTV SS |
| Wnt1-333G06 SEQ ID NO: 20 | AVQL VESG GGLV QPGG SLRL SCAA SGGT FS | SYAM G | WFR QAP GKE REF VA | AIRR SGRR TYYA DSVK G | RFTI SRDN SKNT VYLQ MNSL RPED TAVY YCAA | ARRV RSST RYNT GTWW YWE | WGQ GTL VTV SS |
| Wnt1-332D03 mod SEQ ID NO: 21 | AVQL VESG GGLV QPGG SLRL SCAA SGLT FS | RYTM G | WFR QAP GKE REF VA | AIVR SGGS TYYA DSVK G | RFTI SRDN SKNT VYLQ MNSL RPED TAVY YCAA | DRRG RGEN YILL YSSG RYEY | WGQ GTL VTV SS |

TABLE IIB

Sequences of immunoglobulin single variable domains interfering with Wnt3a signaling:

| VHH ID SEQ ID NO: | FR1 | CDR1 | FR2 | CDR2 | FR3 | CDR3 | FR4 |
|---|---|---|---|---|---|---|---|
| Wnt3a-093A01 SEQ ID NO: 22 | EVQL VESG GGLV QPGG SLRL SCAA SGRT FS | SYAM G | WFR QAP GKE REF VA | AISW SGGS TYYA DSVK G | RFTI SRDN SKNT VYLQ MNSL RPED TAVY YCAA | SPIP YGSL LRRR NNYD Y | WGQ GTL VTV SS |
| Wnt3a-367B10 SEQ ID NO: 23 | EVQL VESG GGLV QPGG SLRL SCAA SGGT FS | SYAM G | WFR QAP GKE REF VA | AISW RSGS TYYA DSVK G | RFTI SRDN SKNT VYLQ MNSL RPED TAVY YCAA | DPRG YGVA YVSA YYEY | WGQ GTL VTV SS |

TABLE IIC

Sequence of immunoglobulin single variable
domain binding to serum albumin (Alb11 domain):

| VHH ID SEQ ID NO: | FR1 | CDR1 | FR2 | CDR2 | FR3 | CDR3 | FR4 |
|---|---|---|---|---|---|---|---|
| Alb11 SEQ ID NO: 24 | EVQLVESGGGLVQPGNSLRLSCAASGFTFS | SFGMS | WVRQAPGKGLEWVS | SISGSGSDTLYADSVKG | RFTISRDNAKTTLYLQMNSLRPEDTAVYYCTI | GGSLSR | SSQGTLVTVSS |

As set out above, the (at least two) immunoglobulin single variable domains present in a polypeptide of the invention can be linked to each other either directly, without use of a linker, or via a linker. The linker is preferably a linker peptide and will, according to the invention, be selected so as to allow binding of the at least two different immunoglobulin single variable domains to each of their target epitopes.

Suitable linkers will inter alia depend on the epitopes and, specifically, the distance between the epitopes on the target molecules to which the immunoglobulin single variable domains shall bind. This will be clear to the skilled person based on the disclosure herein, optionally after some limited degree of routine experimentation.

Thus, suitable linkers may comprise an amino acid sequence, e.g. having a length of 9 or more amino acids, preferably at least 17 amino acids, such as about 20 to 40 amino acids. The linker sequence may be a naturally occurring sequence or a non-naturally occurring sequence. If used for therapeutic purposes, the linker is preferably non-immunogenic in the subject to which the polypeptide of the invention is administered.

One useful group of linker sequences are linkers derived from the hinge region of heavy chain antibodies as described in WO1996/34103 and WO1994/04678. Other examples are poly-alanine linker sequences such as Ala-Ala-Ala.

Further preferred examples of linker sequences are Gly/Ser linkers of different length such as (gly$_x$ser$_y$)$_z$ linkers, including e.g. (gly$_4$ser)$_3$ (SEQ ID NO:50), (gly$_4$ser)$_5$ (SEQ ID NO:51), (gly$_4$ser)$_7$ (SEQ ID NO:52), (gly$_3$ser)$_3$ (SEQ ID NO:53), (gly$_3$ser)$_5$ (SEQ ID NO:54), (gly$_3$ser)$_7$ (SEQ ID NO: 55), (gly$_3$ser$_2$)$_3$ (SEQ ID NO: 56), (gly$_3$ser$_2$)$_5$ (SEQ ID NO:57), and (gly$_3$ser$_2$)$_7$ (SEQ ID NO:58).

Alternatively, or in addition, to a polypeptide linker, the at least two immunoglobulin single variable domains present in a polypeptide of the invention may be linked to each other via another moiety, such as another polypeptide which, in a preferred but non-limiting embodiment, may be a further immunoglobulin single variable domain as already described above. Such moiety may either be essentially inactive or may have a biological effect such as improving the desired properties of the polypeptide or may confer one or more additional desired properties to the polypeptide. As already set out above, a preferred additional polypeptide domain will increase the half-life of the polypeptide, such as a (human) serum albumin binding domain, such as the Alb11 domain.

Thus, according to a further embodiment, the invention specifically includes polypeptides comprising any of the following sequences, wherein the exact amino acid sequences can be taken from Table III below:

SEQ ID NO:25 (=sequence of polypeptide F013500575),
SEQ ID NO:26 (=sequence of polypeptide F013500571),
and
SEQ ID NO:27 (=sequence of polypeptide F013500720.

According to an even more specific embodiment, the polypeptides of the invention are selected from the following group of molecules:

Polypeptide F013500575, having the sequence SEQ ID NO:25,
Polypeptide F013500571, having the sequence SEQ ID NO:26, and
Polypeptide F013500720, having the sequence SEQ ID NO:27.

TABLE III

Sequences of three specific embodiments of polypeptides of the invention

| ID SEQ ID NO: | Amino Acid Sequence (CDR sequences underlined) |
|---|---|
| F013500575 SEQ ID NO: 25 | AVQLVESGGGLVQPGGSLRLSCAASGRTFSTYTVGW FRQAPGKEREFVAAIRRGSSTYYADSVKGRFTISR DNSKNTVYLQMNSLRPEDTAVYYCAADTRTVALLQY RYDYWGQGTLVTVSSGGGGSGGGGSGGGGSGGGGSG GGGSGGGGSGGGGSEVQLVESGGGLVQPGNSLRLSC AASGFTFSSFGMSWVRQAPGKGLEWVSSISGSGSDT LYADSVKGRFTISRDNAKTTLYLQMNSLRPEDTAVY YCTIGGSLSRSSQGTLVTVSSGGGGSGGGGSGGGGS GGGGSGGGGSGGGGSGGGGSEVQLVESGGGLVQPGG SLRLSCAASGRTFSSYAMGWFRQAPGKEREFVAAIS WSGGSTYYADSVKGRFTISRDNSKNTVYLQMNSLRP EDTAVYYCAASPIPYGSLLRRRNNYDYWGQGTLVTV SSA |
| F013500571 SEQ ID NO: 26 | AVQLVESGGGLVQPGGSLRLSCAASGGTFSSYAMGW FRQAPGKEREFVAAIRRSGRRTYYADSVKGRFTISR DNSKNTVYLQMNSLRPEDTAVYYCAAARRVRSSTRY NTGTWWWEYWGQGTLVTVSSGGGGSGGGGSGGGGSG GGGSGGGGSGGGGSGGGGSEVQLVESGGGLVQPGNS LRLSCAASGFTFSSFGMSWVRQAPGKGLEWVSSISG SGSDTLYADSVKGRFTISRDNAKTTLYLQMNSLRPE DTAVYYCTIGGSLSRSSQGTLVTVSSGGGGSGGGGS GGGGSGGGGSGGGGSGGGGSGGGGSEVQLVESGGGL VQPGGSLRLSCAASGGTFSSYAMGWFRQAPGKEREF VAAISWRSGSTYYADSVKGRFTISRDNSKNTVYLQM NSLRPEDTAVYYCAADPRGYGVAYVSAYYEYWGQGT LVTVSSA |
| F013500720 SEQ ID NO: 27 | AVQLVESGGGLVQPGGSLRLSCAASGLTFSRYTMGW FRQAPGKEREFVAAIVRSGGSTYYADSVKGRFTISR DNSKNTVYLQMNSLRPEDTAVYYCAADRRGRGENYI LLYSSGRYEYWGQGTLVTVSSGGGGSGGGGSGGGGS GGGGSGGGGSGGGGSGGGGSEVQLVESGGGLVQPGN SLRLSCAASGFTFSSFGMSWVRQAPGKGLEWVSSIS GSGSDTLYADSVKGRFTISRDNAKTTLYLQMNSLRP EDTAVYYCTIGGSLSRSSQGTLVTVSSGGGGSGGGG SGGGGSGGGGSGGGGSGGGGSGGGGSEVQLVESGGG LVQPGGSLRLSCAASGGTFSSYAMGWFRQAPGKERE FVAAISWRSGSTYYADSVKGRFTISRDNSKNTVYLQ MNSLRPEDTAVYYCAADPRGYGVAYVSAYYEYWGQG TLVTVSSA |

As explained before, unless indicated otherwise, the polypeptides of the invention may include further moieties and/or additional polypeptide domains, as long as their binding to LRP5/LRP6 will not be prevented by such additional moiety or domain.

The polypeptides of the invention can additionally contain modifications such as glycosyl residues or modified amino acid side chains, and they may be PEGylated in order to increase half-life and other properties of such molecule. Techniques and reagents useful for PEGylating biparatopic immunoglobulin single variable domain constructs may be taken e.g. from WO2011/107507.

The polypeptides of the invention may have a modified N-terminal sequence, e.g. a deletion of one or more of the N-terminal amino acids, or an exchange of e.g. the first, N-terminal amino acid (e.g. glutamate to alanine), to optimize the molecule for being expressed by using certain expression systems (such as specific vectors or host cells), or for being expressed as inclusion bodies or in soluble form, or for being secreted into the medium or the periplasmic space or for being contained within the cell, or for yielding a more homogenous product. The polypeptides of the invention may have a modified C-terminal sequence, such as an additional alanine (as shown for the three embodiments shown in Table III above), and/or further amino acid exchanges in the C-terminal part or at other defined positions within any of the framework regions, as explained e.g. in WO2012/175741, WO2011/075861, or WO2013/024059, in order to e.g. further enhance stability or reduce immunogenicity of such polypeptides.

Furthermore, half-life of the polypeptides of the invention may be enhanced by adding an albumin domain, i.e. by converting them into albumin fusion proteins. Examples of useful albumin moieties, and how to add them to binding molecules, are e.g. provided in WO2001/079271 and WO2003/059934.

Preferably, the polypeptides of the invention are having binding ($EC_{50}$) values, measured in a FACS binding assay as described in Example 7.1 below, in the range of $10^{-6}$ moles/liter or less, more preferably $10^{-9}$ moles/liter or less, and even more preferably in the range of from $10^{-10}$ to $10^{-13}$ moles/liter, or are having an $IC_{50}$ value as measured in a combined Wnt1 and Wnt3a reporter assay as set out in Example 7.3 below, of $10^{-9}$ moles/liter or below, and preferably in the range of from $5\times10^{-10}$ moles/liter to $10^{-12}$ moles/liter.

The polypeptides of the invention allow a more efficient treatment of several cancer types, such as TNBC, CRC, and NSCLC. They are having improved in vitro characteristics (i.e. higher efficacy of Wnt pathway inhibition), cf. e.g. Examples 7 and 8 below, and significant in vivo tumor growth inhibition properties, leading to higher in vivo efficacy as compared to other LRP6 binding molecules described in the art, as shown in e.g. Examples 9 and 10 below.

In particular, as shown in vivo in a Wnt driven tumor model, the LRP5/LRP6 cross-reactive half-life extended biparatopic humanized VHH constructs could inhibit Wnt signaling and tumor growth in vivo, and even provided for substantial tumor shrinkage (i.e. tumor growth inhibition higher than 100%), which could not be achieved, under the same experimental settings, with a LRP6 binder known in the art. Tumor shrinkage (i.e. tumor regression) is of course the desired therapeutic effect (i.e. efficacy) for treatment of cancer patients. Furthermore, tumor regression, resulting in pathological complete response (pCR), is an acknowledged clinical endpoint, indicating significant improvement of progression free survival and overall survival.

In the same in vivo experiments, no significant body weight changes were observed (<10%), and results from gastrointestinal histopathological analyses did not indicate any toxic effects of the above polypeptides of the invention. This is specifically surprising in view of the in vivo DKK1 expression studies discussed above (i.e. resulting in intestinal mucosa ulceration and body weight loss).

Thus, the polypeptides of the invention are in fact providing for novel therapeutic options for the treatment of cancer diseases, and especially even for use in high unmet medical need indications such as (triple negative) breast cancer.

Surprisingly, the inventors arrived at this solution not by going the conventional route, i.e. trying to develop inhibitors or binding molecules having a high specificity/selectivity for one given target, such as LRP6 (mentioned as a target for the treatment of "Wnt signaling mediated diseases" e.g. in WO2009/056634). In contrast thereto, the inventors developed molecules targeting two related proteins at the same time—LRP6 and LRP5—and thereby achieved the above significantly improved in vitro and in vivo effects which could not be expected from the prior art.

The underlying molecular mechanism for this superiority is not fully clear, but it may be speculated—without wishing to be bound to a specific theory—that such cross-reactive molecules may have additional, and thereby stronger, effects on the highly complicated signaling cascade of the Wnt signaling pathway.

The above advantageous effects will further be illustrated in the Examples below and by way of the comparative data included therein.

Moreover, the polypeptides of the invention are easy to manufacture and are more soluble, which means that they may be stored and/or administered in higher concentrations compared to conventional antibodies. They are stable at room temperature and have prolonged stability even at extremes of pH, so that they may be prepared, stored and/or transported without the use of refrigeration equipment, conveying cost, time and environmental savings. Due to the above and due to their low immunogenicity, they furthermore offer a variety of options regarding administration routes other than injection and infusion, as well as regarding administration regimens and uses of specific devices.

Nucleic Acids, Vectors, Host Cells

According to further aspects, the invention relates to nucleic acid molecules and expression vectors encoding the polypeptides of the invention, as well as to host cells expressing the same. These nucleic acids, vectors, and host cells are useful for manufacturing the polypeptides of the invention, and further aspects and embodiments thereof will be described further below in connection with an outline of methods of manufacturing the polypeptides of the invention.

Therapeutic Use

Due to their biological properties, the polypeptides of the invention are suitable for treating diseases characterised by excessive or abnormal cell proliferation, such as cancer and idiopathic pulmonary fibrosis (IPF).

For example, the following cancers, tumors, and other proliferative diseases may be treated with polypeptides according to the invention, without being restricted thereto:

Cancers of the head and neck; Cancers of the lung, such as e.g. non-small cell lung cancer (NSCLC) and small cell lung cancer (SCLC); Neoplasms of the mediastinum, such as e.g. neurogenic tumors and mesenchymal tumors; Cancers of the gastrointestinal (GI) tract, such as e.g. cancers of the esophagus, stomach (gastric cancer), pancreas, liver and biliary tree (including e.g. hepatocellular carcinoma (HCC)), and the small and large intestine (including e.g. colorectal cancer); Cancers of the prostate; Cancers of the testis; Gynecologic cancers, such as e.g. cancers of the ovary; Cancers of the breast, such as e.g. mammary carcinoma, hormone receptor positive breast cancer, Her2 positive breast cancer, and triple negative breast cancer; Cancers of the endocrine system; Sarcomas of the soft tissues, such as e.g. fibrosarcoma, rhabdomyosarcoma, angiosarcoma, Kaposi's sarcoma; Sarcomas of the bone, such as e.g.

myeloma, osteosarcoma, Ewing's tumor, fibrosarcoma, osteochondroma, osteoblastoma, and chondroblastoma; Mesotheliomas; Cancers of the skin, such as e.g. basal cell carcinoma, squamous cell carcinoma, Merkel's cell carcinoma, and melanoma; Neoplasms of the central nervous system and brain, such as e.g. astrocytoma, glioblastoma, gliomas neuroblastomas, and retinoblastomas; Lymphomas and leukemias such as e.g. B-cell non-Hodgkin lymphomas (NHL), T-cell non-Hodgkin lymphomas, chronic B-cell lymphocytic leukemia (B-CLL), chronic T-cell lymphocytic leukemia (T-CLL), Hodgkin's disease (HD), large granular lymphocyte leukemia (LGL), chronic myelogenous leukemia (CML), acute myelogenous/myeloid leukemia (AML), acute lymphatic/lymphoblastic leukemia (ALL), multiple myeloma (MM), plasmacytoma, and myelodysplastic syndromes (MDS); and cancers of unknown primary site.

All cancers, tumors, neoplasms, etc., mentioned above which are characterized by their specific location/origin in the body are meant to include both the primary tumors and the metastatic tumors derived therefrom.

More specifically, the polypeptides of the invention are useful for the treatment of diseases, and esp. cancer diseases in which abnormal cell proliferation is caused by, or involves, abnormal (activated) Wnt signaling.

Thus, the polypeptides of the invention are specifically useful for the treatment of solid tumors, and more specifically for the treatment of lung, liver, colon, brain, thyroid, pancreas, breast, ovary and prostate cancers, and even more specifically for the treatment of non-small cell lung cancer (NSCLC), triple-negative breast cancer (TNBC), and colorectal cancer (CRC). In particular, the polypeptides of the invention may be used to treat patients with locally advanced or metastatic TNBC, patients with metastatic NSCLC or locally advanced or metastatic CRC, as single agent or in combination, to prolong progression free survival (PFS) and overall survival (OS). Furthermore, the polypeptides of the invention may be used as neoadjuvant treatment for breast cancer patients to achieve pathological complete response (pCR; defined as the absence of residual invasive and in situ cancer by histo-pathological evaluation of the complete resected breast specimen and all sampled regional lymph nodes following completion of neoadjuvant systemic therapy).

The polypeptides of the invention may be used in therapeutic regimens in the context of first line, second line, or any further line treatments.

The polypeptides of the invention may be used for the prevention, short-term or long-term treatment of the above-mentioned diseases, optionally also in combination with radiotherapy and/or surgery.

Likewise, the polypeptides of the invention are specifically useful for the treatment of other diseases caused by abnormal cell proliferation involving the Wnt signaling pathway, such as idiopathic pulmonary fibrosis (IPF) (Königshoff et al. "Functional Wnt signaling is increased in idiopathic pulmonary fibrosis". *PLoS One* 2008; 3(5):e2142; Lam et al. "Wnt coreceptor Lrp5 is a driver of idiopathic pulmonary fibrosis". *Am J Respir Crit Care Med.* 2014; 190(2):185-95).

Furthermore, the polypeptides of the invention are specifically useful for the treatment of retinopathies, and esp. for the treatment of diabetic retinopathy, due to abnormal Wnt activation in the inner retina cells, causing the increase in abnormal new retinal vessel formation leading to development and progression of diabetic retinopathy (Chen, Y., et al. "Activation of the Wnt pathway plays a pathogenic role in diabetic retinopathy in humans and animal models" *The Am J Pathol.* 2009; 175(6):2676-85., Gao et al. "Elevated LRP6 levels correlate with vascular endothelial growth factor in the vitreous of proliferative diabetic retinopathy" *Mol Vis.* 2015; 21:665-72).

Finally, as it could be shown that inhibition of Wnt1/Wnt3a signaling pathways can also have an effect on dendritic cells (DCs) and dendritic cell function, the polypeptides of the invention may also be useful in the treatment of immunologic and infectious diseases, as well as for influencing the tumor microenvironment in the various cancer diseases already set out above. Tumors actively suppress antitumor immunity, and DCs play an important role in the cancer immunoescape mechanism. In particular, studies have shown that Wnt ligands in the tumor microenvironment can also initiate paracrine signaling within the immune cells and regulate host antitumor immunity (Hong et al. "beta-catenin promotes regulatory T-cell responses in tumors by inducing vitamin A metabolism in dendritic cells". *Cancer Res.* 2015; 75(4):656-65).

Of course, the above also includes the use of the polypeptides of the invention in various methods of treating the above diseases by administering a therapeutically effective dose to a patient in need thereof, as well as the use of these polypeptides for the manufacture of medicaments for the treatment of such diseases, as well as pharmaceutical compositions including such polypeptides of the inventions, as well as the preparation and/or manufacture of medicaments including such polypeptides of the invention, and the like.

Combinations with Other Active Substances

The polypeptides of the invention may be used on their own or in combination with other pharmacologically active substances, such as state-of-the-art or standard-of-care compounds, such as e.g. cytostatic or cytotoxic substances, cell proliferation inhibitors, anti-angiogenic substances, steroids, immune modulators/checkpoint inhibitors, and the like.

Cytostatic and/or cytotoxic active substances which may be administered in combination with the compounds according to the invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF)), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors, tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, Aurora kinase inhibitors), tyrosine kinase inhibitors (e.g. PTK2/FAK inhibitors), protein protein interaction inhibitors, MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab), cancer vaccines such as traditional tumor vaccine (cell based vaccines, e.g. Sipuleucel-T for treatment of prostate cancer), personalized neoantigen vaccines, and oncolytic viruses, and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Particularly preferred are methods of treatment including the use of the polypeptides of the invention in combination with a drug selected from the group consisting of:
(i) anti-VEGF antibodies (bevacizumab and other anti-angiogenic substances) with or without chemotherapy combination (including doxorubicin/cyclophosphamide combination and/or capecitabine/docetaxel combination in neoadjuvant setting; taxane/platinum regimen for first and later line treatment) in breast cancer patients;
(ii) EGFR TKIs for EGFR mutant NSCLC or crizotinib for ALK translocated NSCLC with or without chemotherapy combination (platinum based cytotoxic combination therapy, including gemcitabine/cisplatin in first line treatment; docetaxel or pemetrexed in second line treatment in lung cancer patients;
(iii) anti-EGFR antibodies (cetuximab and panitumumab in KRASwild-type tumors) with or without chemotherapy combination (including irinotecan), anti-VEGF antibody combination (bevacizumab and other anti-angiogenic substances) or regorafenib combination, e.g. for the treatment of CRC patients.
(iv) immunotherapeutic agents, including anti-PD-1 agents, such as pembrolizumab and nivolumab, anti-PD-L1 agents, anti-CTLA4 agents, anti-BTLA agents, anti-LAG3 agents, and anti-TIM3 agents, such as anti-PDL1 antibodies etc., e.g. for treatment of breast cancer, lung cancer and CRC patients
(v) chemotherapeutic agents, such as platinium-based antineoplastic agents, or in a combination with a FOLFOX chemotherapy regimen, including folinic acid, 5'-fluorouracil, and oxaliplatin, or in a combination with a FOLFOXIRI chemotherapy regimen, including folinic acid, 5'-fluorouracil, oxaliplatin, and irinotecan, e.g. for treatment of breast cancer or CRC patients.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation, and methods of preparing, the polypeptides of the invention for the combined use with the above combination partners. Also included are the preparation, and methods of preparing, the above-mentioned combination partners for the combined use with the polypeptides of the invention. Thus, the invention hereby e.g. provides methods of using, or preparing for use, an immune modulator/checkpoint inhibitor, such as an anti-PD1 antibody, such as pembrolizumab or nivolumab, for the administration in combination with a polypeptide of the invention, and more specifically for the administration in a combination therapy regimen with a polypeptide of the invention.

Furthermore, the invention also encompasses kits comprising at least one polypeptide of the invention and one or more other components selected from the group consisting of other drugs used for the treatment of the diseases and disorders as described above, and devices as described below.

Pharmaceutical Compositions, Methods of Administration, Dosages

It will be clear to the skilled person that the above methods of treatment of a disease include the preparation of a medicament for the treatment of said disease. Thus, the invention further relates to pharmaceutical compositions for the treatment of the diseases mentioned hereinabove, wherein such compositions comprise at least one polypeptide of the invention.

The polypeptides of the invention and/or the compositions comprising the same can be administered to a patient in need thereof in any suitable manner, depending on the specific pharmaceutical formulation or composition to be used. Thus, the polypeptides of the invention and/or the compositions comprising the same can for example be administered intravenously (i.v.), subcutaneously (s.c.), intramuscularly (i.m.), intraperitoneally (i.p.), transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, or any other suitable manner in an effective amount or dose.

The polypeptides of the invention and/or the compositions comprising the same are administered according to a regimen of treatment that is suitable for treating and/or alleviating the disease, disorder or condition to be treated or alleviated. The clinician will generally be able to determine a suitable treatment regimen, depending on factors such as the disease, disorder or condition to be treated or alleviated, the severity of the disease, the severity of the symptoms thereof, the specific polypeptide of the invention to be used, the specific route of administration and pharmaceutical formulation or composition to be used, the age, gender, weight, diet, general condition of the patient, and similar factors well known to the clinician. Generally, the treatment regimen will comprise the administration of one or more polypeptides of the invention, or of one or more compositions comprising the same, in therapeutically effective amounts or doses.

Generally, for the treatment and/or alleviation of the diseases, disorders and conditions mentioned herein and depending on the specific disease, disorder or condition to be treated, the potency of the specific polypeptide of the invention to be used, the specific route of administration and the specific pharmaceutical formulation or composition used, the polypeptides of the invention will generally be administered in an amount between 0.005 and 20.0 mg per kilogram of body weight and dose, preferably between 0.05 and 10.0 mg/kg/dose, and more preferably between 0.5 and 10 mg/kg/dose, either continuously (e.g. by infusion) or more preferably as single doses (such as e.g. twice a week, weekly, or monthly doses; cf. below), but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

Depending on the specific polypeptide of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The efficacy of the polypeptides of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

Preferably, the polypeptides of the invention are having better characteristics than conventional antibodies known in the art (such as the LRP6 binders described in the "Background of the Invention" section above) in at least one of these assays or models, and preferably in one or more of the in vivo models.

Formulations

For pharmaceutical use, the polypeptides of the invention may be formulated as a pharmaceutical preparation comprising (i) at least one polypeptide of the invention and (ii) at least one pharmaceutically acceptable carrier, diluent, excipient, adjuvant, and/or stabilizer, and (iii) optionally one or more further pharmacologically active polypeptides and/or compounds. By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, $18^{th}$ Ed., Mack Publishing Company, USA (1990). For example, the polypeptides of the invention may be formulated and administered in any manner known per se for conventional antibodies and antibody fragments and other pharmaceutically active proteins. Thus, according to a further embodiment, the invention relates to a pharmaceutical composition or preparation that contains at least one polypeptide of the invention and at least one pharmaceutically acceptable carrier, diluent, excipient, adjuvant and/or stabilizer, and optionally one or more further pharmacologically active substances.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the polypeptides of the invention may also contain a preservative to prevent the growth of microorganisms, such as antibacterial and antifungal agents, for example, p-hydroxybenzoates, parabens, chlorobutanol, phenol, sorbic acid, thiomersal, (alkali metal salts of) ethylenediamine tetraacetic acid, and the like. In many cases, it will be preferable to include isotonic agents, for example, sugars, buffers or sodium chloride. Optionally, emulsifiers and/or dispersants may be used. The proper fluidity can be maintained, for example, by the formation of liposomes, by the maintenance of the required particle size in the case of dispersions or by the use of surfactants. Other agents delaying absorption, for example, aluminum monostearate and gelatin, may also be added. The solutions may be filled into injection vials, ampoules, infusion bottles, and the like.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the polypeptides of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml (i.v. administration) or 100 mg/ml (s.c. administration) and an aqueous buffer such as:

phosphate buffered saline, pH 7.4,
other phosphate buffers, pH 6.2 to 8.2,
acetate buffers, pH 3.2 to 7.5, preferably pH 4.8 to 5.5
histidine buffers, pH 5.5 to 7.0,
succinate buffers, pH 3.2 to 6.6, and
citrate buffers, pH 2.1 to 6.2,
and, optionally, salts (e.g. NaCl) and/or sugars (such as e.g. sucrose and trehalose) and/or other polyalcohols (such as e.g. mannitol and glycerol) for providing isotonicity of the solution.

Preferred buffered protein solutions are solutions including about 0.05 mg/ml of the polypeptide of the invention dissolved in 25 mM phosphate buffer, pH 6.5, adjusted to isotonicity by adding 220 mM trehalose. In addition, other agents such as a detergent, e.g. 0.02% TWEEN® 20 or TWEEN® 80 surfactant, may be included in such solutions. Formulations for subcutaneous application may include significantly higher concentrations of the polypeptide of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure.

Also, compared to conventional antibodies or antibody fragments, one major advantage of the use of the polypeptides of the invention is that they can also be easily administered via routes other than parenteral administration and can be easily formulated for such administration. For example, as described in international patent application WO2004/041867, such polypeptides may be formulated for oral, intranasal, intrapulmonary and transdermal administration.

According to a further aspect of the invention, a polypeptide of the invention may be used in combination with a device useful for the administration of the polypeptide, such as a syringe, injector pen, micropump, or other device.

Methods of Manufacture and Purification

The invention further provides methods of manufacturing a polypeptide of the invention, such methods generally comprising the steps of:
culturing host cells comprising a nucleic acid encoding a polypeptide of the invention (hereinafter: "nucleic acid of the invention") under conditions that allow expression of the polypeptide of the invention; and,
recovering or isolating the polypeptide expressed by the host cells from the culture; and
optionally further purifying and/or modifying and/or formulating the polypeptide of the invention.

A nucleic acid of the invention can e.g. be a DNA molecule comprising coding sequences as well as regulatory sequences and optionally natural or artificial introns, or can be a cDNA molecule. It may have its original codons or may have an optimized codon usage that has been specifically adapted for expression in the intended host cell or host organism. According to one embodiment of the invention, the nucleic acid of the invention is in essentially isolated form, as defined above.

The nucleic acid of the invention may also be in the form of, be present in and/or be part of a vector, such as for example a plasmid, cosmid or YAC, which again may be in essentially isolated form. The vector may especially be an expression vector, i.e. a vector that can provide for expression of the polypeptide in vitro or in vivo (e.g. in a suitable host cell, host organism and/or expression system). Such expression vector generally comprises at least one nucleic acid of the invention that is operably linked to one or more suitable regulatory element(s), such as promoter(s), enhancer(s), terminator(s), and the like. Specific examples of such regulatory elements and other elements, such as integration factor(s), selection marker(s), signal or leader sequence(s), reporter gene(s), and the like, useful or necessary for expressing polypeptides of the invention, are disclosed e.g. on pp. 131 to 133 of WO2006/040153.

The nucleic acids of the invention can be prepared or obtained in a manner known per se (e.g. by automated DNA synthesis and/or recombinant DNA technology), based on the information on the amino acid sequences for the polypeptides of the invention given herein.

According to another embodiment, the invention relates to a host or host cell that expresses or is capable of expressing a polypeptide of the invention; and/or that contains a nucleic acid encoding a polypeptide of the invention. According to a particularly preferred embodiment, said host cells are bacterial cells, yeast cells, fungal cells or mammalian cells.

For production on industrial scale, preferred heterologous hosts for the (industrial) production of immunoglobulin single variable domain polypeptides and protein therapeutics containing them include strains of *E. coli, Pichia pastoris*, and *S. cerevisiae* that are suitable for large scale expression, production and fermentation, and in particular for large scale (bio-)pharmaceutical expression, production and fermentation.

Polypeptides of the invention produced in a cell as set out above can be produced either intracellularly (e.g. in the cytosol, in the periplasma or in inclusion bodies) and can then be isolated from the host cells and optionally be further purified; or they can be produced extracellularly (secreted into the medium in which the host cells are cultured) and then isolated from the culture medium and optionally further purified.

Further methods and reagents used for the recombinant production of polypeptides, such as suitable expression vectors, transformation or transfection methods, selection markers, methods of induction of protein expression, culture conditions, and the like, are known in the art. Similarly, protein isolation and purification techniques useful in a method of manufacture of a polypeptide of the invention are well known to the skilled person.

Production of the polypeptides of the invention through fermentation in convenient recombinant host organisms such as *E. coli* and yeast is cost-effective, as compared to conventional antibodies which usually require expensive mammalian cell culture facilities. Furthermore, achievable levels of expression are high and yields of the polypeptides of the invention are in the range of 1 to 10 g/l (*E. coli*) and up to 10 g/l (yeast) and more.

EXAMPLES

Example 1: Immunization of Llamas with LRP5 and LRP6 for the Induction of Humoral Immune Responses Several protocols for the immunization of llamas needed to be worked out and implemented for identification of LRP5/LRP6 cross-reactive binding VHH domains: Llamas were initially immunized with recombinant extracellular domains of LRP6 and LRP5 proteins (human and mouse). However, functional characterization of the above mentioned LRP5 recombinant protein revealed that only the Wnt1 class binding epitope was properly folded. In contrast, there was no indication for proper folding of the LRP5-Wnt3a class binding domain. Thus, further work was required to develop suitable antigens for immunization. As a work-around, llamas were immunized with HEK293 cells stably transfected with human LRP5 or human LRP6. However, also then, only very low expression of human LRP5 could be achieved, by transient or by stable transfection, and using different cell lines (HEK293, CHO and NIH-3T3 cells). Thus, even further work was required to achieve sufficient expression of LRP5. In the end, and after some unsuccessful trial and error, this could be achieved by developing a protocol involving stable co-transfection of HEK293 cells with MesDC-2, a chaperone intended to increase exogenous LRP5 expression. Even then, i.e. upon co-expression of MesDC-2 during the generation of the LRP5 stable transfected cell line, instability of protein expression was repeatedly observed. This resulted in the problem that LRP5 expression could be lost during immunization and selection. To solve this further problem, passaging of the cells expressing LRP5 was limited as much as possible and additional cell sorting was performed to enrich for cells expressing LRP5.

Llamas were additionally immunized with LRP5-coding DNA and LRP6-coding DNA with and without the hMesDC-2 chaperone in opposite flanks. Additional boosts were delivered to several llamas in an attempt to enhance the cross-reactive immune response, with the objective to increase chances of identifying LRP5/LRP6 cross-reactive VHH domains.

Immune blood (PBL) samples were taken at regular intervals, serum responses were determined, and total RNA was prepared from the isolated PBL. Medium serum responses to LRP6 were observed, in contrast to low serum responses to LRP5 upon immunization with recombinant protein. A medium LRP5 immune response was observed for llamas immunized with DNA. In contrast, very low immune response was observed for the cell immunizations. Additionally, synthetic libraries were also explored. Nevertheless, finally, sufficient diversity of the repertoire could be achieved for continuing with the next steps, as outlined in Example 2.

Example 2: Isolation of LRP5 and LRP6 Binding Monovalent VHH Domains (VHHs)

Library Construction:

Total RNA was extracted immediately following collection of the immune tissues, and RNA integrity and concentration was verified. cDNA samples were made from these RNA preparations. Nucleotide sequences encoding VHHs were amplified from the cDNA samples in a one-step RT-PCR reaction. The 700 bp amplicons specifically amplified from the IgG2 and IgG3 cDNAs in the sample were isolated from agarose gel and subsequently used as template in a nested PCR reaction. The PCR products were subsequently digested with SfiI and BstEII and ligated into the corresponding restriction sites of phagemid vector pAX50. The ligation mixtures were electroporated into Escherichia coli TG-1. The resulting pool of transformants constituted the genetic diversity of the phage display library.

pAX50 is an expression vector derived from pUC119, which contains a resistance gene for ampicillin and the lac promoter followed by the coding sequence of the pIII protein signal peptide in frame with a downstream VHH domain cloning site. In frame with the VHH domain coding sequence, the vector codes for a C-terminal Myc and hexa-histidine tag (SEQ ID NO: 59) and a coli phage pIII protein.

After infection of the E. coli TG-1 library clones with helper phage, the presence of pAX50 allows for production of phage particles from these clones, displaying the individual VHH domains as a fusion protein with the pIII protein.

Selection:

The VHH domain-phagemid libraries were constructed and used for selections. Given the very high species homology across species (between llama and human LRP5 and LRP6), it was uncertain whether the immune response raised in the llamas would raise sufficient diversity of the VHH domains. Therefore, two synthetic libraries were used in parallel with the immune libraries during selections.

Different strategies were used during selections as follows:

Alternation of LRP5 and LRP6 derived tools to enhance chances of identifying LRP5/LRP6 cross-reactive VHH domains, e.g. selections on libraries from LRP5 immunized llamas with LRP6 derived proteins or the use of both LRP5 and LRP6 proteins during selection on synthetic libraries.

Alternation of species source to select for human/mouse LRP5/LRP6 cross-reactive VHH domains (mouse cross-reactivity of such LRP5 and LRP6 antagonist allowing to evaluate efficacy, i.e. tumor growth inhibition, and safety profiles, required for assessment of the therapeutic window, in the same pre-clinical models (i.e. in xenograft tumor-mouse models)).

"In solution" selections with recombinant proteins to keep the epitopes in their native conformation: As an additional obstacle, LRP5 and LRP6 recombinant proteins were found to lose their proper folding if directly coated on ELISA binding plates. Therefore, the recombinant proteins were biotinylated and, after confirming proper folding in functional assays, were used for selection "in solution".

Selections using cells overexpressing LRP5 or LRP6, to have native conformation of the receptors. This surprisingly turned out to be an important ruse, especially needed to improve selection of binders to the Wnt3a-class binding domain of LRP5, since functional data of recombinant protein showed lack of proper folding of the Wnt3a binding epitope.

Example 3: Screening of the Monovalent VHHs

After selection, clones were grown in 96 deep well plates (1 mL volume), and VHH expression was induced by adding IPTG. Periplasmic extracts of single clones were prepared according to standard methods, as e.g. reported in WO2011/107507, and screened for binding to human LRP6 and LRP5. Initially, the periplasmic extracts were screened in binding ELISA assays using recombinant LRP5 and LRP6, which represent sensitive, robust and high-throughput assays, when compared to FACS-based binding assays. After purification, VHHs identified in ELISA assays were further characterized using binding FACS assay to confirm binding of purified VHHs to the LRP5 and LRP6 receptors in their native conformation.

Figure 2:
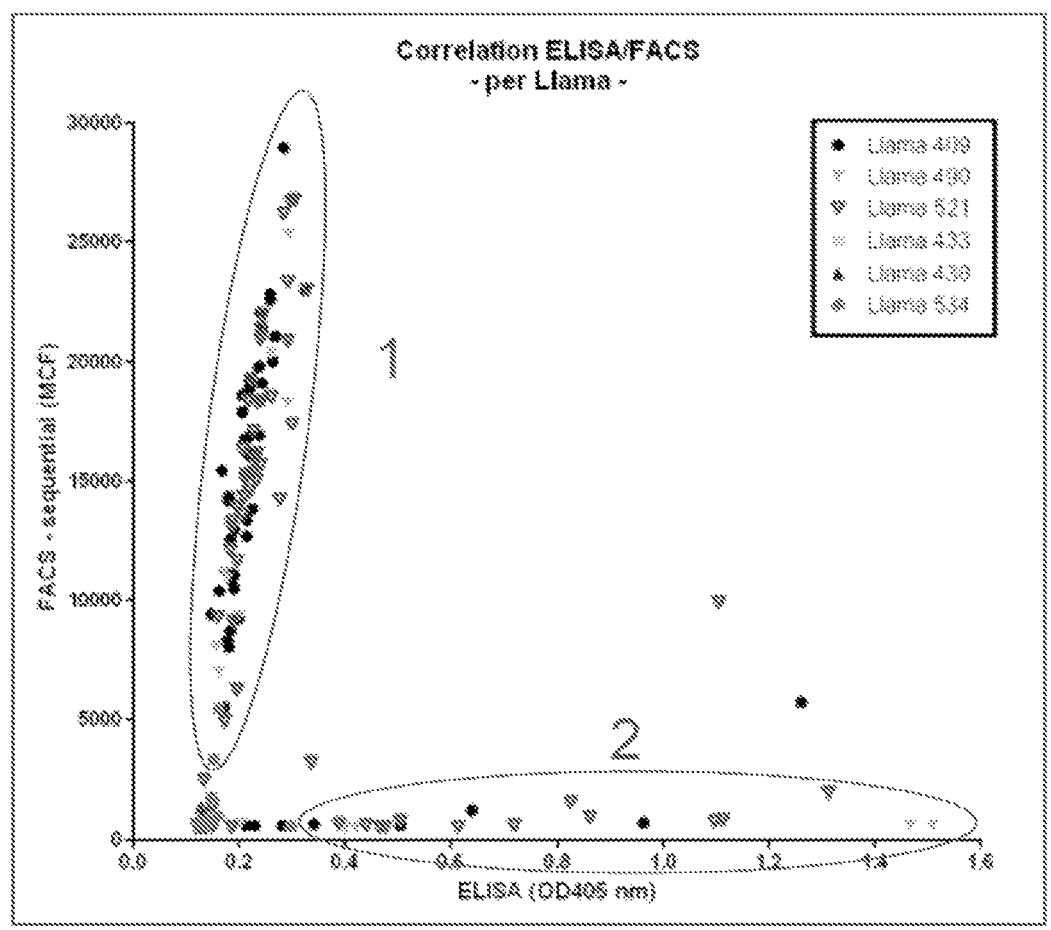
FIG. 2 shows the lack of correlation between binding FACS and ELISA assays for a representative number of LRP6 binding VHHs derived from the llama immunization. The number "1" panel of VHHs is characterized by high affinity to cells expressing LRP6 on the plasma membrane, as detected by FACS binding assays (on the y axis MCF values are reported). The number "2" panel of VHHs is characterized by high affinity to recombinant human LRP6 ectodomain (rhLRP6-Fc), as detected by ELISA binding assays (on the x axis OD405 values are reported).

Usually, a good correlation between ELISA and FACS binding assays is expected. However, in the present case, the best LRP5 and LRP6 binding VHHs in ELISA assays (i.e. with high affinity to recombinant LRP5 or LRP6 ectodomain) did not show any binding or very weak binding to human LRP5 and LRP6 in a FACS binding assay, as shown in FIG. 2 for the panel "2" binders. The use of different coating buffers (dPBS vs. bicarbonate buffer) and blocking solutions in the ELISA set-up (Marvel vs. BSA) did not resolve the observed discrepancy. Instead, it was found out that very weak binders in ELISA showed high affinity to LRP5 and LRP6 in binding FACS assays using LRP5 and LRP6 expressing cells, as shown in FIG. 2 for the panel "1" binders. These further data and experiments thus allowed for selection of high affinity binders recognizing the native conformation of the two receptors. Additionally, confirmation was thereby obtained that these high affinity binders are recognizing a conformation dependent epitope, and not a linear epitope in LRP5 and LRP6 proteins. These further non-routine data and experiments thus allowed for selection of therapeutically relevant LRP5 and LRP6 binders, which should have high affinity towards LRP5 and LRP6 expressed on the plasma membrane in their native conformation.

Thus, despite (i) the low throughput of FACS binding assays, (ii) the less robust assay set-up, and (iii) the above-described difficulties encountered due to the loss of recombinant protein expression upon passaging of the cells overexpressing LRP5, these assays were subsequently used for further selection and characterization of high affinity VHH binders. Briefly, cells were incubated with purified VHH dilutions (1:5 serial dilutions from 1 µM to 1 pM, final concentration) for 1.5 hours at 4° C. on a plate shaker. After washing the cells 5× with FACS buffer, consisting of 1× phosphate buffered saline (PBS)+10% fetal bovine serum (FBS)+0.05% sodium azide, they were incubated for 30 minute up to 1 hour at 4° C. with a polyclonal mouse antibody which binds to the framework regions of the VHHs and, therefore, binds to all the LRP5 and/or LRP6 binders tested. After washing the cells 3× with FACS buffer, the cells were incubated for 30 minutes up to 1 hour at 4° C. with the labeled secondary antibody (anti-mouse PE), followed by 3× washing step with FACS buffer. Fluorescence was measured using FACSARRAY™ bioanalyzer (BD).

A total of hundred LRP5/LRP6 cross-reactive VHHs families/clusters were identified from immune libraries and from synthetic origin, based on binding FACS data and sequence analysis. Representative examples thereof are shown, and defined by their sequence, further below. The VHHs were expressed in *E. coli* and purified. In case expression in *E. coli* proved insufficient, VHHs were produced in *Pichia pastoris*. A brief description of expression and purification of VHHs is reported further below.

Generic Expression of VHHs in *E. coli*:

The encoding sequences were cloned into the pAX100 expression vector and expressed in *E. coli* as c-Myc hexa-histidine-tagged proteins (SEQ ID NO: 59). *E. coli* TG-1 cells containing the VHH constructs of interest were grown (37° C., 250 rpm) in shake flasks in TB medium supplemented with kanamycin and induced by addition of 1 mM IPTG for expression. After spinning the cell cultures, periplasmic extracts were prepared by freeze-thawing the pellets and resuspending in dPBS.

Generic Expression of VHHs in *Pichia* (*P.*) *pastoris*:

The encoding sequences were cloned into the pAX159 expression vector and expressed in *P. pastoris* as c-Myc hexa-histidine-tagged (SEQ ID NO: 59) proteins. *P. pastoris* X-33 cells containing VHH constructs of interest were grown (30° C., 250 rpm) in BGCM (Buffered Glycerol-Complex Medium; Invitrogen). On the third day, the medium was switched to BMCM (Buffered Methanol-Complex Medium; Invitrogen) and the culture was grown further and was regularly induced by addition of 0.5 vol % methanol (100%). After spinning the cell culture, supernatant (containing the secreted VHH) was collected.

VHH Purification:

Hexa-histidine-tagged (SEQ ID NO: 59) VHHs were purified on the Freedom Tecan EVO®150 automated workstation by immobilised metal affinity chromatography (ROBOCOLUMNS™ 100 ul Nickel SEPHAROSE™ 6 FF, Atoll), eluted from the column with 250 mM imidazole and subsequently desalted towards dPBS. The purity and integrity of VHHs was verified by SDS-PAGE and/or western blot using anti-Myc and anti-VHH detection.

Example 4: In Vitro Characterization of Purified Monovalent VHHs

After VHH screening, the purified VHHs having high affinity to cells expressing LRP5 and LRP6 were characterized by using several functional and biophysical assays as described below:

4.1 LRP5 and LRP6 Binding Potency and Cross-Reactivity: FACS-Based DKK1 Competition Assay During characterization of LRP5/LRP6 cross-reactive monovalent VHHs, it was observed that data obtained in binding FACS assay did not always correlate with the potency observed in Wnt1 and Wnt3a reporter assays, most likely due to fast off-rate of some of the VHHs. Therefore, this additional assay needed to be established (i.e. a DKK1 competition FACS), which proved to be more reliable for selectivity and binding potency determination and comparison between LRP5 and LRP6 binding. The aim was to select functional VHHs which bind to LRP5 and LRP6 with a similar potency, in order to achieve blockade of both receptors at the same concentration. The identified Wnt1 and Wnt3a functional VHHs were thus characterized in DKK-1 competition FACS as follows:

For FACS-based DKK1 competition assay, HEK293 cells with stable overexpression of human LRP5 or human LRP6 were used. Human recombinant DKK1 (rhDKK1—R&D Systems, Cat 5439-DK/CF) was added to the cells at the constant final concentration of 1 nM. Cells were incubated with rhDKK1 and LRP5 and/or LRP6 binder dilutions (1:5 serial dilution of the purified VHHs) for 1.5 hours at 4° C. on a plate shaker. After washing the cells three times with FACS buffer, they were incubated with biotinylated goat anti-human DKK1 (R&D Systems, Cat BAF1096) for 30 minutes at 4° C. on a plate shaker. After washing the cells three times with FACS buffer, they were incubated with Streptavidin PE (BD Biosciences, Cat 554061) for 30 minute to 1 hour at 4° C. on a plate shaker in the dark. Cells were washed twice with FACS buffer and fluorescence was measured using FACS Array (BD) and MCF values were reported.

LRP5/LRP6 cross-reactive VHHs are expected to compete with human DKK1 for binding to HEK293 overexpressing human LRP5, as well as for binding to HEK293 overexpressing human LRP6. In contrast, an LRP5 specific VHH would compete with human DKK1 for binding to HEK293 cells overexpressing human LRP5 but not, or with very low potency (>200 nM) for binding to HEK293 cells overexpressing human LRP6 (and the same would apply, vice versa, to LRP6 specific VHHs). As a result of this experiment, it could be shown that the present LRP5/LRP6 cross-reactive VHHs competed with human DKK1 for binding to HEK293 cells overexpressing human LRP5, as well as to those overexpressing human LRP6 (i.e. decrease in MCF value with increasing concentration of the binder with complete inhibition of DKK1 binding corresponded to <60 MCF values at the highest concentration tested).

4.2 Species Cross-Reactivity: Mouse and Cynomolqus Monkey

To determine whether the selected panel of LRP5/LRP6 cross-reactive VHHs was able to bind to LRP5 and LRP6 of mouse and of cynomolgus monkey origin, DKK1 competition FACS was performed as follows:

Serial dilutions of VHHs were incubated with HEK293 cells stably expressing mouse LRP5, cyno LRP5, mouse LRP6, or cyno LRP6 in the presence of 1 and 0.3 nM hDKK1 (concentration below EC50 value of mouse and cyno, respectively). Binding of DKK1 to the cells was detected using a biotinylated anti-DKK1 antibody with Streptavidin-PE as secondary detection as described above. As a result, such cross-reactivity could be demonstrated.

4.3 Epitope Binning

Binning experiments were performed for the most potent Wnt1 signaling blocking LRP5/LRP6 cross-reactive VHHs, to identify different epitope bins. In particular, individual VHHs were analyzed for their ability to compete with other biotinylated VHHs (called reference VHHs) for LRP5 and LRP6 receptor binding using FACS based assays. Serial dilutions of the individual VHHs were incubated on HEK293 stably expressing human LRP5 or LRP6 together with 200 pM or 500 pM biotinylated reference VHH (concentrations below EC50 value). The binding of biotinylated reference VHH to the cells was detected using streptavidin-PE. A VHH competing with the reference VHHs for binding to LRP5 and LRP6 shows a decrease in the fluorescence measured using FACS Array.

As a result of these experiments, the Wnt1 blockers could be categorized into three bins. For the Wnt3a blockers, the lower affinity of the VHHs did not allow to perform epitope binning experiments.

4.4 Wnt1 and Wnt3a Reporter Assays

The ability of the LRP5/LRP6 cross-reactive VHHs to inhibit Wnt signaling was tested in functional Wnt1 and Wnt3a assays. Also in this regard, no established protocol could be used, but several attempts needed to be tried to establish biochemical functional assays, such as Wnt1/Wnt3a—LRP5/LRP6 blocking assays: In addition to the difficulties encountered with recombinant LRP5 and LRP6 proteins (see Example 1), a functional recombinant Wnt1 ligand (including commercially available) is not available. Wnt proteins contain many conserved cysteines and are modified by mono-unsaturated fatty acid (palmitoleic acid), attached to a conserved serine. These post-translational modifications are required for efficient signaling and for Wnt secretion. Structural analyses show that one of the domains, containing the palmitoleic acid lipid, is required for binding to the Frizzled receptors, leading to a conformational change that allows the interaction of the Wnt ligands with LRP5 and LRP6 on the cell surface. Thus, it turned out that such post-translational modification is required for functional studies involving this protein, but at the same time such lipid-based post-translational modifications render these proteins very difficult to express and purify (low solubility). Thus, this turned out to be a major hurdle for biochemical assays.

Thus, a cell based functional assay was developed for characterization of the purified VHHs: A Wnt beta-lactamase reporter gene assay. In particular for the Wnt1 pathway inhibition, CELLSENSOR™ LEF/TCF-bla FREE-SYTLE™ 293F cells (Invitrogen, Cat. K1677) were transfected with human Wnt1, and clones with stable overexpression of human Wnt1 were selected. For testing the Wnt3a pathway inhibition, CELLSENSOR™ LEF/TCF-bla FREESTYLE™ 293F cells with stable overexpression of human Wnt3a were generated. The CELLSENSOR™ LEF/TCF—bla FREESTYLE™ 293 cell line contains a beta-lactamase reporter gene under control of the Wnt inducible LEF/TCF promoter, which is stably integrated into FREESTYLE™ 293 cells (Invitrogen). The expression of Wnt1 or Wnt3a in these cells thus results in the constitutive expression and, therefore, enzymatic activity of the beta-lactamase. The treatment with LRP5/LRP6 cross-reactive functional VHHs is thus expected to lead to inhibition of Wnt1 and Wnt3a pathway leading to inhibition of beta-lactamase enzymatic activity.

For the assay, 1E06/ml cells with overexpression of Wnt1 or Wnt3a were seeded into a 384 well tissue culture plate and incubated overnight at 37° C. The following day, serial dilutions of various LRP5/LRP6 cross-reactive VHH solutions were prepared and added to the cells in the presence of LiCl at the final concentration of 10 nM. DKK1, as positive control, was added to the cells at the final concentration of 200 nM. DKK1 treatment resulted in a complete inhibition of Wnt1 and Wnt3a pathway, and therefore a complete inhibition of beta-lactamase enzymatic activity. The cells were incubated overnight at 37° C. The following day, beta-lactamase enzymatic activity was measured according to the manufacturer's instructions (Invitrogen, Cat K1085). For fluorescence emission, values at 460 nm and 530 nm were obtained using a standard fluorescence plate reader and the 460/530 nm emission ratios plotted for the indicated treatment. Efficacy was calculated against the positive control (DKK1; 200 nM final concentration).

A total of twelve LRP5/LRP6 cross-reactive Wnt1 blockers with full efficacy and potency better than 50 nM were selected. Fourteen cross-reactive Wnt3a blockers, mainly with low potencies, were identified. Only one Wnt3a blocker showed good potency (below 5 nM).

4.5 Wnt1 and Wnt3a Phosphorylation Assays

The most potent and efficacious leads from each bin for the Wnt1 blockers and the most potent and efficacious Wnt3a blockers were subsequently tested in Wnt1 and Wnt3a dependent LRP5 and LRP6 phosphorylation assays. CELLSENSOR™ LEF/TCF 293F cells from Invitrogen (cat K1677), co-transfected with expression vectors coding for either Wnt1 or Wnt3a, were used in the phosphorylation assays. Since Wnt-Frizzled-LRP5 or -LRP6 complex formation results in LRP5 or LRP6 phosphorylation and subsequent downstream signaling, quantification of phosphorylation can be used to measure such signaling. To obtain a LRP5 and LRP6 specific read-out, the cells were lysed and immuno-precipitation was performed with an LRP6 or LRP5 selective antibody (directed against the intracellular domain of the two receptors). In Western blot, phosphorylated LRP6 or LRP5 was detected using a polyclonal anti-phospho-LRP6 (Ser1490) antibody (Cell Signaling Technology), which detects both LRP6 and LRP5 phosphorylated protein. A selected panel of purified Wnt1 and Wnt3a blocking VHHs, containing at least one representative VHH from each bin, were tested at final concentrations of 10 to 100 nM. In particular, cells were incubated overnight in the presence of the blocking VHHs prior cell lysis and LRP5 and LRP6 immuno-precipitation. Efficacy of the Wnt1 and Wnt3a blocking VHHs in blocking LRP5 and LRP6 phosphorylation was calculated via quantification of the Western blot bands against the positive control (DKK1, final concentration of 1 uM).

4.6 Biophysical Characterization

The LRP5/LRP6 cross-reactive VHHs were further characterized for expression and purification in *E. coli* and in *Pichia pastoris*, as reported in Example 3. In particular, expression yields for the monovalent lead panel VHHs was considered acceptable if they were above 0.1 mg/L. The selected LRP5/LRP6 cross-reactive VHHs showed expression ranging between 0.1 and 8.2 mg/L in *E. coli* and higher in *Pichia pastoris* (>1 mg/L). The expression was evaluated by SDS-PPAGE analysis.

Thermal stability of the monovalent LRP5/LRP6 cross-reactive VHHs was determined in a fluorescence-based thermal shift assay (TSA) using the LIGHTCYCLER® real-time PCR system (Roche). VHHs were incubated at different pH values in the presence of Sypro Orange and a temperature gradient was applied. Upon heat-induced unfolding, hydrophobic patches of the proteins are exposed to which the Sypro Orange binds resulting in an increase in fluorescence intensity (Ex/Em=465/580 nm). The inflection point of the first derivative of the fluorescence intensity curve serves as a measure of the melting temperature (Tm). For all VHHs, Tm increased with increasing pH and levels off at pH 6, a typical Tm pattern seen for VHHs. An average of 82° C. at pH 7 was obtained for the LRP5/LRP6 cross-reactive Wnt1 blocker VHHs and Wnt3a blocker VHHs.

Potential occurrence of aggregation and multimerisation for LRP5 and LRP6 VHHs was investigated by analytical size exclusion chromatography (SEC). To this end, 8 ug of purified VHH sample at 0.5 mg/mL were injected via the DIONEX™ ULTIMATE™ 3000 HPLC equipment on an Agilent SEC-3 column. L-arginine buffer (10 mM phosphate, 300 mM Arg-HCl, pH 6.0) was used as mobile phase and a flow rate of 1 mL/min was applied. None of the LRP5/LRP6 VHHs showed major aggregation issues during SEC analysis: profiles indicated more than 95% monomer for most samples.

Example 5: Generation and Characterization of Half-Life Extended Biparatopic Constructs The LRP5/LRP6 cross-reactive Wnt1 and Wnt3a VHHs were used as building blocks to generate a biparatopic construct as depicted in FIG. 1. A genetic fusion to a serum albumin binding VHH was used as a half-life extension methodology. The three building blocks (Wnt1 blocker, Wnt3a blocker, and the albumin binder) were linked via a flexible linker. VHHs were produced in *P. pastoris* and purified as described in Example 3. The resulting constructs, i.e. biparatopic, half-life extended LRP5/LRP6 cross-reactive VHH constructs, were cloned in *P. pastoris* expression vector pAX159, in the form of C-terminally cMyc-hexahistidine tagged (SEQ ID NO: 59) VHH constructs, according to standard procedures as e.g. reported in WO2012/131078. Different orientation of the building blocks and different linkers, esp. GS-linkers, were explored. A relatively long GS-linker was selected, based on modeling data reflecting an extended surface area between the potential Wnt1 and Wnt3a binding sites in LRP6 (i.e. beta-propellers 1 and 2 not being in close proximity to beta-propeller 3). Best results regarding potency in the combined Wnt1 and Wnt3a reporter assay were obtained by putting the human serum albumin/HSA binding VHH in the middle. A 35 GS linker was used, and Wnt1 and Wnt3a VHH blockers arranged in a preferred order.

For selection of optimal VHH binders and binder combinations, a library was generated where the human serum albumin (HSA) binding VHH was placed in between the LRP5/LRP6 Wnt1-Wnt3a blockers. In particular, the panel of high affinity binders with high potency and efficacy in Wnt1 or Wnt3a assays (reporter and phosphorylation assays) were used in the library to generate half-life extended biparatopic constructs designed as depicted in FIG. 1. After expression in *Pichia pastoris* (as reported in Example 3) followed by purification, the half-life extended biparatopic constructs were subsequently screened in the Wnt1 and Wnt3a reporter assays (described in Example 4) in the presence of 30 uM HSA at three dilutions (1/100, 1/1000, 1/7000), to assess efficacy and relative potency. In general, a good correlation was observed between the data in the Wnt1 and Wnt3a reporter assays and high efficacies were measured for numerous formats. A total of 11 half-life extended biparatopic LRP5 and LRP6 constructs were selected for further characterization, taking into account the efficacy in both reporter assays and diversity of the Wnt1 and Wnt3a blockers. This further characterization assays are described below.

Wnt1/Wnt3a Reporter Assays:

Wnt1 and Wnt3a reporter assays were performed as described in Example 4.4, in the presence of 30 uM HSA final concentration. The purified biparatopic LRP5/LRP6 constructs were tested at 12 dilutions, starting from 2.5 uM. The majority of the constructs showed high potency—ranging between 1.7 nM and 0.16 nM—and full efficacy in both reporter assays, as shown in Table IV below. The sequences of the individual Wnt1 and Wnt3a inhibiting VHH domains set out therein are provided in Table V below:

TABLE IV

Potency and efficacy of selected half-life extended biparatopic LRP5/LRP6 cross-reactive VHH constructs in the reporter assays in the presence of HSA

| Construct | N-term | C-term | Wnt1 reporter assay | | Wnt3a reporter assay | |
| --- | --- | --- | --- | --- | --- | --- |
| | | | IC$_{50}$ (M) | % inh. | IC$_{50}$ (M) | % inh. |
| F013500053 | F0129093A01 | F0130333G06 | 2.3E−10 | 102 | 4.1E−10 | 97 |
| F013500039 | F0129093A03 | F0130333E06 | 1.7E−09 | 102 | 1.6E−09 | 82 |
| F013500046 | F0130332D03 | F0129093A01 | 5.1E−10 | 102 | 6.0E−10 | 96 |
| F013500016 | F0130332D03 | F0130367B10 | 3.1E−10 | 102 | 2.7E−10 | 99 |
| F013500018 | F0130332D03 | F0130378B05 | 7.4E−10 | 102 | 1.3E−09 | 98 |
| F013500047 | F0130333E06 | F0129093A01 | 8.8E−10 | 102 | 9.1E−10 | 94 |
| F013500026 | F0130333E06 | F0130367B10 | 3.3E−10 | 102 | 2.6E−10 | 100 |
| F013500021 | F0130333G06 | F0130367B10 | 1.6E−10 | 102 | 1.8E−10 | 102 |
| F013500032 | F0130378A04 | F0130333G06 | 2.4E−10 | 102 | 4.3E−10 | 94 |
| F013500033 | F0130378B05 | F0130333G06 | 1.8E−10 | 102 | 2.5E−10 | 88 |
| F013500030 | F0130378B05 | F0130372C08 | 1.4E−09 | 102 | 1.3E−09 | 96 |

TABLE V

Sequences of the VHH domains set out in Table IV

| VHH ID Specificity | Amino Acid Sequence | SEQ ID NO: |
|---|---|---|
| F0129093A01 Wnt3a | EVQLVESGGGLVQPGGSLRLSCAASGRTFSSYAMGWFRQAPGKER EFVAAISWSGGSTYYADSVKGRFTISRDNSKNTVYLQMNSLRPEDT AVYYCAASPIPYGSLLRRRNNYDYWGQGTLVTVSSAAAEQKLISEED LNGAAHHHHHH | 28 |
| F0130333G06 Wnt1 | EVQLVESGGGLVQPGGSLRLSCAASGGTFSSYAMGWFRQAPGKER EFVAAIRRSGRRTYYADSVKGRFTISRDNSKNTVYLQMNSLRPEDTA VYYCAAARRVRSSTRYNTGTWWWEYWGQGTLVTVSSAAAEQKLI SEEDLNGAAHHHHHH | 29 |
| F0129093A03 Wnt3a | EVQLVESGGGLVQPGGSLRLSCAASGRTFSTYVMGWFRQAPGKER EFVAAINWSGSRTYYADSVKGRFTISRDNSKNTVYLQMNSLRPEDT AVYYCAASRSSYAGRTYYELYDYWGQGTLVTVSSAAAEQKLISEEDL NGAAHHHHHH | 30 |
| F0130333E06 Wnt1 | EVQLVESGGGLVQPGGSLRLSCAASGRTFSTYTVGWFRQAPGKERE FVAAIRRRGSSTYYSDSVKGRFTISRDNSKNTVYLQMNSLRPEDTAV YYCAADTRTVALLQYRYDYWGQGTLVTVSSAAAEQKLISEEDLNGA AHHHHHH | 31 |
| F0130332D03 Wnt1 | EVQLVESGGGLVQPGGSLRLSCAASGLTFSRYTMGWFRQAPGKER EFVAAINRSGGSTYYSDSVKGRFTISRDNSKNTVYLQMNSLRPEDTA VYYCAADRRGRGENYSLLYSSNRYEYWGQGTLVTVSSAAAEQKLISE EDLNGAAHHHHHH | 32 |
| F0130367B10 Wnt3a | EVQLVESGGGLVQPGGSLRLSCAASGGTFSSYAMGWFRQAPGKER EFVAAISWRSGSTYYADSVKGRFTISRDNSKNTVYLQMNSLRPEGT AVYYCAADPRGYGVAYVSAYYEYWGQGTLVTVSSGAAEQKLISEED LNGAAHHHHHH | 33 |
| F0130378B05 Wnt3a | EVQLVESGGGLVQPGGSLRLSCVASGRTFSSYAMGWFRQAPGKER EFVAAISRSGGRTYYADSVKGRFTISRDNSKNTVYLQMNSLRPEDTA VYYCAADRRVYSTLPPTTSRYNYWGQGTLVTVSSAAAEQKLISEEDL NGAAHHHHHH | 34 |
| F0130378A04 Wnt3a | EVQLVESGGGLVQPGGSLRLSCAASGRTFSSYAMGWFRQAPGKER EFVAAITRTGRRTYYADSVKGRFTISRDNSKNTVYLQMNSLRPEDTA VYYCAADRRGYYYYDSSFYDYWGQGTLVTVSSAAAEQKLISEEDLN GAAHHHHHH | 35 |
| F0130372C08 Wnt1 | EVQLVESGGGLVQPGGSLRLSCAASGRTFSDYGMGWFRQAPGKE REFVAAISWSGGRTYYADSVKGRFTISRDNSKNTVYLQMNSLRPED TAVYYCAAKRRGRGSVSPNSSSRYNYWGQGTLVTVSSAAAEQKLIS EEDLNGAAHHHHHH | 36 |
| F013500016 | EVQLVESGGGLVQPGGSLRLSCAASGLTFSRYTMGWFRQAPGKER EFVAAINRSGGSTYYSDSVKGRFTISRDNSKNTVYLQMNSLRPEDTA VYYCAADRRGRGENYSLLYSSNRYEYWGQGTLVTVSSGGGGSGGG GSGGGGSGGGGSGGGGSGGGGSGGGGSEVQLVESGGGLVQPGN SLRLSCAASGFTFSSFGMSWVRQAPGKGLEWVSSISGSGSDTLYAD SVKGRFTISRDNAKTTLYLQMNSLRPEDTAVYYCTIGGSLSRSSQGTL VTVSSGGGGSGGGGSGGGGSGGGGSGGGGSGGGGSGGGGSEV QLVESGGGLVQPGGSLRLSCAASGGTFSSYAMGWFRQAPGKEREF VAAISWRSGSTYYADSVKGRFTISRDNSKNTVYLQMNSLRPEGTAV YYCAADPRGYGVAYVSAYYEYWGQGTLVTVSSGAAEQKLISEEDLN GAAHHHHHH | 37 |
| F013500018 | EVQLVESGGGLVQPGGSLRLSCAASGLTFSRYTMGWFRQAPGKER EFVAAINRSGGSTYYSDSVKGRFTISRDNSKNTVYLQMNSLRPEDTA VYYCAADRRGRGENYSLLYSSNRYEYWGQGTLVTVSSGGGGSGGG GSGGGGSGGGGSGGGGSGGGGSEVQLVESGGGLVQPGN SLRLSCAASGFTFSSFGMSWVRQAPGKGLEWVSSISGSGSDTLYAD SVKGRFTISRDNAKTTLYLQMNSLRPEDTAVYYCTIGGSLSRSSQGTL VTVSSGGGGSGGGGSGGGGSGGGGSGGGGSGGGGSGGGGSEV QLVESGGGLVQPGGSLRLSCVASGRTFSSYAMGWFRQAPGKEREF VAAISRSGGRTYYADSVKGRFTISRDNSKNTVYLQMNSLRPEDTAVY YCAADRRVYSTLPPTTSRYNYWGQGTLVTVSSGAAEQKLISEEDLN GAAHHHHHH | 38 |
| F013500021 | EVQLVESGGGLVQPGGSLRLSCAASGGTFSSYAMGWFRQAPGKER EFVAAIRRSGRRTYYADSVKGRFTISRDNSKNTVYLQMNSLRPEDTA VYYCAAARRVRSSTRYNTGTWWWEYWGQGTLVTVSSGGGGSGG GGSGGGGSGGGGSGGGGSGGGGSEVQLVESGGGLVQPG NSLRLSCAASGFTFSSFGMSWVRQAPGKGLEWVSSISGSGSDTLYA DSVKGRFTISRDNAKTTLYLQMNSLRPEDTAVYYCTIGGSLSRSSQG | 39 |

TABLE V-continued

Sequences of the VHH domains set out in Table IV

| VHH ID Specificity | Amino Acid Sequence | SEQ ID NO: |
|---|---|---|
| | TLVTVSSGGGGSGGGGSGGGGSGGGGSGGGGSGGGGSGGGGSE VQLVESGGGLVQPGGSLRLSCAASGGTFSSYAMGWFRQAPGKERE FVAAISWRSGSTYYADSVKGRFTISRDNSKNTVYLQMNSLRPEGTA VYYCAADPRGYGVAYVSAYYEYWGQGTLVTVSS<u>GAAEQKLISEEDL NGAAHHHHHH</u> | |
| F013500026 | EVQLVESGGGLVQPGGSLRLSCAASGRTFSTYTVGWFRQAPGKERE FVAAIRRGSSTYYSDSVKGRFTISRDNSKNTVYLQMNSLRPEDTAV YYCAADTRTVALLQYRYDYWGQGTLVTVSSGGGGSGGGGSGGGG SGGGGSGGGGSGGGGSGGGGSEVQLVESGGGLVQPGNSLRLSCA ASGFTFSSFGMSWVRQAPGKGLEWVSSISGSGSDTLYADSVKGRFT ISRDNAKTTLYLQMNSLRPEDTAVYYCTIGGSLSRSSQGTLVTVSSG GGGSGGGGSGGGGSGGGGSGGGGSGGGGSGGGGSEVQLVESG GGLVQPGGSLRLSCAASGGTFSSYAMGWFRQAPGKEREFVAAISW RSGSTYYADSVKGRFTISRDNSKNTVYLQMNSLRPEGTAVYYCAAD PRGYGVAYVSAYYEYWGQGTLVTVSS<u>GAAEQKLISEEDLNGAAHH HHHH</u> | 40 |
| F013500030 | EVQLVESGGGLVQPGGSLRLSCVASGRTFSSYAMGWFRQAPGKER EFVAAISRSGGRTYYADSVKGRFTISRDNSKNTVYLQMNSLRPEDTA VYYCAADRRVYSTLPPTTSRYNYWGQGTLVTVSSGGGGSGGGGSG GGGSGGGGSGGGGSGGGGSGGGGSEVQLVESGGGLVQPGNSLR LSCAASGFTFSSFGMSWVRQAPGKGLEWVSSISGSGSDTLYADSVK GRFTISRDNAKTTLYLQMNSLRPEDTAVYYCTIGGSLSRSSQGTLVTV SSGGGGSGGGGSGGGGSGGGGSGGGGSGGGGSGGGGSEVQLVE SGGGLVQPGGSLRLSCAASGRTFSDYGMGWFRQAPGKEREFVAAI SWSGGRTYYADSVKGRFTISRDNSKNTVYLQMNSLRPEDTAVYYCA AKRRGRGSVSPNSSSRYNYWGQGTLVTVSS<u>GAAEQKLISEEDLNGA AHHHHHH</u> | 41 |
| F013500032 | EVQLVESGGGLVQPGGSLRLSCAASGRTFSSYAMGWFRQAPGKER EFVAAITRTGRRTYYADSVKGRFTISRDNSKNTVYLQMNSLRPEDTA VYYCAADRRGYYYDSSFYDYWGQGTLVTVSSGGGGSGGGGSGG GGSGGGGSGGGGSGGGGSGGGGSEVQLVESGGGLVQPGNSLRLS CAASGFTFSSFGMSWVRQAPGKGLEWVSSISGSGSDTLYADSVKG RFTISRDNAKTTLYLQMNSLRPEDTAVYYCTIGGSLSRSSQGTLVTVS SGGGGSGGGGSGGGGSGGGGSGGGGSGGGGSGGGGSEVQLVES GGGLVQPGGSLRLSCAASGGTFSSYAMGWFRQAPGKEREFVAAIR RSGRRTYYADSVKGRFTISRDNSKNTVYLQMNSLRPEDTAVYYCAA ARRVRSSTRYNTGTWWWEYWGQGTLVTVSS<u>GAAEQKLISEEDLN GAAHHHHHH</u> | 42 |
| F013500033 | EVQLVESGGGLVQPGGSLRLSCVASGRTFSSYAMGWFRQAPGKER EFVAAISRGGRTYYADSVKGRFTISRDNSKNTVYLQMNSLRPEDTA VYYCAADRRVYSTLPPTTSRYNYWGQGTLVTVSSGGGGSGGGGSG GGGSGGGGSGGGGSGGGGSEVQLVESGGGLVQPGNSLR LSCAASGFTFSSFGMSWVRQAPGKGLEWVSSISGSGSDTLYADSVK GRFTISRDNAKTTLYLQMNSLRPEDTAVYYCTIGGSLSRSSQGTLVTV SSGGGGSGGGGSGGGGSGGGGSGGGGSGGGGSGGGGSEVQLVE SGGGLVQPGGSLRLSCAASGGIFSSYAMGWFRQAPGKEREFVAAI RRSGRRTYYADSVKGRFTISRDNSKNTVYLQMNSLRPEDTAVYYCA AARRVRSSTRYNTGTWWWEYWGQGTLVTVSS<u>GAAEQKLISEEDL NGAAHHHHHH</u> | 43 |
| F013500039 | EVQLVESGGGLVQPGGSLRLSCAASGRTFSTYVMGWFRQAPGKER EFVAAINWSGRTYYADSVKGRFTISRDNSKNTVYLQMNSLRPEDT AVYYCAASRSSYAGRTYYELYDYWGQGTLVTVSSGGGGSGGGGS GGGSGGGGSGGGGSGGGGSGGGGSEVQLVESGGGLVQPGNSLR LSCAASGFTFSSFGMSWVRQAPGKGLEWVSSISGSGSDTLYADSVK GRFTISRDNAKTTLYLQMNSLRPEDTAVYYCTIGGSLSRSSQGTLVTV SSGGGGSGGGGSGGGGSGGGGSGGGGSGGGGSGGGGSEVQLVE SGGGLVQPGGSLRLSCAASGRTFSTYTVGWFRQAPGKEREFVAAIR RRGSSTYYSDSVKGRFTISRDNSKNTVYLQMNSLRPEDTAVYYCAAD TRTVALLQYRYDYWGQGTLVTVSS<u>GAAEQKLISEEDLNGAAHHHH HH</u> | 44 |
| F013500046 | EVQLVESGGGLVQPGGSLRLSCAASGLTFSRYTMGWFRQAPGKER EFVAAINRSGGSTYYSDSVKGRFTISRDNSKNTVYLQMNSLRPEDTA VYYCAADRRGRGENYSLLYSSNRYEYWGQGTLVTVSSGGGGSGGG GSGGGGSGGGGSGGGGSGGGGSEVQLVESGGGLVQPGN SLRLSCAASGFTFSSFGMSWVRQAPGKGLEWVSSISGSGSDTLYAD SVKGRFTISRDNAKTTLYLQMNSLRPEDTAVYYCTIGGSLSRSSQGTL | 45 |

TABLE V-continued

Sequences of the VHH domains set out in Table IV

| VHH ID Specificity | Amino Acid Sequence | SEQ ID NO: |
|---|---|---|
|  | VTVSSGGGGSGGGGSGGGGSGGGGSGGGGSGGGGSGGGGSEV QLVESGGGLVQPGGSLRLSCAASGRTFSSYAMGWFRQAPGKEREF VAAISWSGGSTYYADSVKGRFTISRDNSKNTVYLQMNSLRPEDTAV YYCAASPIPYGSLLRRRNNYDYWGQGTLVTVSS<u>GAAEQKLISEEDLN GAAHHHHHH</u> |  |
| F013500047 | EVQLVESGGGLVQPGGSLRLSCAASGRTFSTYTVGWFRQAPGKERE FVAAIRRRGSSTYYSDSVKGRFTISRDNSKNTVYLQMNSLRPEDTAV YYCAADTRTVALLQYRYDYWGQGTLVTVSSGGGGSGGGGSGGGG SGGGGSGGGGSGGGGSGGGGSEVQLVESGGGLVQPGNSLRLSCA ASGFTFSSFGMSWVRQAPGKGLEWVSSISGSGSDTLYADSVKGRFT ISRDNAKTTLYLQMNSLRPEDTAVYYCTIGGSLSRSSQGTLVTVSSG GGGSGGGGSGGGGSGGGGSGGGGSGGGGSGGGGSEVQLVESG GGLVQPGGSLRLSCAASGRTFSSYAMGWFRQAPGKEREFVAAISW SGGSTYYADSVKGRFTISRDNSKNTVYLQMNSLRPEDTAVYYCAAS PIPYGSLLRRRNNYDYWGQGTLVTVSS<u>GAAEQKLISEEDLNGAAHH HHHH</u> | 46 |
| F013500053 | EVQLVESGGGLVQPGGSLRLSCAASGRTFSSYAMGWFRQAPGKER EFVAAISWSGGSTYYADSVKGRFTISRDNSKNTVYLQMNSLRPEDT AVYYCAASPIPYGSLLRRRNNYDYWGQGTLVTVSSGGGGSGGGGS GGGGSGGGGSGGGGSGGGGSGGGGSEVQLVESGGGLVQPGNSL RLSCAASGFTFSSFGMSWVRQAPGKGLEWVSSISGSGSDTLYADSV KGRFTISRDNAKTTLYLQMNSLRPEDTAVYYCTIGGSLSRSSQGTLVT VSSGGGGSGGGGSGGGGSGGGGSGGGGSGGGGSGGGGSEVQLV ESGGGLVQPGGSLRLSCAASGGTFSSYAMGWFRQAPGKEREFVAA IRRSGRRTYYADSVKGRFTISRDNSKNTVYLQMNSLRPEDTAVYYCA AARRVRSSTRYNTGTWWWEYWGQGTLVTVSS<u>GAAEQKLISEE DLNGAAHHHHHH</u> | 47 |

(Note: The molecules described in this Table V include a myc-hexa-histidine tag (underlined), to allow for easier purification of the recombinantly expressed polypeptides; this tag is not required for—nor does it usually interfere with—the binding of the molecules to their targets)

Example 6: Sequence Optimization of VHHs and VHH Constructs

Sequence optimization is a process in which the parental sequence is mutated to make it more identical to the human IGHV3-IGHJ germline consensus sequence. For example, specific amino acids in the framework regions (with the exception of the so-called hallmark residues) are exchanged for their human counterparts, in a way that the protein structure, activity and stability shall be preserved.

These mutations may be categorized as follows:
1. Standard: Sequence optimization of these positions is not expected to dramatically change the stability or activity or affinity of the VHH and they are therefore altered all at once, yielding a basic variant.
2. Unique: It is not known if sequence optimization of these positions affects the stability or activity or affinity of the VHH and therefore they are investigated on an individual basis on top of the basic variant.

Hallmark residues are known to be critical for the stability, activity and affinity of the VHH and are therefore not mutated.

In addition, the amino acids present in the CDRs for which there is experimental evidence that they are sensitive to post-translational modifications (PTM) were altered in such a way that the PTM site is inactivated while the protein structure, activity and stability shall remain intact. The most common post-translational modifications described for antibodies and VHHs are listed in Table VI below. The sensitivity of the VHHs for post-translational modifications was analysed in accelerated stress studies, applying several standard conditions including $H_2O_2$ treatment to analyze methionine oxidation, high temperature, high pH and long storage to study asparagine deamidation and aspartate isomerization. The percentage of oxidation, deamidation and isomerization was measured according to standard procedures and compared to the reference samples (VHHs stored at −20° C.). Whole protein analysis in Reverse Phase Chromatography (RPC) and peptide mapping using Mass Spectrometry (MS) were performed to identify potentially sensitive residues. In case of post-translational modifications observed in the VHHs after stress test, the corresponding amino acid(s) were mutated.

TABLE VI

Potential post-translational modifications, and motifs potentially triggering them

| Motif | Modification |
|---|---|
| M | Met oxidation |
| N-S/G/H/N/A | Asn deamidation |
| D-S/G/H | Asp isomerisation |
| N-X-S/T-X (X ≠ P) | Asn glycosylation |
| Q/E | pyroglutamate |

As a result, several mutations were introduced in the constructs set out above, resulting i.a. in the three constructs shown in Table III above, which were chosen for further in vitro and in vivo characterization, as set out in the Examples further below.

Example 7: In Vitro Characterization of Three Half-Life Extended Biparatopic LRP5/LRP6 Cross-Reactive VHH Constructs; Comparison to Other LRP6 Binding Molecules After VHH sequence optimization, three half-life extended biparatopic LRP5/LRP6 cross-reactive VHH constructs were recombinantly expressed and purified, and were characterized by using several functional and biophysical assays as described below.

7.1 FACS Binding Assays

Figure 3A:
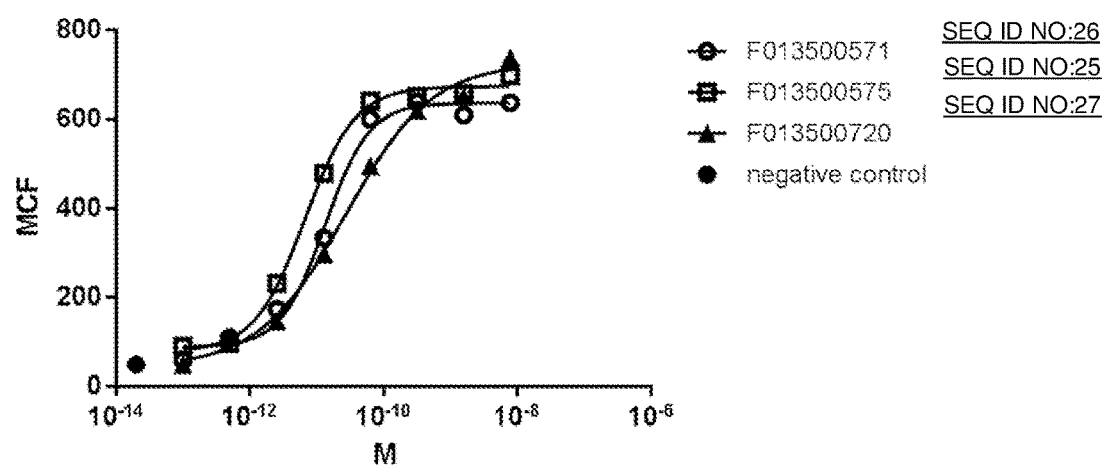
FIGS. 3A and 3B.
Figure 3B:
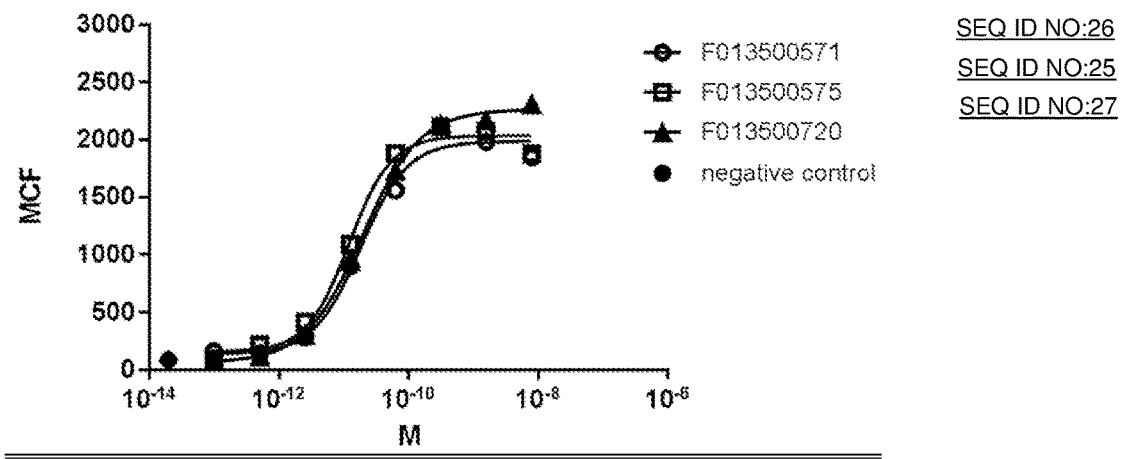

Binding to human LRP5 and LRP6 was determined on cells by FACS analysis, as reported in FIGS. 3A and 3B. In particular, binding to human LRP5 was tested on HEK293 cells with stable overexpression of human LRP5. For human LRP6 binding, HEK293 cells with stable overexpression of human LRP6 were used. The cells were incubated with the LRP5 and LRP6 binder dilutions (1:5 serial dilution of the binders corresponding to the final concentrations indicated in FIG. 3A and FIG. 3B) for 1.5 hours at 4° C. on a plate shaker. After washing the cells 5 times with FACS buffer (1×PBS (Invitrogen cat. no. 141190-094)+10% FBS (Sigma cat. no. F7524)+0.05% sodium azide), they were incubated for 1 hour at 4° C. with a polyclonal mouse antibody which binds to the framework regions of the VHHs. After washing the cells 3 times with FACS buffer, the cells were incubated for 1 hour at 4° C. with the labelled secondary antibody (anti-mouse PE (115-116-071), followed by 3 times washing step with FACS buffer. Fluorescence was measured using FACSARRAY™ bioanalyzer (BD). Binding to human LRP5 and LRP6 corresponds to 600 MCF values at the highest concentration tested. Negative control consisted of a non-targeting binder (VHH construct that binds to a bacterial protein which is not expressed in HEK293 cells). As shown in FIG. 3A and FIG. 3B, respectively, binding to human LRP5 and LRP6 corresponds to 600 MCF and to 1600 MCF values, respectively, at the highest tested concentrations of the three half-life extended biparatopic LRP5/LRP6 cross-reactive VHH constructs. These data confirm that the formatted, biparatopic, and sequence-optimized binding molecules bind to both human LRP5 and human LRP6 in their native conformation in a cellular assay system. EC50 values of binding to hLRP5 and hLRP6 are reported in Table VII below.

TABLE VII $EC_{50}$ values of binding to human LRP5 and LRP6 determined by FACS binding assays

| FACS based binding assay | F013500571 | F013500575 | F013500720 |
|---|---|---|---|
| hLRP5, $EC_{50}$ (nM) | 0.01 | 0.001 | 0.02 |
| hLRP6, $EC_{50}$ (nM) | 0.02 | 0.01 | 0.02 |

7.2 FACS—DKK1 Competition Assay

Figure 4A:
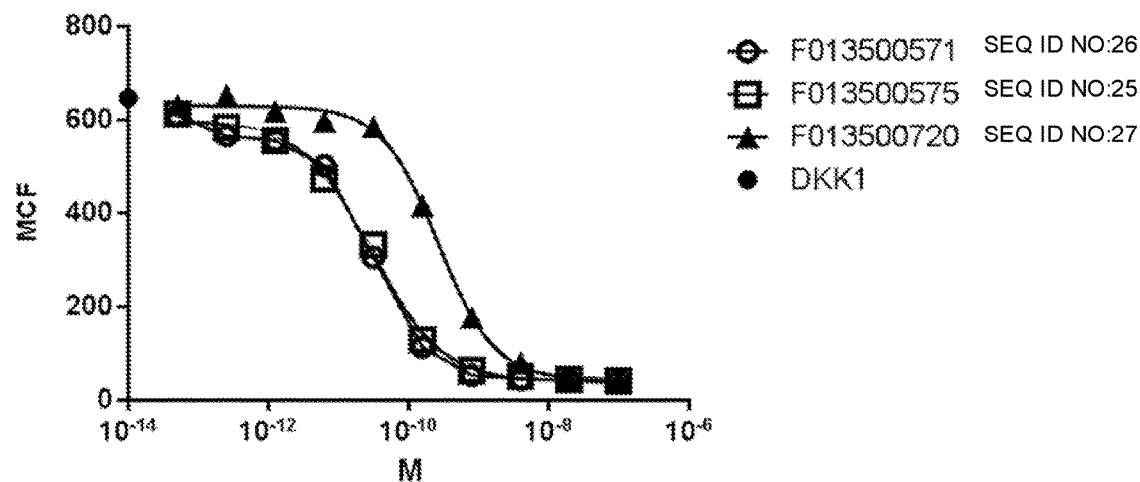
FIGS. 4A and 4B.
Figure 4B:
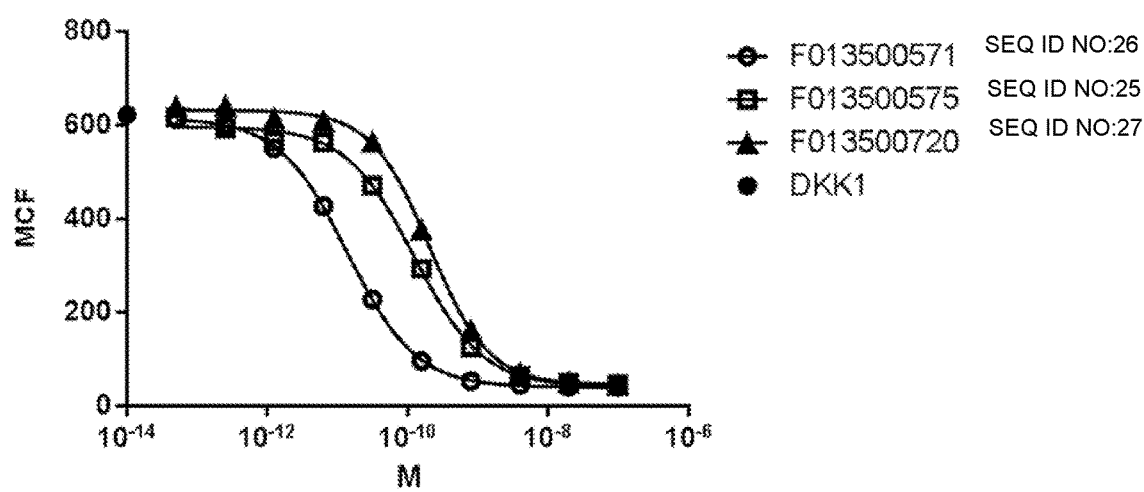

Potency and efficacy of the three LRP5/LRP6 cross-reactive VHH constructs were further analysed using the FACS-based DKK1 competition assay, as described in Example 4.1. HEK293 cells with stable overexpression of human LRP5 or human LRP6 were incubated with serial dilution of the LRP5/LRP6 cross-reactive VHH constructs (1:5 serial dilution corresponding to the final concentrations indicated in FIG. 4A and FIG. 4B). The LRP5/LRP6 cross-reactive VHHs competed with human DKK1 for binding to HEK293 cells overexpressing human LRP5, as well as for binding to HEK293 cells overexpressing human LRP6, as shown in FIGS. 4A and 4B, respectively. Complete inhibition of DKK1 binding was achieved at the highest tested concentrations (>10 nM) and corresponded to MCF values<60. In contrast, an LRP5 specific VHH would compete with human DKK1 for binding to HEK293 cells overexpressing human LRP5 but not, or with very low potency (>200 nM) for binding to HEK293 cells overexpressing human LRP6 (and the same would apply, vice versa, to LRP6 specific VHHs). As a result of this experiment, it could be shown that the present LRP5/LRP6 cross-reactive VHHs competed with human DKK1 for binding to HEK293 cells overexpressing human LRP5, as well as to those overexpressing human LRP6 (i.e. decrease in MCF value with increasing concentration of the binder with complete inhibition of DKK1 binding corresponded to <60 MCF values at the highest concentration tested). IC50 values of DKK1 competition for binding to hLRP5 and hLRP6 of the three LRP5/LRP6 cross-reactive VHH constructs are reported in Table VIII below. These data confirmed the binding of the three LRP5/LRP6 cross-reactive VHH constructs to human LRP5 and human LRP6 and showed very similar affinity (defined here by the $IC_{50}$ potency values in the DKK1 competition assay) between the two receptors. Furthermore, the data strengthen the notion that the formatted, biparatopic, and sequence-optimized binding molecules are binding to human LRP5 as well as to human LRP6 in their native conformation.

TABLE VIII $IC_{50}$ values of DKK1 competition for binding to human LEP5 and LRP6 determined by FACS binding assays

| DKK1 competition assay | F013500571 | F013500575 | F013500720 |
|---|---|---|---|
| hLRP5, $IC_{50}$ (nM) | 0.03 | 0.03 | 0.3 |
| hLRP6, $IC_{50}$ (nM) | 0.01 | 0.1 | 0.2 |

7.3 Combined Wnt1 and Wnt3a Reporter Assay

Figure 5A:
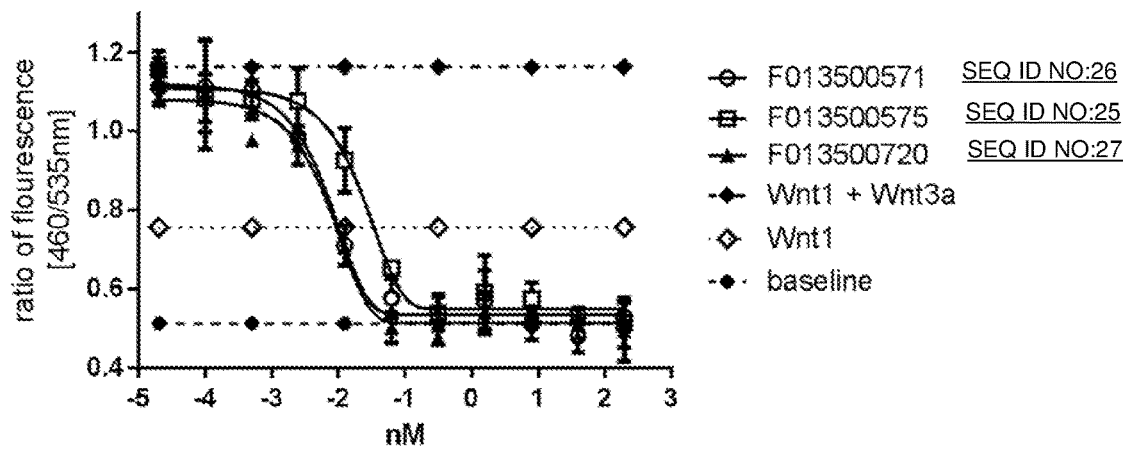
FIGS. 5A, 5B, and 5C.

Potency and efficacy of the formatted, biparatopic, and sequence-optimized binding molecules were analysed using a combined Wnt1 and Wnt3a reporter assay to allow functional testing of both Wnt1 and Wnt3a blockers in the same assay. The combined Wnt1 and Wnt3a reporter assay is based on the assay described in Example 4.4 with the following changes in the protocol. 1E06/ml cells with overexpression of Wnt1, seeded into a 384 well tissue culture plate were treated with recombinant human Wnt3a (rec.human Wnt3a: R&D #5036-WN/CF) at the final concentration of 500 ng/ml and then the cells were incubated overnight at 37° C. The following day, serial dilutions of various LRP5/LRP6 biparatopic cross-reactive VHH solutions were prepared and added to the cells in the presence of LiCl at the final concentration of 10 nM. DKK1, as positive control, was added to the cells at the final concentration of 200 nM. DKK1 treatment resulted in a complete inhibition of the combined Wnt1 and Wnt3a pathway, and therefore a complete inhibition of beta-lactamase enzymatic activity. The cells were incubated overnight at 37° C. The following day, beta-lactamase enzymatic activity was measured according to the manufacturer's instructions. As reported in Example 4.4., for fluorescence emission, values at 460 nm and 530 nm were obtained using a standard fluorescence plate reader and the 460/530 nm emission ratios plotted for the indicated treatment. The value of the ratio of fluorescence [460/535 nm] reported as "baseline" in FIG. 5A corresponds to complete inhibition of Wnt1 and Wnt3a pathway, determined by the treatment with the positive control (DKK1; 200 nM final concentration). The value of the ratio of fluorescence [460/535 nm] reported as "Wnt1" corresponds to activation of Wnt1 pathway only, determined from the Wnt1 overexpressing cells (i.e. without treatment with recombinant human Wnt3a). The value of the ratio of fluorescence [460/535 nm] reported as "Wnt1+Wnt3a" corresponds to the combined activation of Wnt1 and Wnt3a pathways, determined by treatment of the Wnt1 overexpressing cells with recombinant human Wnt3a. As shown in FIG. 5A, complete inhibition (i.e. ratio of fluorescence [460/535 nm] corresponding to the baseline) is achieved by treatment with the three LRP5/LRP6 cross-reactive, formatted, biparatopic, and sequence-optimized binding molecules. Furthermore, high potency is also reported, as shown in Table IX below by the IC50 values.

TABLE IX $IC_{50}$ values of Wnt1 and Wnt3a pathway inhibition in combined Wnt1 and Wnt3a reporter assay

| Combined Wnt1 and Wnt3a reported assay | F013500571 | F013500575 | F013500720 |
|---|---|---|---|
| $IC_{50}$ (nM) | 0.05 | 0.2 | 0.06 |

Next, potency and efficacy of the LRP5/LRP6 cross-reactive, formatted, biparatopic, and sequence-optimized binding molecules were compared to previously disclosed LRP6 binding molecules reported in WO2011/138391 and WO2011/119661:

In WO2011/138391, multivalent antibodies binding to LRP6 and inhibiting both propeller 1 (e.g., Wnt1) and propeller 3 (e.g., Wnt 3) ligand interaction were disclosed. These multivalent LRP6 binding antibodies are biparatopic LRP6 binding molecules consisting of an IgG antibody as a first receptor binding domain and of an scFv fragment as a second receptor binding domain, where the IgG antibody and scFv fragment are linked together by a linker. In WO2011/138391 it is reported that all the LRP6 binding molecules have roughly the same potency in Wnt1 and Wnt3a reporter assay (FIG. 18 of WO2011/138391). Therefore, any of those multivalent LRP6 binding molecules could be chosen for comparative experiments. Thus, it was decided to use the "901" construct (referred to as MOR08168IgG1LALA 6475 scfv; also shown in FIG. 27 of WO2011/138391) as a first comparative compound.

Derivatives of this "901" construct are shown in WO2013/067355. Specifically, compounds named 801T and 802T are disclosed (cf. disclosure on p. 132 of the specification), both having two LRP6 binding scFv domains, plus a half-life extending moiety. As 801T and 802T appear to have the same in vitro potency and biophysical characteristics, only one of them—variant 802T—was included in the experiments described in the following.

In WO2011/119661, bispecific antibodies binding to LRP6 and inhibiting signaling by multiple Wnt isoforms were disclosed. These bispecific anti-LRP6 antibodies bind to two different regions of LRP6 and inhibit signaling induced by Wnt isoforms, among them Wnt1 and Wnt3a. Knobs-into-holes engineering (Atwell et al. "Stable heterodimers from remodeling the domain interface of a homodimer using a phage display library". *J Mol Biol*. 1997; 270(1):26-35) was used to build these bispecific anti-LRP6 antibodies. Example 11 of WO2011/119661 discloses an IgG hybrid with YW211.31.62 and YW210.09 heavy chain heterodimers. Thus, for comparative purposes, two bispecific IgG hybrid antibodies with YW211.31.62 and YW210.09 heavy chain heterodimers were generated with the knobs-into-holes engineering technology, i.e. with amino acid changes engineered to create a knob on the CH3 of the heavy chain of YW210.09 and a hole on the CH3 of the heavy chain of YW211.31.62 or vice versa, and referred here as Knob HC YW210.09 and Knob HC YW211.31.62, respectively. These two constructs were characterized in Wnt1 and Wnt3a reporter assays according to Example 4.4. As expected, the two bispecific IgG hybrids with YW211.31.62 and YW210.09 heavy chain heterodimers showed similar potencies in Wnt1 and Wnt3a assays, as reported in Table X below. Thus, for the comparative examples shown further below, Knob HC YW210.09 was selected as a second comparative compound.

TABLE X $IC_{50}$ values of Wnt1 and Wnt3a pathway inhibition in Wnt1 and Wnt3a reporter assays

| Wnt reporter assay | Knob HC YW210.09 | Knob HC YW211.31.62 |
|---|---|---|
| Wnt1, $IC_{50}$ (nM) | 4.8 | 4.6 |
| Wnt3a, $IC_{50}$ (nM) | 0.7 | 0.9 |

Figure 5B:
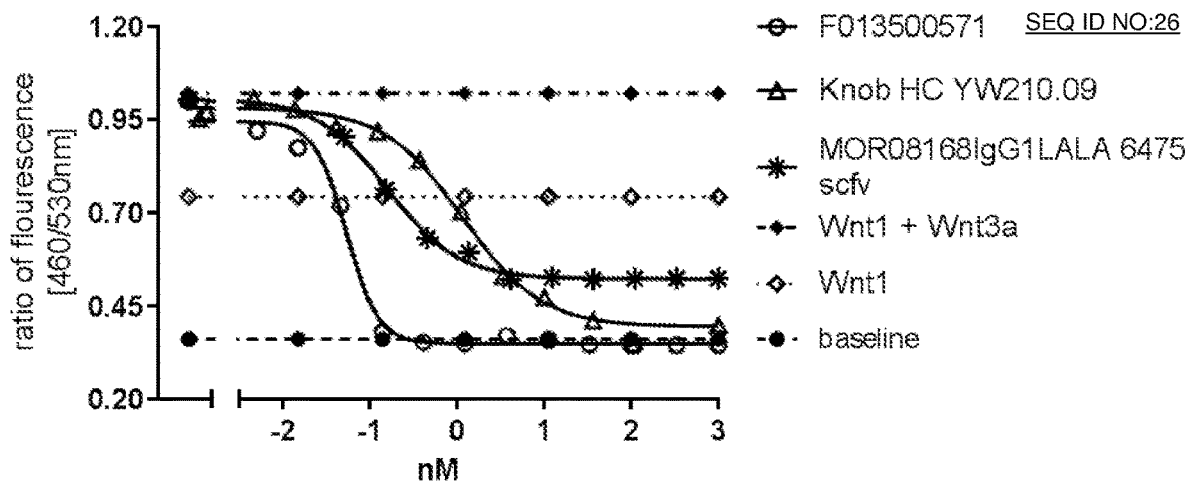
Figure 5C:
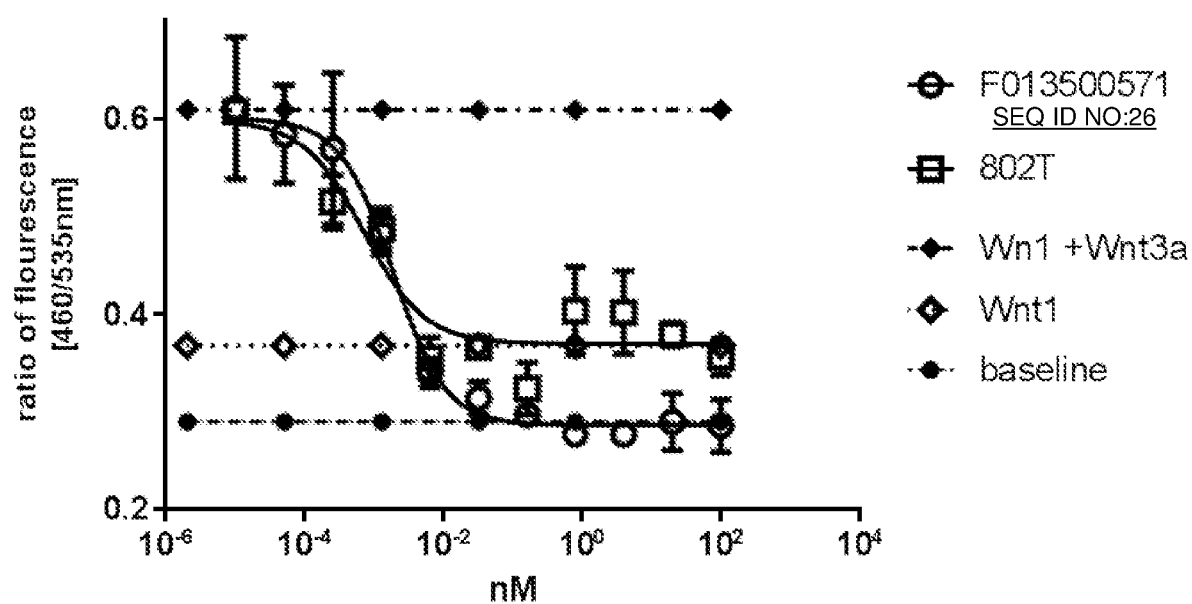

Potency and efficacy of the half-life extended biparatopic LRP5/LRP6 cross-reactive VHH constructs were compared to MOR08168IgG1LALA 6475 scfv biparatopic LRP6 binding molecule, to Knob HC YW210.09 bispecific anti-LRP6 molecule and to 802T bispecific anti-LRP6 molecule using the combined Wnt1 and Wnt3a reporter assay. As shown in FIG. 5B, complete inhibition (i.e. ratio of fluorescence [460/535 nm] corresponding to the baseline in FIG. 5B) was achieved by treatment with Knob HC YW210.09 (the bispecific IgG hybrid antibody with YW211.31.62 and YW210.09 heavy chain heterodimers) similar to the LRP5/LRP6 cross-reactive, formatted, biparatopic, and sequence-optimized binding molecule F013500571. However, F013500571 showed higher potency, as reported in Table XI below. Instead, MOR08168IgG1LALA 6475 scfv and 802T biparatopic LRP6 binding molecules showed lack of complete Wnt1 and Wnt3a inhibition (i.e. ratio of fluorescence [460/535 nm] significantly higher than the baseline in FIG. 5B and in FIG. 5C, respectively). These data indicate that both MOR08168IgG1LALA 6475 scfv and 802T biparatopic LRP6 binding molecules have significant lower efficacy in Wnt1 and Wnt3a pathway inhibition when compared to F013500571. Therefore, Knob HC YW210.09 was selected as a comparative compound for in vivo experiments as described further below (Example 9; in vivo efficacy)

TABLE XI $IC_{50}$ values of Wnt1 and Wnt3a pathway inhibition in combined Wnt1 and Wnt3a reporter assay

| Combined Wnt1 and Wnt3a reported assay | F013500571 | Knob HC YW210.09 | MOR08168IgG1LALA 6475 scfv | 802T |
|---|---|---|---|---|
| $IC_{50}$ (nM) | 0.05 | 1.15 | 0.19 | 0.01 |

Example 8: Effects of Three Half-Life Extended Biparatopic LRP5/LRP6 Cross-Reactive VHH Constructs on Wnt Signaling and Viability in Cancer Cell Lines The ability of the half-life extended biparatopic LRP5/LRP6 cross-reactive VHH constructs to inhibit active Wnt signaling was further characterized using cancer cell lines with active Wnt signaling, as previously described (Bafico et al. "An autocrine mechanism for constitutive Wnt pathway activation in human cancer cells". Cancer Cell 2004; 6(5): 497-506; DeAlmeida et al. "The soluble wnt receptor Frizzled8CRD-hFc inhibits the growth of teratocarcinomas in vivo". Cancer Res. 2007; 67(11):5371-9); Akiri et al. "Wnt pathway aberrations including autocrine Wnt activation occur at high frequency in human non-small-cell lung carcinoma". Oncogene. 2009; 28(21):2163-72). Briefly, the cancer cell lines with active Wnt signaling, PA-1 and PA-TU-8988S, were seeded in 12-well plates and treated for two days with the LRP5/LRP6 cross-reactive VHH constructs at the final concentration of 1 uM. The ability of inhibiting Wnt signaling was detected by inhibition of mRNA expression of Axin2, the endogenous Wnt target gene. qPCR expression analysis was performed using standard RNA techniques: RNA isolation was performed using the QIAGEN RNAEASY® Mini Kit according to the protocol provided by QIAGEN; cDNA synthesis using SUPERSCRIPT™ VILO™ cDNA Synthesis Kit (Invitrogen, Cat. No. 11754050) and qPCR using TAQMAN™ Gene Expression Assay with Axin2 TAQMAN™ primers/probe (Hs00610344_m1 AXIN2 FAM, Life Technologies) and with eukaryotic 18s endogenous control VIC-MGB (4319413E-1307061, Applied Biosystems).

Figure 6A:
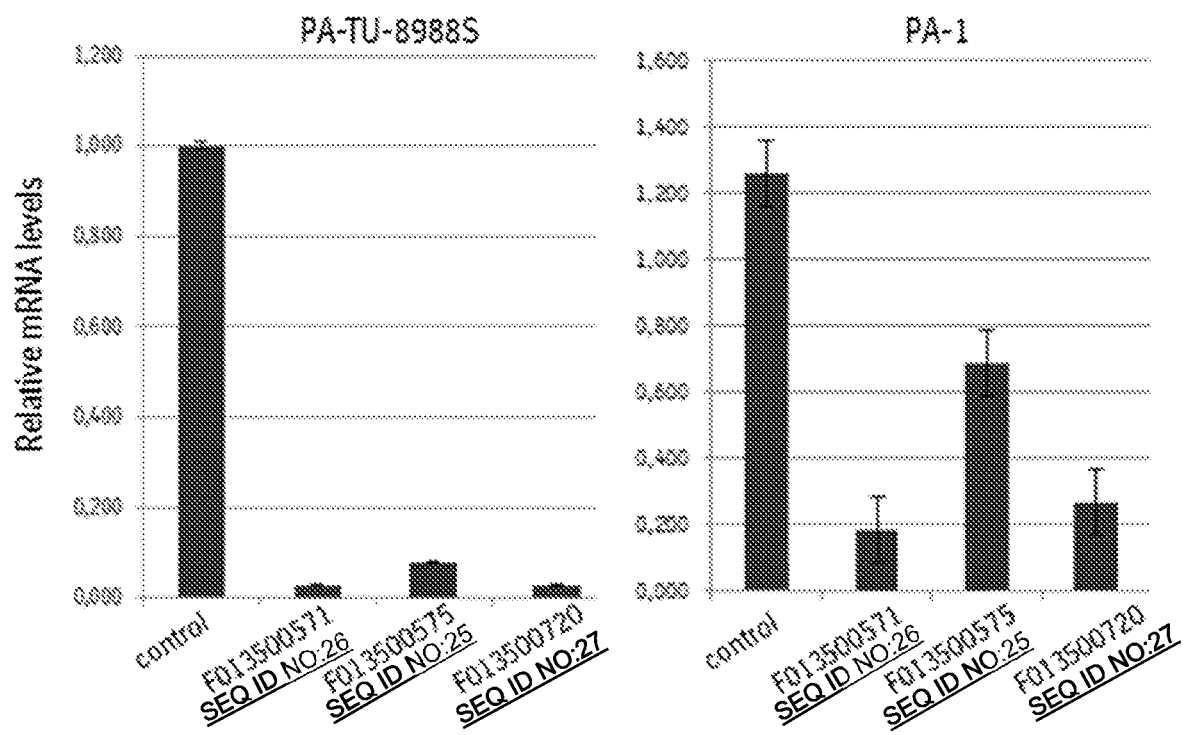
FIGS. 6A, 6B, 6C and 6D.
Figure 6B:
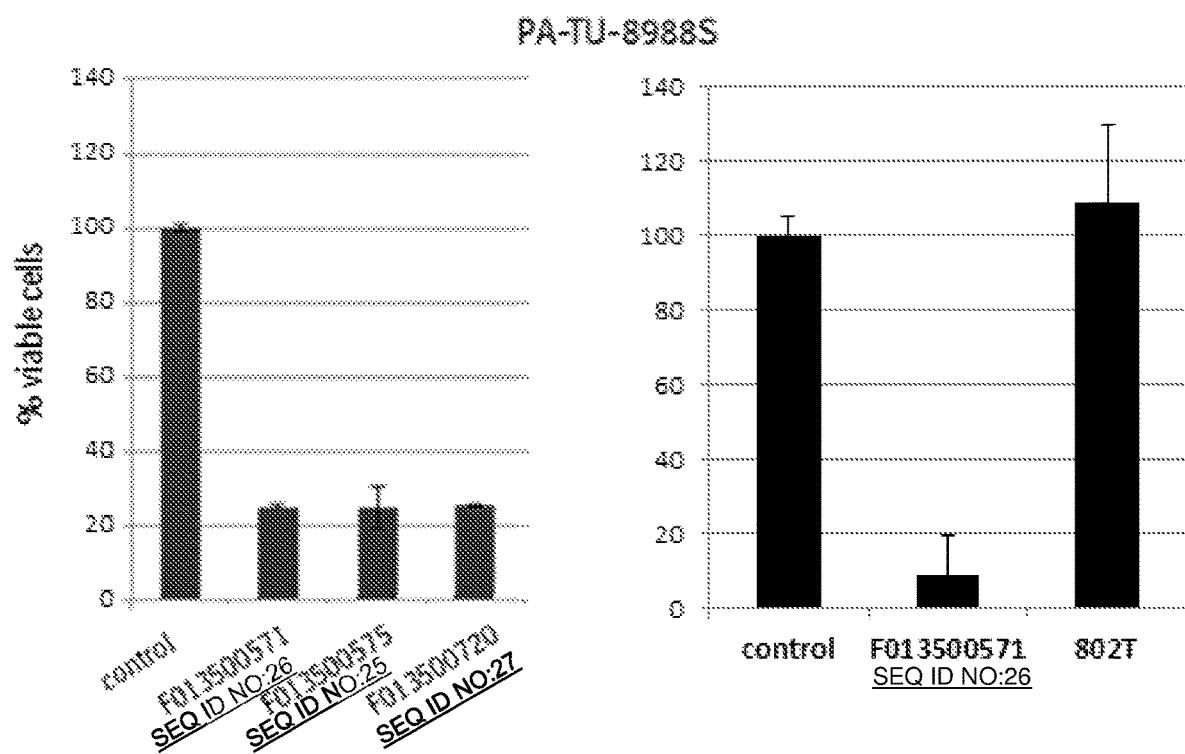

As shown in FIG. 6A, both PA-TU8988S and PA-1 cancer cells treated with three half-life extended biparatopic LRP5/LRP6 cross-reactive VHH constructs showed significantly reduced Axin2 relative mRNA levels (i.e. normalized to the endogenous control) when compared to untreated (Control) cells. These data demonstrated the ability of the half-life extended biparatopic LRP5/LRP6 cross-reactive VHH constructs to inhibit Wnt signaling in cancer cell lines with active Wnt signaling. Furthermore, the effect of Wnt signaling blockade on cell viability was investigated in PA-TU8988S and YAPC cancer cell lines, whose proliferation was previously reported to be dependent on active Wnt signaling (Jiang et al. "Inactivating mutations of RNF43 confer Wnt dependency in pancreatic ductal adenocarcinoma". Proc Natl Acad Sci USA. 2013; 110(31):12649-54). Cell viability was measured by performing an Alamar Blue assay (Invitrogen, Cat. #DAL1100) after ten days of treatment with the half-life extended biparatopic LRP5/LRP6 cross-reactive VHH constructs (final concentration of 1 uM) or with comparative compound 802T (final concentration 1 uM). As shown in FIG. 6B, PA-TU8988S cancer cells treated with three half-life extended biparatopic LRP5/LRP6 cross-reactive VHH constructs showed significantly reduced percentage of viable cells cell (>75% reduction) when compared to untreated (control) cells. Upon treatment with 802T, no effect on cell viability was detected (FIG. 6B, diagram on the right-hand side). These data demonstrate the ability of the half-life extended biparatopic LRP5/LRP6 cross-reactive VHH constructs to inhibit cell proliferation of cancer cells which are dependent on active Wnt signaling, and also show a superior effect of these constructs when compared to 802T.

Figure 6C:
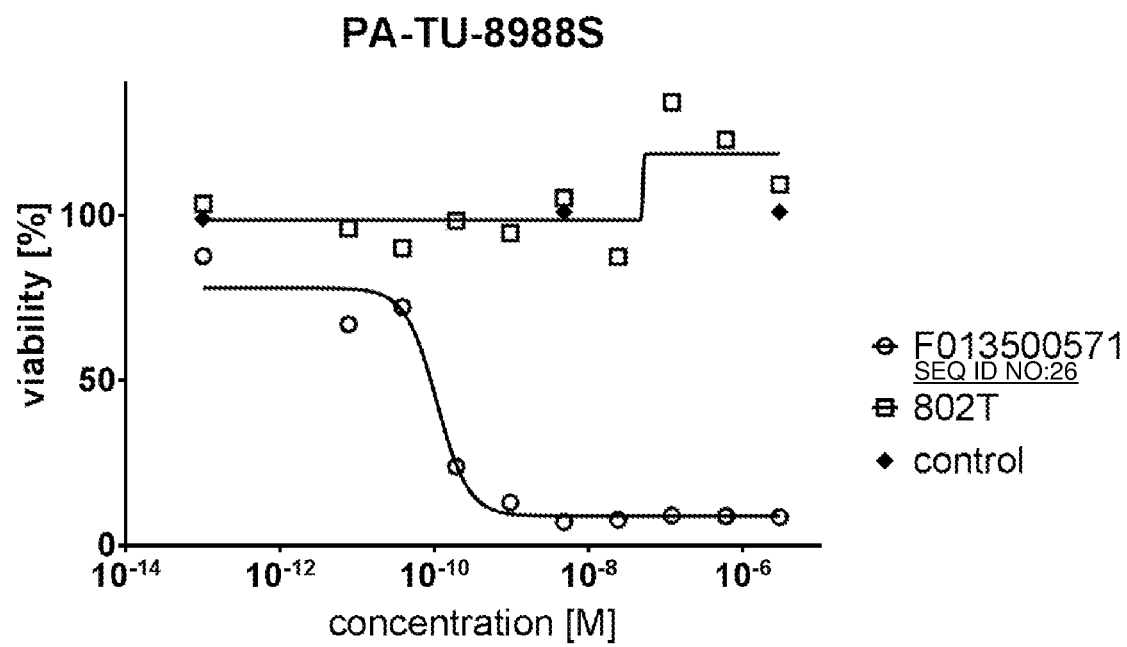
Figure 6D:
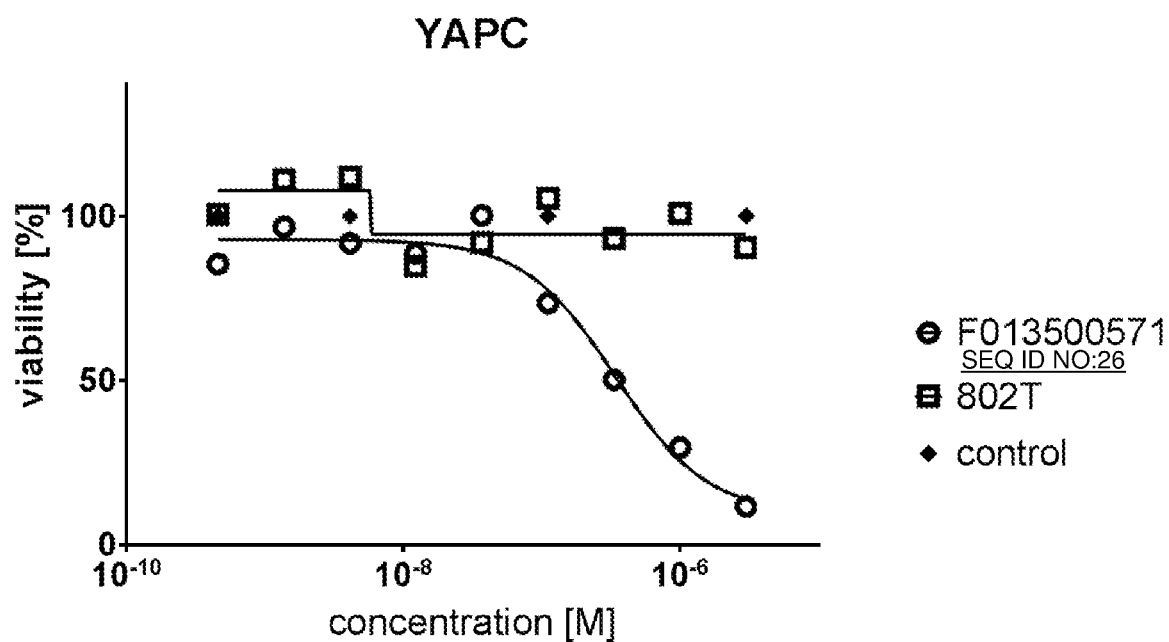

Furthermore, dose dependency of cell viability was assessed for F013500571 in comparison to 802T, in PA-TU8988S (FIG. 6C) and YAPC (FIG. 6D) cancer cell lines, as described above. Dose dependent decrease in cell viability was detected upon treatment with F013500571. In contrast, no effect on cell viability was shown upon treatment with the comparative compound 802T in both PA-TU8988S and YAPC cancer cell lines. These data show that the half-life extended biparatopic LRP5/LRP6 cross-reactive VHH constructs have a superior effect when compared to 802T.

Example 9: In Vivo Efficacy

The LRP5/LRP6 cross-reactive biparatopic half-life extended VHH constructs/binding molecules were further characterized in vivo in a Wnt driven tumor model. Experiments were conducted to determine if these binding molecules inhibit tumor growth in vivo. Efficacy of the comparative compound Knob HC YW210.09 was also determined using the same Wnt driven tumor model. Transgenic expression of the Wnt ligands using a mouse mammary tumor virus LTR enhancer (MMTV promoter) leads in mice to extensive ductal hyperplasia followed by mammary adenocarcinomas in transgenic (TG) mice by 6 months of age. These mammary tumors are driven by glucocorticoid induced overexpression of Wnt ligands and have characteristics similar to TNBC tumors, including expression of epithelial and mesenchymal markers (basal-like phenotype) and active Wnt signaling as assessed by intracellular beta-catenin localization. In particular, mammary tumors derived from MMTV-Wnt-1 transgenic mice are Wnt1 dependent. Indeed, blocking of Wnt activity using a soluble Wnt receptor comprising the Frizzled8 cysteine-rich domain (CRD) fused to the human Fc domain (F8CRDhFc) (DeAlmeida et al. "The soluble wnt receptor Frizzled8CRD-hFc inhibits the growth of teratocarcinomas in vivo". Cancer Res. 2007; 67(11):5371-9) was reported to inhibit tumor growth in vivo. Therefore, tumors isolated from MMTV-Wnt1 transgenic mice were passaged subcutaneously as tumor pieces in nude mice for 2 to 5 passages prior to initiation of the efficacy experiment. Between 14 to 21 days post-implant, when tumors reached a mean volume of approximately 150 to 250 $mm^3$, mice were randomized into groups with 7 mice per group and dosed i.v. with the compounds. The LRP5/LRP6 cross-reactive biparatopic half-life extended VHH constructs were administered to the mice i.v. twice per week, with the dosages shown in FIG. 7A for F013500571 and in FIG. 7B for F013500720. Comparative compound Knob HC YW210.09 was also dosed i.v. twice per week, but at higher doses, i.e. 30 and 45 mg/kg (FIG. 7C), due to the data obtained with this compound in the in vitro experiments explained above. Tumor volume and body weight were monitored during the efficacy experiment and the median tumor volumes are reported in FIGS. 7A to 7C. Tumor growth inhibition (TGI) was determined at the end of the efficacy experiment. In particular, TGI was determined for each treatment group as compared to the control group (treatment of mice with histidine buffer—20 mM Histidine pH6.5 buffer—in the experiment shown in FIGS. 7A and 7B, or with citrate buffer for the experiment shown in FIG. 7C). Furthermore, gastro-intestinal (GI) histo-pathological analysis (via H&E staining of sections of the GI tract from the duodenum to the rectum) was performed at the end of the efficacy experiment to evaluate potential toxicity of the LRP5 and LRP6 antagonists. Tumor growth inhibition (TGI), outcome of the GI histo-pathological analysis at the end of the in vivo efficacy study, mortality which corresponds to the number of mice that needed to be scarified due to significant loss of body weight (>18% loss of body weight compared to start of the efficacy experiment) and number of tumor regressions (tumor volume at the end of the experiment smaller than tumor volume measure at the start of the treatment) are reported for each treatment group in Tables XIIA, XIIB, and XIIC, relating to the experiments and data shown also in FIGS. 7A, 7B and 7C, respectively.

TABLE XIIA

Figure 7A:
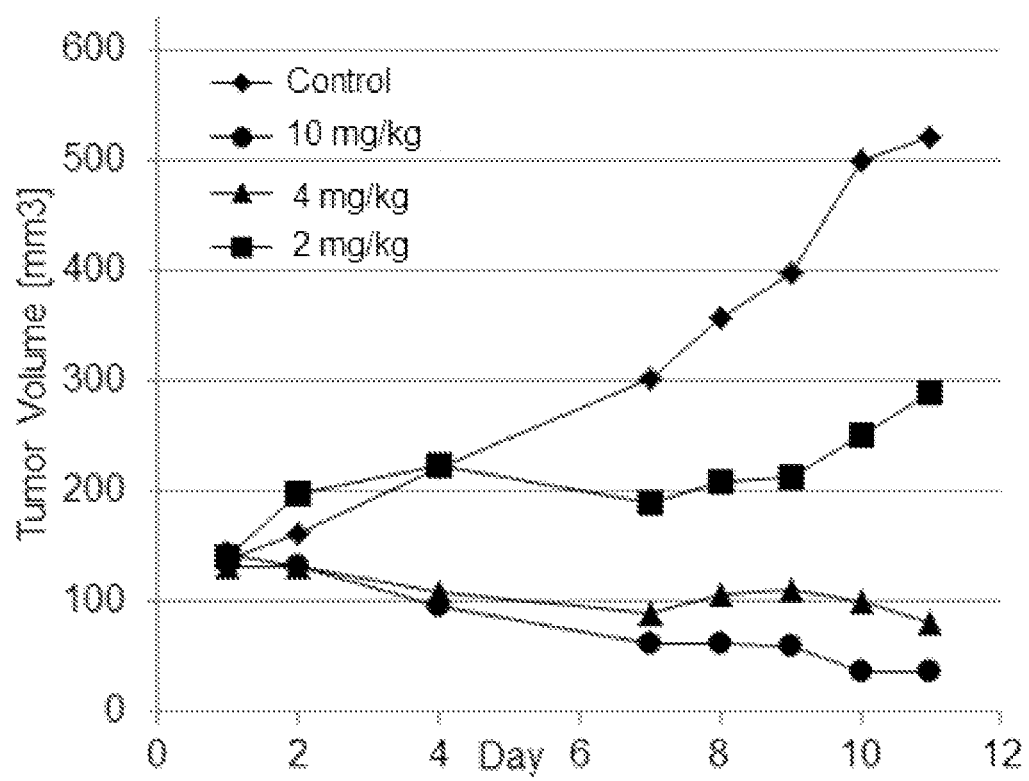
FIGS. 7A, 7B and 7C.

In vivo efficacy of F013500571 administered i.v. twice per week. Results of this experiment are also shown in FIG. 7A

|  | Dose [mg/kg] | TGI [%] | Regressions [x/7] | Mortality [x/7] | GI Histopathological evaluation |
|---|---|---|---|---|---|
| Control | Histidine buffer | — | — | — | — |
| F013500571 | 10 | 128 | 7 | 0 | No findings |
|  | 4 | 113 | 7 | 0 | No findings |
|  | 2 | 61 | 0 | 0 | n.d. |

TABLE XIIB

Figure 7B:
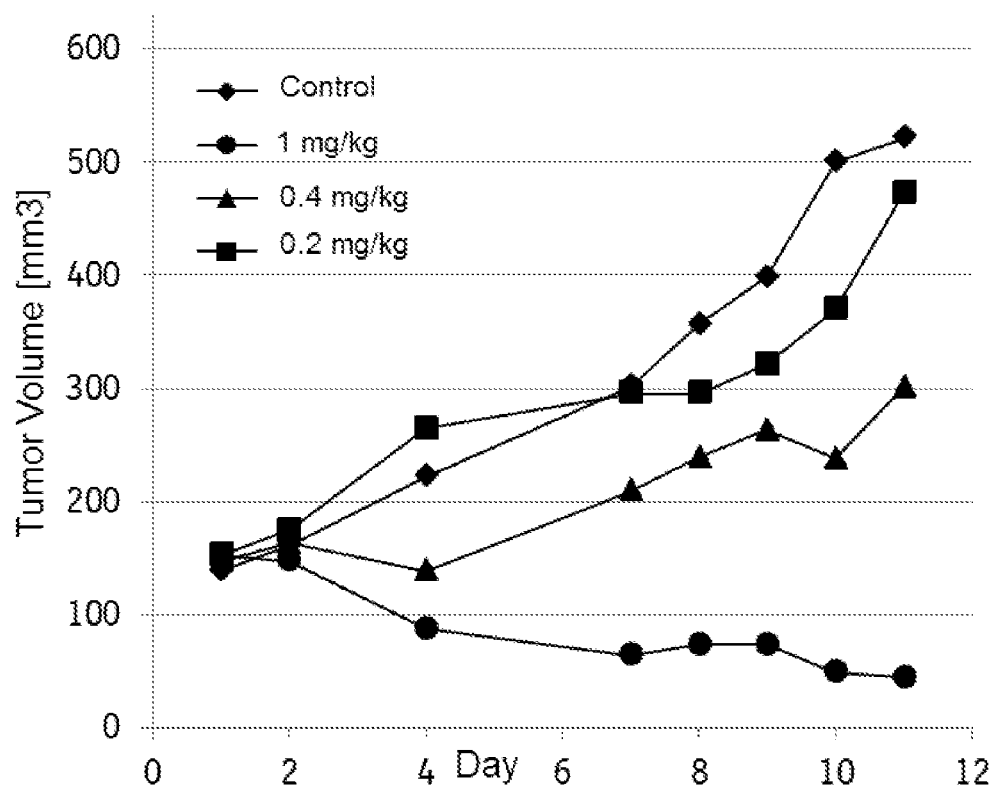

In vivo efficacy of F013500720 administered i.v. twice per week. Results of this experiment are also shown in FIG. 7B

|  | Dose [mg/kg] | TGI [%] | Regressions [x/7] | Mortality [x/7] | GI Histopathological evaluation |
|---|---|---|---|---|---|
| Control | Histidine buffer | — | — | — | — |
| F013500720 | 1 | 128 | 7 | 0 | No findings |
|  | 0.4 | 60 | 0 | 0 | No findings |
|  | 0.2 | 17 | 0 | 0 | n.d. |

TABLE XIIC

In vivo efficacy of Knob HC YW210.09 administered i.v. twice per week. Results of this experiment are also shown in FIG. 7C

| i.v. | Dose [mg/kg] | TGI [%] | Regressions [x/7] | Mortality [x/7] | GI Histopathological evaluation |
|---|---|---|---|---|---|
| Control | Citrate buffer | — | — | — | — |
| Knob HC YW210.09 | 30 | 80 | 0 | 0 | — |
|  | 45 | 85 | 0 | 0 | No findings |

Figure 7C:
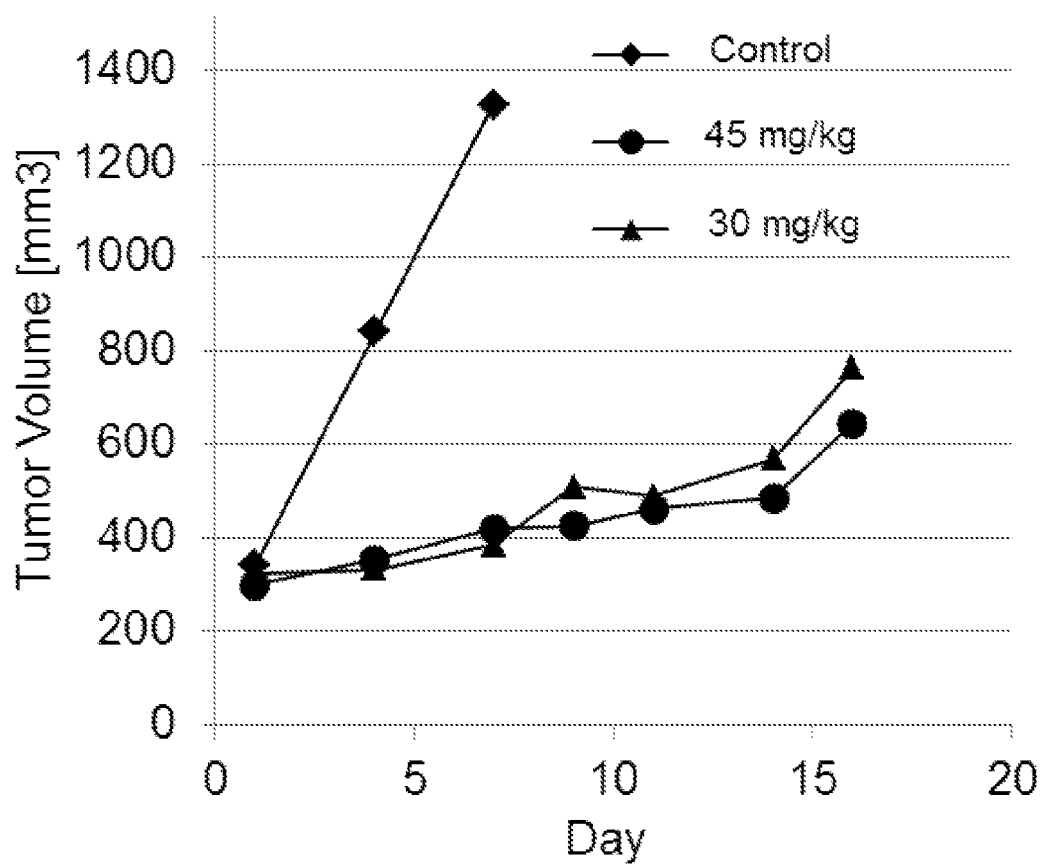

As can be taken from FIGS. 7A to 7C and Tables XIIA to XIIC above, treatment with the LRP5/LRP6 cross-reactive half-life extended biparatopic VHH constructs (F013500571 at 4 and 10 mg/kg and F013500720 at 1 mg/kg in a 2×/week schedule) indeed resulted in tumor regression (i.e. tumor growth inhibition (TGI)>100% which corresponds to tumor shrinkage; decrease of the tumor volume at the end of the efficacy experiment compared to the tumor volume at the start of the experiment), with no significant body weight changes (<10%) and no findings reported after GI histopathological analysis. Importantly, in contrast thereto, no tumor regression could be observed upon treatment with the LRP6 specific binder Knob HC YW210.09, even at the maximum administrable i.v. dose/schedule in mice, which correspond to 90 mg/kg with 3×/week schedule.

To further investigate the differences in in vivo efficacy as observed in the experiment explained above, a further experiment was set up allowing more frequent administration (three times/week) of an even higher dose of the comparative compound to the mice. In brief, in order to achieve such higher exposure, the comparative compound was administered i.p., as indicated in the following Table XIID:

TABLE XIID

In vivo efficacy of Knob HC YW210.09 administered i.p. twice or three times per week, as indicated.

| i.p. | Dose [mg/kg] | Schedule | TGI [%] | Regressions [x/5] | Mortality [x/5] |
|---|---|---|---|---|---|
| Control | Citrate buffer | Three times/week | — | — | — |
| Knob HC YW210.09 | 45 | Twice/week | 55 | 1 | 0 |
|  | 90 | Twice week | 85 | 0 | 0 |
|  | 90 | Three times/week | 87 | 0 | 0 |

As can be seen from the data shown in Table XIID, also in this setting no significantly stronger effect was obtained in terms of TGI. In other words, these experiments, data and results clearly indicate a higher efficacy of the half-life extended biparatopic VHH constructs when compared to Knob HC YW210.09, and an unprecedented capability of the polypeptides of the invention to not only reduce tumor growth, but to even induce tumor shrinkage. Of course, tumor shrinkage (i.e. tumor regression) is the desired therapeutic effect (i.e. efficacy) for treatment of cancer patients. Indeed, in clinical studies treatments that induce tumor regression resulting in pathological complete response (pCR) positively lead to significant improvement of progression free survival and overall survival in high unmet medical need indications such as in breast cancer.

The above comparative examples also show that the LRP5/LRP6 cross-reactive biparatopic half-life extended VHH constructs are not only superior in terms of their binding characteristics, such as affinity or $K_D$ values, but that they have highly advantageous and superior properties in an in vivo setting.

Next, it was investigated whether compound MOR08168IgG1LALA 6475 scfv may provide for a similar advantageous effect. For this purpose an in vivo tolerability study was performed in mice as follows: MOR08168IgG1LALA 6475 scfv compound was administered i.v. at 3 mg/kg, twice per week (2qw); the same dose/regimen at which in vivo efficacy was detected in a xenograft tumor model in WO2011/138391, as described in FIG. 22 therein. First treatment with MOR08168IgG1LALA 6475 scfv was performed at day 1 and starting from day 6 significant loss of body weight was detected in mice. At day 10, some of the mice treated with MOR08168IgG1LALA 6475 scfv compound showed significant body weight loss (>10%). At day 11 mice were sacrificed and gastro-intestinal (GI) histopathological analysis revealed inflammation with erosion in the colon and in the cecum of the mice. These data suggest that MOR08168IgG1LALA 6475 scfv is not tolerated at the efficacious dose/regimen. Therefore, LRP5/LRP6 cross-reactive biparatopic half-life extended VHH constructs are superior with regard to therapeutic window; i.e. they induce tumor regression with no significant body weight changes (<10%) and no findings reported after GI histopathological analysis.

Example 10: In Vivo Wnt Pathway Inhibition

To further characterize the effect of the LRP5/LRP6 cross-reactive biparatopic half-life extended VHH constructs/binding molecules on Wnt signaling, tumors were isolated at the end of the efficacy experiment, described in Example 9. In particular, tumors were isolated 16 hours after the last injection with the compounds or with the control treatment. Wnt signaling inhibition was determined by reduction of mRNA expression of Axin2 in tumors, analysed as described in Example 8. The fold change of Axin2 mRNA expression relative to the control group is reported in FIG. 8A for the in vivo efficacy with F013500571 and in FIG. 8B for the in vivo efficacy with F013500720. Quantification of Axin2 mRNA reduction for each treatment group is reported in Tables XIIIA and XIIIB below.

TABLE XIIIA

Reduction of Axin2 mRNA expression in tumors by treatment with F013500571. The data refers to FIG. 7A and 8A.

|  | Dose [mg/kg] | TGI [%] | Axin2 reduction (%) |
|---|---|---|---|
| Control | Histidine buffer | — |  |
| F013500571 | 10 | 128 | 83 |
|  | 4 | 113 | 77 |
|  | 2 | 61 | 35 |

TABLE XIIIB

Reduction of Axin2 mRNA expression in tumors by treatment with F013500720. The data refers to FIG. 7B and 8B.

|  | Dose [mg/kg] | TGI [%] | Axin2 reduction (%) |
|---|---|---|---|
| Control | Histidine buffer | — |  |
| F013500720 | 1 | 128 | 92 |
|  | 0.4 | 60 | −21 |
|  | 0.2 | 17 | 35 |

Figure 8A:
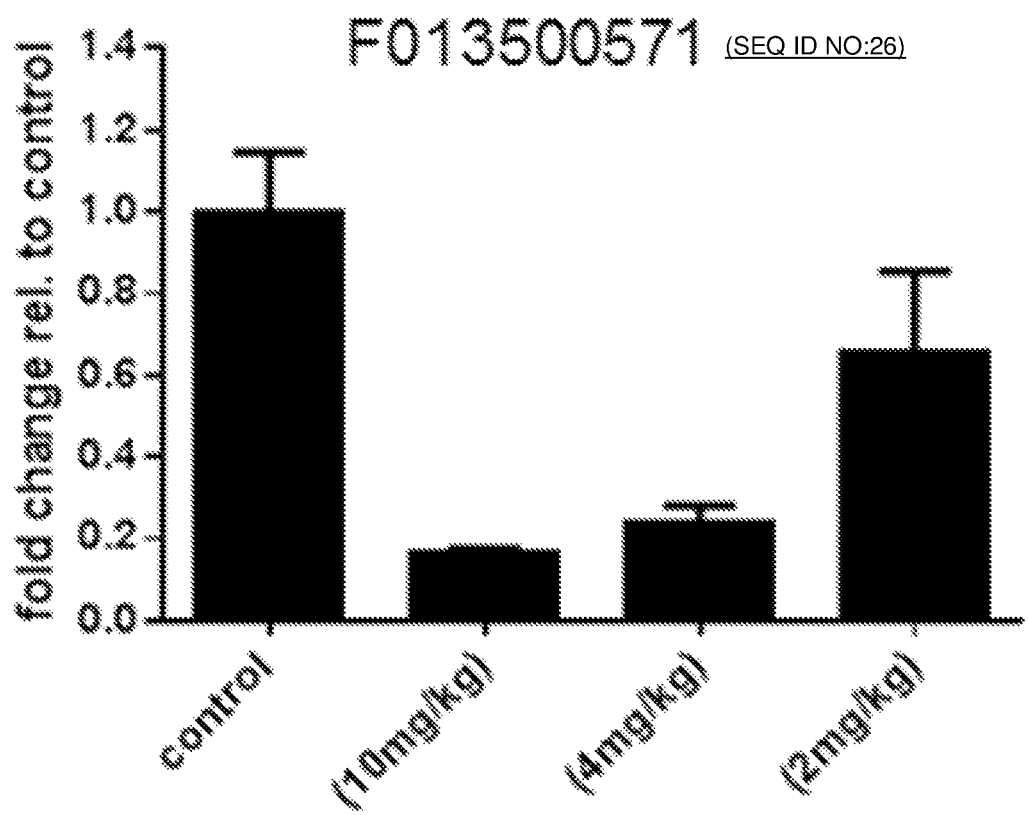
FIGS. 8A and 8B.
Figure 8B:
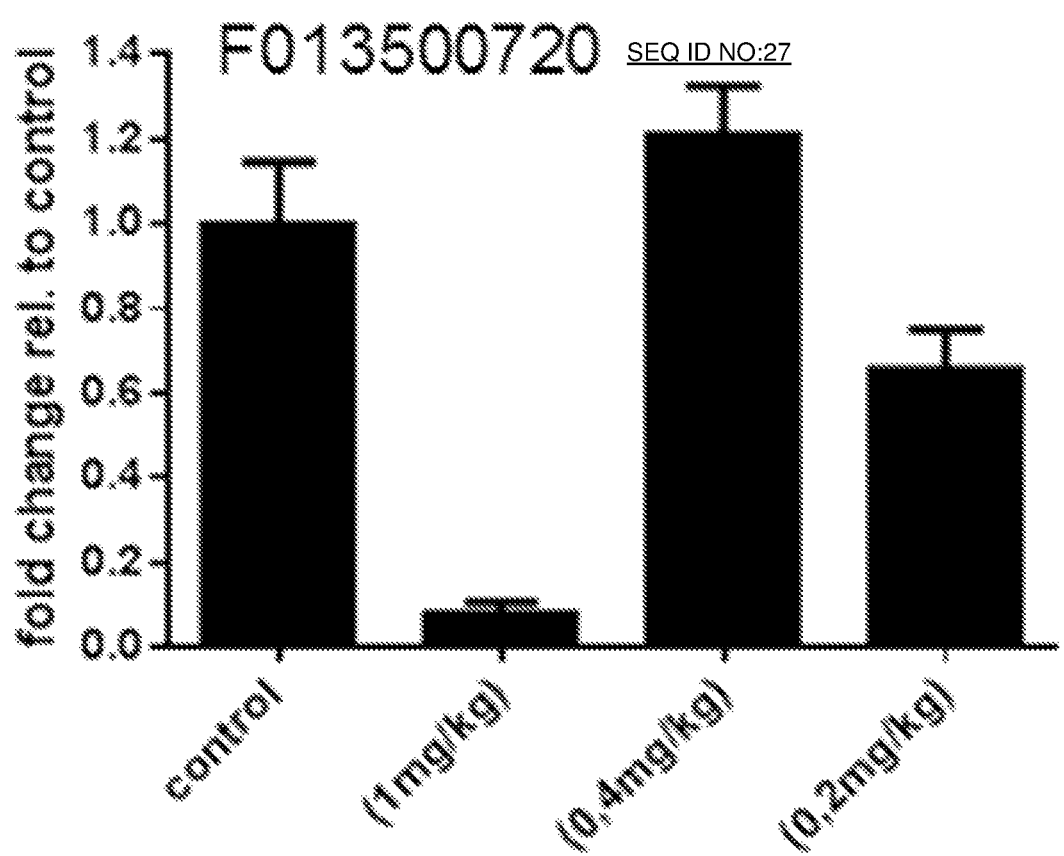

As can be seen from FIGS. 8A and 8B and Tables XIIIA and XIIIB, a significant reduction and dose dependent decrease (in particular for treatment with F013500571) of Axin2 mRNA expression was observed in tumors treated with the LRP5/LRP6 cross-reactive binding molecules, compared to the control group. These results suggest that the LRP5/LRP6 cross-reactive binding molecules are indeed able to inhibit tumor growth by suppressing Wnt signaling in the tumor cells.

Example 11: Industrial Manufacturing Process 11.1 Fermentation:

Any of the polypeptides set out in Tables III and V above can be expressed in the cytoplasm of different *E. coli* strains like W3110, TG1, BL21, BL21(DE3), HMS174, HMS174 (DE3), MM294 under control of an inducible promoter. This promoter can be chosen from lacUV5, tac, T7, trp, T5, araB. The cultivation media are preferably fully defined according to Wilms et al., 2001 (Wilms, B., Hauck, A., Reuss, M., Syldatk, C., Mattes, R., Siemann, M., and Altenbuchner, J.: High-Cell-Density Fermentation for Production of L-N-Carbamoylase Using an Expression System Based on the *Escherichia coli* rhaBAD Promoter. Biotechnology and Bioengineering, 73: 95-103 (2001)), DeLisa et al., 1999 (DeLisa, M. P., Li, J. C., Rao, G., Weigand, W. A., and Bentley, W. E.: Monitoring GFP-operon fusion protein expression during high cell density cultivation of *Escherichia coli* using an on-line optical sensor. Biotechnology and Bioengineering, 65: 54-64. (1999)) or equivalent. However, supplementation of the medium with amino acids like isoleucine, leucine, lysine, methionine, phenylalanine, threonine, tryptophan and valin or complex media components such as soy peptone or yeast extract may be beneficial. The process for fermentation is performed in a fed-batch mode. Conditions: Temperature 30-40° C., pH 6-7.5, dissolved oxygen is kept above 20%. After consumption of the initial C-source the culture is fed with the feed media stated above (or equivalent). When a dry cell weight in the fermenter of 40 to 90 g/L is reached the culture is induced with an appropriate inducer corresponding to the used promoter system (e.g. IPTG, lactose, arabinose). The induction can either be performed as a pulsed full induction or as a partial induction by feeding the respective inducer into the fermenter over a prolonged time. The production phase should last 4 hours at least. The cells are recovered by centrifugation in bowl centrifuges, tubular bowl centrifuges or disc stack centrifuges, the culture supernatant is discarded.

11.2 Purification:

The *E. coli* cell mass is resuspended in 6- to 8-fold amount of lysis buffer (phosphate or Tris buffer, pH 7-8.5). Cell lysis is preferably performed by high pressure homogenization followed by removing of the cell debris by centrifugation in bowl, tubular bowl or disc stack centrifuges. Supernatant containing the target protein is optionally filtrated using a 0.22-10 μm filter and separated via cation exchange chromatography (e.g. TOYOPEARL MEGACAP® II SP-550EC, TOYOPEARL GIGACAP® S-650M, SP SEPHAROSE® BB, SP SEPHAROSE® FF or S HYPERCELI™ sorbent) at pH 7-8.5. Elution is performed by a linear increasing NaCl gradient at pH 7-8.5. Fractions containing the target protein are pooled and subsequently incubated with 5-10 mM DTT in order to prevent dimerization or aggregation mediated by free cysteine residues. After further addition of 0.8-1 M ammonium sulfate or 2-3 M NaCl, solution is separated via hydrophilic interaction chromatography (e.g. Phenyl SEPHAROSE @ HP, Phenyl SEPHAROSE® FF, Butyl SEPHAROSE® HP, Butyl SEPHAROSE® FF, Butyl TOYOPEARL GIGACAP® 650 (S,M,C), Phenyl TOYOPEARL GIGACAP® 650 (S,M,C) sorbent) at pH 7-8.5. Elution is carried out at pH 7-8.5 by a linear decreasing ammonium sulfate or NaCl gradient in presence of 5 mM DTT. Fractions containing the target protein with a purity level of minimally 90% are pooled and desalted by diafiltration in presence of 5 mM DTT followed by concentration to approximately 5 mg/ml. Subsequent refolding is performed by diluting the protein solution 1:5-1:20 with 50 mM Tris, 150 mM NaCl, 4 mM Cystamin, 10 mM CHAPS at pH 8.5 to a final protein concentration of 0.25-1 mg/ml. Refolding solution is incubated under stirring for 12-36 h at room temperature and then separated by cation exchange chromatography (e.g. SP SEPHAROSE® FF, SP SEPHAROSE® HP, TOYOPEARL GIGACAP® SP-650 (S, M, C)) at pH 7-8.5. Elution is performed by a linear increasing NaCl gradient at pH 7-8.5. Fractions containing monomeric target protein are pooled and formulated in 25 mM Na-phosphate, 220 mM endotoxin free trehalose, pH 7.5 via diafiltration. The solution is sterilized by filtration and stored at 2 to 8° C.

Example 12: Pharmaceutical Formulation for s.c. Administration

Any of the above biparatopic polypeptide constructs of the invention can be selected for the manufacture of a pharmaceutical formulation for subcutaneous application having a composition as follows:

Drug substance: 100 mg/ml (1 to 3 nmol/ml)
Acetate buffer: 25 mM
Trehalose: 220 mM
TWEEN®-20 viscous liquid (Sigma Aldrich): 0.02%
Drug substance is formulated in a solution having the above composition, sterilized and stored at 2 to 8° C.

Example 13: Pharmaceutical Use in Humans

The solution as prepared in Example 11.2 above is applied to a patient in need thereof, such as a human being suffering from a cancer sensitive to Wnt signaling inhibitors, by intravenous infusion (dosage of 100 to 200 mg) every two to four weeks.

Figure 9A:
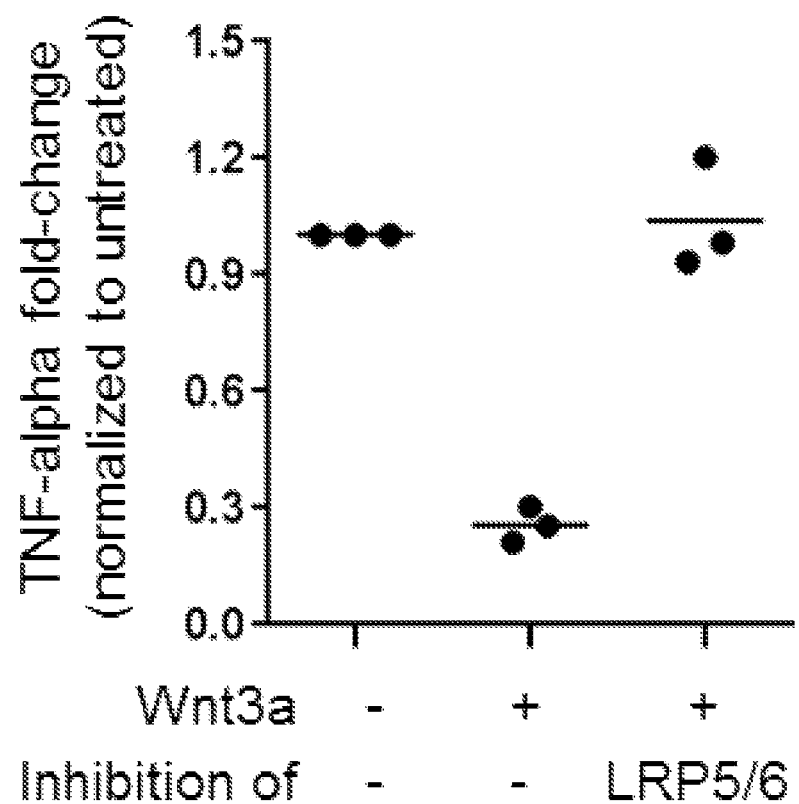
FIGS. 9A and 9B.

Example 14: Effect of Wnt3a-Signaling Inhibition on Pro-Inflammatory Cytokine Release by Dendritic Cells in an Ex-Vivo Assay PBMCs were obtained from healthy donors with informed consent. Human monocyte-derived dendritic cells (Mo-DCs) were generated as follows: PBMCs were cultured in X-VIVO medium supplemented with 50 ng/mL GM-CSF and 50 ng/mL IL-4. After 24 h of culture, the supernatant was carefully removed and replaced with X-VIVO™ medium supplemented with the same GM-CSF and IL-4. On the fourth day, the supernatant was carefully removed and replaced with X-VIVO medium in the presence of LPS only or in combination with human Wnt3a or with human Wnt3a and LRP5/LRP6 cross-reactive binding molecules. On the following day, the supernatants were collected and subjected to analysis of TNF-alpha through ELISA according to the manufacturer's instructions. As previously reported (Oderup et al. "Canonical and noncanonical Wnt proteins program dendritic cell responses for tolerance". *J Immunol.* 2013; 190(12): 6126-34), and as shown in FIG. 9A, Wnt3a directly inhibits pro-inflammatory cytokine secretion (i.e. TNF-alpha release) by differentiated dendritic cells (DCs). Wnt3a driven suppression of TNF-alpha release from DCs was restored by addition of LRP5/LRP6 cross-reactive binding molecules.

These data show that the formatted, biparatopic, and sequence-optimized binding molecules are able to restore TNFalpha secretion by Wnt3a treated dendritic cells, thereby suppressing the Wnt inhibitory effect on dendritic cells.

It is important to notice that blocking the Wnt pathway in dendritic cells in the tumor microenviroment might represents a potential therapeutic approach towards breaking tumor-mediated immune suppression and augmenting anti-tumor immunity.

To investigate the effects of DCs on T cells (effector T cells), DCs pre-treated with Wnt3a with or without LRP5/LRP6 cross-reactive binding molecules were co-cultured with T cells, isolated from PBMCs, as previously described (Oderup et al. "Canonical and noncanonical Wnt proteins program dendritic cell responses for tolerance". *J Immunol.* 2013; 190(12): 6126-34). After 3 days of DC/T cells co-culture, the supernatants were collected and subjected to analysis of IFN gamma through ELISA, according to the manufacturer's instructions.

Figure 9B:
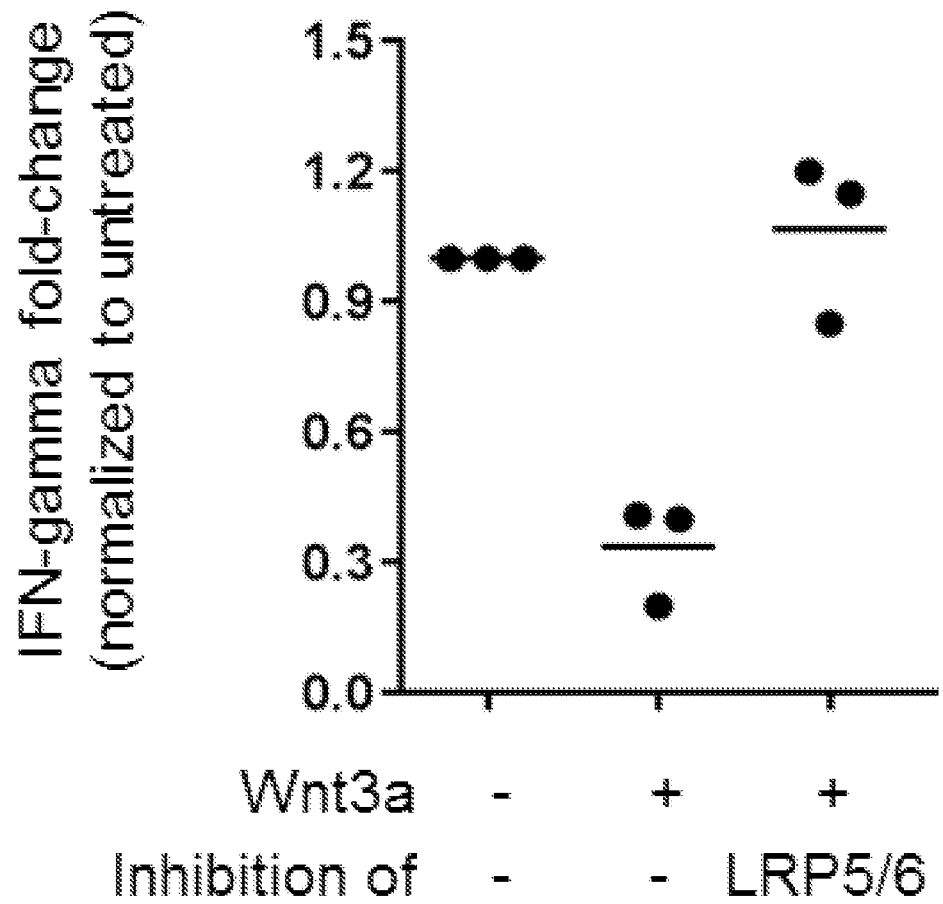

IFNgamma secretion is a marker of T cell activation. As shown in FIG. 9B, Wnt3a mediated DC inhibition leads to reduced IFNgamma secretion by T cells (inhibition of T cell function), which is completely restored by treatment with LRP5/LRP6 cross-reactive binding molecules.

In summary, these data show that LRP5/LRP6 cross-reactive binding molecules suppress the Wnt inhibitory effect on dendritic cells, leading to restoration of T cell function.

It is known that continuous activation/stimulation of T cells induces terminal differentiation, resulting in an exhausted T cell phenotype, a progressive loss of T-cell function. Therefore, it is envisaged that the effect of LRP5/LRP6 cross-reactive binding molecules on T cells, mediated by activation of DCs, might be limited by T cell exhaustion. Combination treatments, combining the administration of LRP5/LRP6 cross-reactive binding molecules with the administration of an immune checkpoint inhibitor which blocks T cell exhaustion, are therefore expected to help to activate and maintain T cell function, thereby changing the tumor microenvironment, and thereby supporting the therapeutic effect of the molecules of the invention.

The invention claimed is:

1. A method of treatment of tumors expressing human LRP5 and/or human LRP6 by inhibition of the Wnt-1 and/or Wnt-3a signaling pathways in a cancer patient comprising administering to said patient a cross-reactive biparatopic polypeptide which specifically binds to an epitope of the human low-density receptor-like protein 5 (LRP5) as well as an epitope of the human low-density receptor-like protein 6 (LRP6) in an amount effective to reduce said patient's tumor burden and/or tumor size wherein said cross-reactive biparatopic polypeptide comprises:
   (a) a first immunoglobulin single variable domain, wherein said immunoglobulin single variable domain is a humanized VHH domain capable of inhibiting the Wnt1 signaling pathway comprising the CDR sequences:

```
                                          (SEQ ID NO: 4)
    CDR1: SYAMG
                                          (SEQ ID NO: 5)
    CDR2: AIRRSGRRTYYADSVKG
    and
                                          (SEQ ID NO: 6)
    CDR3: ARRVRSSTRYNTGTWWWEY;
```
   and
   (b) a second immunoglobulin single variable domain wherein said second immunoglobulin single variable domain is a humanized VHH domain capable of inhibiting the Wnt3a signaling pathway comprising the following CDR sequences:

```
                                          (SEQ ID NO: 13)
    CDR1: SYAMG
                                          (SEQ ID NO: 14)
    CDR2: AISWRSGSTYYADSVKG
    and
                                          (SEQ ID NO: 15)
    CDR3: DPRGYGVAYVSAYYEY.
``` wherein said first and said second immunoglobulin single variable domains are covalently linked by a linker peptide, wherein said linker peptide comprises a third immunoglobulin single variable domain which binds to albumin comprising SEQ ID NO:24.

2. The method of claim 1, wherein the cross-reactive biparatopic polypeptide comprises
   a first immunoglobulin single variable domain comprising the amino acid sequence SEQ ID NO: 20 and
   a second immunoglobulin single variable domain comprising the amino acid sequence SEQ ID NO:23.

3. The method of claim 2, wherein the cross-reactive biparatopic polypeptide comprises SEQ ID NO: 26.

* * * * *

SEQUENCE LISTING

```
<160> NUMBER OF SEQ ID NOS: 59

<210> SEQ ID NO 1
<211> LENGTH: 5
<212> TYPE: PRT
<213> ORGANISM: Artificial Sequence
<220> FEATURE:
<223> OTHER INFORMATION: CDR1 of Wnt1-333E06mod

<400> SEQUENCE: 1

Thr Tyr Thr Val Gly
1               5

<210> SEQ ID NO 2
<211> LENGTH: 17
<212> TYPE: PRT
<213> ORGANISM: Artificial Sequence
<220> FEATURE:
<223> OTHER INFORMATION: CDR2 of Wnt1-333E06mod

<400> SEQUENCE: 2

Ala Ile Arg Arg Arg Gly Ser Ser Thr Tyr Tyr Ala Asp Ser Val Lys
```

Gly

<210> SEQ ID NO 3
<211> LENGTH: 14
<212> TYPE: PRT
<213> ORGANISM: Artificial Sequence
<220> FEATURE:
<223> OTHER INFORMATION: CDR3 of Wnt1-333E06mod

<400> SEQUENCE: 3

Asp Thr Arg Thr Val Ala Leu Leu Gln Tyr Arg Tyr Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: CDR1 of Wnt1-333G06

<400> SEQUENCE: 4

Ser Tyr Ala Met Gly
1               5

<210> SEQ ID NO 5
<211> LENGTH: 17
<212> TYPE: PRT
<213> ORGANISM: Artificial Sequence
<220> FEATURE:
<223> OTHER INFORMATION: CDR2 of Wnt1-333G06

<400> SEQUENCE: 5

Ala Ile Arg Arg Ser Gly Arg Arg Thr Tyr Tyr Ala Asp Ser Val Lys
1               5                   10                  15

Gly

<210> SEQ ID NO 6
<211> LENGTH: 19
<212> TYPE: PRT
<213> ORGANISM: Artificial Sequence
<220> FEATURE:
<223> OTHER INFORMATION: CDR3 of Wnt1-333G06

<400> SEQUENCE: 6

Ala Arg Arg Val Arg Ser Ser Thr Arg Tyr Asn Thr Gly Thr Trp Trp
1               5                   10                  15

Trp Glu Tyr

<210> SEQ ID NO 7
<211> LENGTH: 5
<212> TYPE: PRT
<213> ORGANISM: Artificial Sequence
<220> FEATURE:
<223> OTHER INFORMATION: CDR1 of Wnt1-332D03mod

<400> SEQUENCE: 7

Arg Tyr Thr Met Gly
1               5

<210> SEQ ID NO 8
<211> LENGTH: 17
<212> TYPE: PRT
<213> ORGANISM: Artificial Sequence
<220> FEATURE:

```
<223> OTHER INFORMATION: CDR2 of Wnt1-332D03mod

<400> SEQUENCE: 8

Ala Ile Val Arg Ser Gly Gly Ser Thr Tyr Tyr Ala Asp Ser Val Lys
1               5                   10                  15

Gly

<210> SEQ ID NO 9
<211> LENGTH: 20
<212> TYPE: PRT
<213> ORGANISM: Artificial Sequence
<220> FEATURE:
<223> OTHER INFORMATION: CDR3 of Wnt1-332D03mod

<400> SEQUENCE: 9

Asp Arg Arg Gly Arg Gly Glu Asn Tyr Ile Leu Leu Tyr Ser Ser Gly
1               5                   10                  15

Arg Tyr Glu Tyr
            20

<210> SEQ ID NO 10
<211> LENGTH: 5
<212> TYPE: PRT
<213> ORGANISM: Artificial Sequence
<220> FEATURE:
<223> OTHER INFORMATION: CDR1 of Wnt3a-093A01

<400> SEQUENCE: 10

Ser Tyr Ala Met Gly
1               5

<210> SEQ ID NO 11
<211> LENGTH: 17
<212> TYPE: PRT
<213> ORGANISM: Artificial Sequence
<220> FEATURE:
<223> OTHER INFORMATION: CDR2 of Wnt3a-093A01

<400> SEQUENCE: 11

Ala Ile Ser Trp Ser Gly Gly Ser Thr Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: CDR3 of Wnt3a-093A01

<400> SEQUENCE: 12

Ser Pro Ile Pro Tyr Gly Ser Leu Leu Arg Arg Arg Asn Asn Tyr Asp
1               5                   10                  15

Tyr

<210> SEQ ID NO 13
<211> LENGTH: 5
<212> TYPE: PRT
<213> ORGANISM: Artificial Sequence
<220> FEATURE:
<223> OTHER INFORMATION: CDR1 of Wnt3a-367B10

<400> SEQUENCE: 13

Ser Tyr Ala Met Gly
```

```
<210> SEQ ID NO 14
<211> LENGTH: 17
<212> TYPE: PRT
<213> ORGANISM: Artificial Sequence
<220> FEATURE:
<223> OTHER INFORMATION: CDR2 of Wnt3a-367B10

<400> SEQUENCE: 14

Ala Ile Ser Trp Arg Ser Gly Ser Thr Tyr Tyr Ala Asp Ser Val Lys
1               5                   10                  15
Gly

<210> SEQ ID NO 15
<211> LENGTH: 16
<212> TYPE: PRT
<213> ORGANISM: Artificial Sequence
<220> FEATURE:
<223> OTHER INFORMATION: CDR3 of Wnt3a-367B10

<400> SEQUENCE: 15

Asp Pro Arg Gly Tyr Gly Val Ala Tyr Val Ser Ala Tyr Tyr Glu Tyr
1               5                   10                  15

<210> SEQ ID NO 16
<211> LENGTH: 5
<212> TYPE: PRT
<213> ORGANISM: Artificial Sequence
<220> FEATURE:
<223> OTHER INFORMATION: CDR1 of Alb11

<400> SEQUENCE: 16

Ser Phe Gly Met Ser
1               5

<210> SEQ ID NO 17
<211> LENGTH: 17
<212> TYPE: PRT
<213> ORGANISM: Artificial Sequence
<220> FEATURE:
<223> OTHER INFORMATION: CDR2 of Alb11

<400> SEQUENCE: 17

Ser Ile Ser Gly Ser Gly Ser Asp Thr Leu Tyr Ala Asp Ser Val Lys
1               5                   10                  15
Gly

<210> SEQ ID NO 18
<211> LENGTH: 6
<212> TYPE: PRT
<213> ORGANISM: Artificial Sequence
<220> FEATURE:
<223> OTHER INFORMATION: CDR3 of Alb11

<400> SEQUENCE: 18

Gly Gly Ser Leu Ser Arg
1               5

<210> SEQ ID NO 19
<211> LENGTH: 123
<212> TYPE: PRT
<213> ORGANISM: Artificial Sequence
<220> FEATURE:
<223> OTHER INFORMATION: VHH domain Wnt1-333E06mod
```

```
<400> SEQUENCE: 19

Ala Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Thr Val Gly Trp Phe Arg Gln Ala Pro Gly Lys Glu Arg Glu Phe Val
        35                  40                  45

Ala Ala Ile Arg Arg Arg Gly Ser Ser Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Thr Arg Thr Val Ala Leu Leu Gln Tyr Arg Tyr Asp Tyr
            100                 105                 110

Trp Gly Gln Gly Thr Leu Val Thr Val Ser Ser
        115                 120

<210> SEQ ID NO 20
<211> LENGTH: 128
<212> TYPE: PRT
<213> ORGANISM: Artificial Sequence
<220> FEATURE:
<223> OTHER INFORMATION: VHH domain Wnt1-333G06

<400> SEQUENCE: 20

Ala Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Arg Arg Ser Gly Arg Arg Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Arg Arg Val Arg Ser Ser Thr Arg Tyr Asn Thr Gly Thr
            100                 105                 110

Trp Trp Trp Glu Tyr Trp Gly Gln Gly Thr Leu Val Thr Val Ser Ser
        115                 120                 125

<210> SEQ ID NO 21
<211> LENGTH: 129
<212> TYPE: PRT
<213> ORGANISM: Artificial Sequence
<220> FEATURE:
<223> OTHER INFORMATION: VHH domain Wnt1-332D03mod

<400> SEQUENCE: 21

Ala Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Thr Met Gly Trp Phe Arg Gln Ala Pro Gly Lys Glu Arg Glu Phe Val
        35                  40                  45
```

```
Ala Ala Ile Val Arg Ser Gly Gly Ser Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Asp Arg Arg Gly Arg Gly Glu Asn Tyr Ile Leu Leu Tyr Ser
            100                 105                 110

Ser Gly Arg Tyr Glu Tyr Trp Gly Gln Gly Thr Leu Val Thr Val Ser
            115                 120                 125

Ser

<210> SEQ ID NO 22
<211> LENGTH: 126
<212> TYPE: PRT
<213> ORGANISM: Artificial Sequence
<220> FEATURE:
<223> OTHER INFORMATION: VHH domain Wnt3a-093A01

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Ser Tyr
             20                  25                  30

Ala Met Gly Trp Phe Arg Gln Ala Pro Gly Lys Glu Arg Glu Phe Val
         35                  40                  45

Ala Ala Ile Ser Trp Ser Gly Gly Ser Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Ser Pro Ile Pro Tyr Gly Ser Leu Leu Arg Arg Arg Asn Asn
            100                 105                 110

Tyr Asp Tyr Trp Gly Gln Gly Thr Leu Val Thr Val Ser Ser
            115                 120                 125

<210> SEQ ID NO 23
<211> LENGTH: 125
<212> TYPE: PRT
<213> ORGANISM: Artificial Sequence
<220> FEATURE:
<223> OTHER INFORMATION: VHH domain Wnt3a-367B10

<400> SEQUENCE: 23

Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Thr Phe Ser Ser Tyr
             20                  25                  30

Ala Met Gly Trp Phe Arg Gln Ala Pro Gly Lys Glu Arg Glu Phe Val
         35                  40                  45

Ala Ala Ile Ser Trp Arg Ser Gly Ser Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                 85                  90                  95
```

```
Ala Ala Asp Pro Arg Gly Tyr Gly Val Ala Tyr Val Ser Ala Tyr Tyr
            100                 105                 110

Glu Tyr Trp Gly Gln Gly Thr Leu Val Thr Val Ser Ser
        115                 120                 125

<210> SEQ ID NO 24
<211> LENGTH: 115
<212> TYPE: PRT
<213> ORGANISM: Artificial Sequence
<220> FEATURE:
<223> OTHER INFORMATION: VHH domain Alb11

<400> SEQUENCE: 24

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 25
<211> LENGTH: 435
<212> TYPE: PRT
<213> ORGANISM: Artificial Sequence
<220> FEATURE:
<223> OTHER INFORMATION: VHH construct F013500575

<400> SEQUENCE: 25

Ala Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Thr Val Gly Trp Phe Arg Gln Ala Pro Gly Lys Glu Arg Glu Phe Val
        35                  40                  45

Ala Ala Ile Arg Arg Gly Ser Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Thr Arg Thr Val Ala Leu Leu Gln Tyr Arg Tyr Asp Tyr
            100                 105                 110

Trp Gly Gln Gly Thr Leu Val Thr Val Ser Ser Gly Gly Gly Ser
        115                 120                 125

Gly Gly Gly Gly Ser Gly Gly Gly Ser Gly Gly Gly Ser Gly
    130                 135                 140

Gly Gly Gly Ser Gly Gly Gly Ser Gly Gly Gly Gly Ser Glu Val
145                 150                 155                 160
```

Gln Leu Val Glu Ser Gly Gly Leu Val Gln Pro Gly Asn Ser Leu
                165                 170                 175

Arg Leu Ser Cys Ala Ala Ser Gly Phe Thr Phe Ser Ser Phe Gly Met
            180                 185                 190

Ser Trp Val Arg Gln Ala Pro Gly Lys Gly Leu Glu Trp Val Ser Ser
        195                 200                 205

Ile Ser Gly Ser Gly Ser Asp Thr Leu Tyr Ala Asp Ser Val Lys Gly
    210                 215                 220

Arg Phe Thr Ile Ser Arg Asp Asn Ala Lys Thr Thr Leu Tyr Leu Gln
225                 230                 235                 240

Met Asn Ser Leu Arg Pro Glu Asp Thr Ala Val Tyr Tyr Cys Thr Ile
                245                 250                 255

Gly Gly Ser Leu Ser Arg Ser Ser Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Ser Gly Gly Gly Ser Gly Gly Gly Ser Gly
    290                 295                 300

Gly Gly Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Arg Thr
                325                 330                 335

Phe Ser Ser Tyr Ala Met Gly Trp Phe Arg Gln Ala Pro Gly Lys Glu
            340                 345                 350

Arg Glu Phe Val Ala Ala Ile Ser Trp Ser Gly Gly Ser Thr Tyr Tyr
        355                 360                 365

Ala Asp Ser Val Lys Gly Arg Phe Thr Ile Ser Arg Asp Asn Ser Lys
    370                 375                 380

Asn Thr Val Tyr Leu Gln Met Asn Ser Leu Arg Pro Glu Asp Thr Ala
385                 390                 395                 400

Val Tyr Tyr Cys Ala Ala Ser Pro Ile Pro Tyr Gly Ser Leu Leu Arg
                405                 410                 415

Arg Arg Asn Asn Tyr Asp Tyr Trp Gly Gln Gly Thr Leu Val Thr Val
            420                 425                 430

Ser Ser Ala
        435

<210> SEQ ID NO 26
<211> LENGTH: 439
<212> TYPE: PRT
<213> ORGANISM: Artificial Sequence
<220> FEATURE:
<223> OTHER INFORMATION: VHH construct F013500571

<400> SEQUENCE: 26

Ala Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Arg Arg Ser Gly Arg Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

-continued

```
Leu Gln Met Asn Ser Leu Arg Pro Glu Asp Thr Ala Val Tyr Tyr Cys
                 85                  90                  95
Ala Ala Ala Arg Arg Val Arg Ser Ser Thr Arg Tyr Asn Thr Gly Thr
            100                 105                 110
Trp Trp Trp Glu Tyr Trp Gly Gln Gly Thr Leu Val Thr Val Ser Ser
        115                 120                 125
Gly Gly Gly Gly Ser Gly Gly Gly Ser Gly Gly Gly Gly Ser Gly
    130                 135                 140
Gly Gly Gly Ser Gly Gly Gly Ser Gly Gly Gly Ser Gly Gly
145                 150                 155                 160
Gly Gly Ser Glu Val Gln Leu Val Glu Ser Gly Gly Leu Val Gln
                165                 170                 175
Pro Gly Asn Ser Leu Arg Leu Ser Cys Ala Ala Ser Gly Phe Thr Phe
            180                 185                 190
Ser Ser Phe Gly Met Ser Trp Val Arg Gln Ala Pro Gly Lys Gly Leu
        195                 200                 205
Glu Trp Val Ser Ser Ile Ser Gly Ser Gly Ser Asp Thr Leu Tyr Ala
    210                 215                 220
Asp Ser Val Lys Gly Arg Phe Thr Ile Ser Arg Asp Asn Ala Lys Thr
225                 230                 235                 240
Thr Leu Tyr Leu Gln Met Asn Ser Leu Arg Pro Glu Asp Thr Ala Val
                245                 250                 255
Tyr Tyr Cys Thr Ile Gly Gly Ser Leu Ser Arg Ser Ser Gln Gly Thr
            260                 265                 270
Leu Val Thr Val Ser Ser Gly Gly Gly Ser Gly Gly Gly Gly Ser
        275                 280                 285
Gly Gly Gly Gly Ser Gly Gly Gly Ser Gly Gly Gly Gly Ser Gly
    290                 295                 300
Gly Gly Ser Gly Gly Gly Ser Glu Val Gln Leu Val Glu Ser
305                 310                 315                 320
Gly Gly Gly Leu Val Gln Pro Gly Gly Ser Leu Arg Leu Ser Cys Ala
                325                 330                 335
Ala Ser Gly Gly Thr Phe Ser Ser Tyr Ala Met Gly Trp Phe Arg Gln
            340                 345                 350
Ala Pro Gly Lys Glu Arg Glu Phe Val Ala Ala Ile Ser Trp Arg Ser
        355                 360                 365
Gly Ser Thr Tyr Tyr Ala Asp Ser Val Lys Gly Arg Phe Thr Ile Ser
    370                 375                 380
Arg Asp Asn Ser Lys Asn Thr Val Tyr Leu Gln Met Asn Ser Leu Arg
385                 390                 395                 400
Pro Glu Asp Thr Ala Val Tyr Tyr Cys Ala Ala Asp Pro Arg Gly Tyr
                405                 410                 415
Gly Val Ala Tyr Val Ser Ala Tyr Tyr Glu Tyr Trp Gly Gln Gly Thr
            420                 425                 430
Leu Val Thr Val Ser Ser Ala
        435
```

<210> SEQ ID NO 27
<211> LENGTH: 440
<212> TYPE: PRT
<213> ORGANISM: Artificial Sequence
<220> FEATURE:
<223> OTHER INFORMATION: VHH construct F013500720

<400> SEQUENCE: 27

Ala Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Val Arg Ser Gly Gly Ser Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Gly Arg Gly Glu Asn Tyr Ile Leu Leu Tyr Ser
            100                 105                 110

Ser Gly Arg Tyr Glu Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Leu Val
            165                 170                 175

Gln Pro Gly Asn Ser Leu Arg Leu Ser Cys Ala Ala Ser Gly Phe Thr
            180                 185                 190

Phe Ser Ser Phe Gly Met Ser Trp Val Arg Gln Ala Pro Gly Lys Gly
        195                 200                 205

Leu Glu Trp Val Ser Ser Ile Ser Gly Ser Gly Ser Asp Thr Leu Tyr
210                 215                 220

Ala Asp Ser Val Lys Gly Arg Phe Thr Ile Ser Arg Asp Asn Ala Lys
225                 230                 235                 240

Thr Thr Leu Tyr Leu Gln Met Asn Ser Leu Arg Pro Glu Asp Thr Ala
                245                 250                 255

Val Tyr Tyr Cys Thr Ile Gly Gly Ser Leu Ser Arg Ser Ser Gln Gly
            260                 265                 270

Thr Leu Val Thr Val Ser Ser Gly Gly Gly Ser Gly Gly Gly Gly
        275                 280                 285

Ser Gly Gly Gly Gly Ser Gly Gly Gly Ser Gly Gly Gly Gly Ser
    290                 295                 300

Gly Gly Gly Ser Gly Gly Gly Ser Glu Val Gln Leu Val Glu
305                 310                 315                 320

Ser Gly Gly Gly Leu Val Gln Pro Gly Gly Ser Leu Arg Leu Ser Cys
            325                 330                 335

Ala Ala Ser Gly Gly Thr Phe Ser Ser Tyr Ala Met Gly Trp Phe Arg
            340                 345                 350

Gln Ala Pro Gly Lys Glu Arg Glu Phe Val Ala Ala Ile Ser Trp Arg
        355                 360                 365

Ser Gly Ser Thr Tyr Tyr Ala Asp Ser Val Lys Gly Arg Phe Thr Ile
    370                 375                 380

Ser Arg Asp Asn Ser Lys Asn Thr Val Tyr Leu Gln Met Asn Ser Leu
385                 390                 395                 400

Arg Pro Glu Asp Thr Ala Val Tyr Tyr Cys Ala Ala Asp Pro Arg Gly
                405                 410                 415

```
Tyr Gly Val Ala Tyr Val Ser Ala Tyr Glu Tyr Trp Gly Gln Gly
            420                 425                 430

Thr Leu Val Thr Val Ser Ser Ala
            435                 440

<210> SEQ ID NO 28
<211> LENGTH: 149
<212> TYPE: PRT
<213> ORGANISM: Artificial Sequence
<220> FEATURE:
<223> OTHER INFORMATION: VHH domain F0129093A01

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Trp Ser Gly Ser Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ser Pro Ile Pro Tyr Gly Ser Leu Leu Arg Arg Asn Asn
            100                 105                 110

Tyr Asp Tyr Trp Gly Gln Gly Thr Leu Val Thr Val Ser Ser Ala Ala
            115                 120                 125

Ala Glu Gln Lys Leu Ile Ser Glu Glu Asp Leu Asn Gly Ala Ala His
            130                 135                 140

His His His His His
145

<210> SEQ ID NO 29
<211> LENGTH: 151
<212> TYPE: PRT
<213> ORGANISM: Artificial Sequence
<220> FEATURE:
<223> OTHER INFORMATION: VHH domain F0130333G06

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Arg Arg Ser Gly Arg Arg Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Arg Arg Val Arg Ser Ser Thr Arg Tyr Asn Thr Gly Thr
            100                 105                 110

Trp Trp Trp Glu Tyr Trp Gly Gln Gly Thr Leu Val Thr Val Ser Ser
            115                 120                 125
```

Ala Ala Ala Glu Gln Lys Leu Ile Ser Glu Glu Asp Leu Asn Gly Ala
        130                 135                 140

Ala His His His His His His
145                 150

<210> SEQ ID NO 30
<211> LENGTH: 148
<212> TYPE: PRT
<213> ORGANISM: Artificial Sequence
<220> FEATURE:
<223> OTHER INFORMATION: VHH domain F0129093A03

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Asn Trp Ser Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ser Arg Ser Ser Tyr Ala Gly Arg Thr Tyr Tyr Glu Leu Tyr
            100                 105                 110

Asp Tyr Trp Gly Gln Gly Thr Leu Val Thr Val Ser Ser Ala Ala Ala
        115                 120                 125

Glu Gln Lys Leu Ile Ser Glu Glu Asp Leu Asn Gly Ala Ala His His
    130                 135                 140

His His His His
145

<210> SEQ ID NO 31
<211> LENGTH: 146
<212> TYPE: PRT
<213> ORGANISM: Artificial Sequence
<220> FEATURE:
<223> OTHER INFORMATION: VHH domain F0130333E06

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Thr Val Gly Trp Phe Arg Gln Ala Pro Gly Lys Glu Arg Glu Phe Val
        35                  40                  45

Ala Ala Ile Arg Arg Arg Gly Ser Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Thr Arg Thr Val Ala Leu Leu Gln Tyr Arg Tyr Asp Tyr
            100                 105                 110

Trp Gly Gln Gly Thr Leu Val Thr Val Ser Ser Ala Ala Ala Glu Gln

```
                   115                 120                 125
Lys Leu Ile Ser Glu Glu Asp Leu Asn Gly Ala Ala His His His
        130                 135                 140

His His
145

<210> SEQ ID NO 32
<211> LENGTH: 152
<212> TYPE: PRT
<213> ORGANISM: Artificial Sequence
<220> FEATURE:
<223> OTHER INFORMATION: VHH domain F0130332D03

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Asn Arg Ser Gly Gly Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Gly Arg Gly Glu Asn Tyr Ser Leu Leu Tyr Ser
            100                 105                 110

Ser Asn Arg Tyr Glu Tyr Trp Gly Gln Gly Thr Leu Val Thr Val Ser
        115                 120                 125

Ser Ala Ala Ala Glu Gln Lys Leu Ile Ser Glu Glu Asp Leu Asn Gly
    130                 135                 140

Ala Ala His His His His His His
145                 150

<210> SEQ ID NO 33
<211> LENGTH: 148
<212> TYPE: PRT
<213> ORGANISM: Artificial Sequence
<220> FEATURE:
<223> OTHER INFORMATION: VHH domain F0130367B10

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Arg Ser Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Gly Thr Ala Val Tyr Tyr Cys
                85                  90                  95

Ala Ala Asp Pro Arg Gly Tyr Gly Val Ala Tyr Val Ser Ala Tyr Tyr
            100                 105                 110
```

-continued

```
Glu Tyr Trp Gly Gln Gly Thr Leu Val Thr Val Ser Gly Ala Ala
            115                 120                 125

Glu Gln Lys Leu Ile Ser Glu Glu Asp Leu Asn Gly Ala Ala His His
    130                 135                 140

His His His His
145

<210> SEQ ID NO 34
<211> LENGTH: 149
<212> TYPE: PRT
<213> ORGANISM: Artificial Sequence
<220> FEATURE:
<223> OTHER INFORMATION: VHH domain F0130378B05

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Arg Ser Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Val Tyr Ser Thr Leu Pro Pro Thr Ser Arg
            100                 105                 110

Tyr Asn Tyr Trp Gly Gln Gly Thr Leu Val Thr Val Ser Ser Ala Ala
        115                 120                 125

Ala Glu Gln Lys Leu Ile Ser Glu Glu Asp Leu Asn Gly Ala Ala His
    130                 135                 140

His His His His His
145

<210> SEQ ID NO 35
<211> LENGTH: 147
<212> TYPE: PRT
<213> ORGANISM: Artificial Sequence
<220> FEATURE:
<223> OTHER INFORMATION: VHH domain F0130378A04

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Thr Arg Thr Gly Arg Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Gly Tyr Tyr Tyr Asp Ser Ser Phe Tyr Asp
            100                 105                 110
```

Tyr Trp Gly Gln Gly Thr Leu Val Thr Val Ser Ser Ala Ala Ala Glu
        115                 120                 125

Gln Lys Leu Ile Ser Glu Glu Asp Leu Asn Gly Ala Ala His His His
    130                 135                 140

His His His
145

<210> SEQ ID NO 36
<211> LENGTH: 150
<212> TYPE: PRT
<213> ORGANISM: Artificial Sequence
<220> FEATURE:
<223> OTHER INFORMATION: VHH domain F0130372C08

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Asp Tyr
            20                  25                  30

Gly Met Gly Trp Phe Arg Gln Ala Pro Gly Lys Glu Arg Glu Phe Val
        35                  40                  45

Ala Ala Ile Ser Trp Ser Gly Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Lys Arg Arg Gly Arg Gly Ser Val Ser Pro Asn Ser Ser Ser
            100                 105                 110

Arg Tyr Asn Tyr Trp Gly Gln Gly Thr Leu Val Thr Val Ser Ser Ala
        115                 120                 125

Ala Ala Glu Gln Lys Leu Ile Ser Glu Glu Asp Leu Asn Gly Ala Ala
    130                 135                 140

His His His His His His
145                 150

<210> SEQ ID NO 37
<211> LENGTH: 462
<212> TYPE: PRT
<213> ORGANISM: Artificial Sequence
<220> FEATURE:
<223> OTHER INFORMATION: VHH construct F013500016

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Asn Arg Ser Gly Gly Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Gly Arg Gly Glu Asn Tyr Ser Leu Leu Tyr Ser

```
                    100                 105                 110
Ser Asn Arg Tyr Glu Tyr Trp Gly Gln Gly Thr Leu Val Thr Val Ser
                115                 120                 125

Ser Gly Gly Gly Gly Ser Gly Gly Gly Ser Gly Gly Gly Gly Ser
    130                 135                 140

Gly Gly Gly Ser Gly Gly Gly Ser Gly Gly Gly Ser Gly
145             150              155                 160

Gly Gly Gly Ser Glu Val Gln Leu Val Glu Ser Gly Gly Gly Leu Val
                165                 170                 175

Gln Pro Gly Asn Ser Leu Arg Leu Ser Cys Ala Ala Ser Gly Phe Thr
            180                 185                 190

Phe Ser Ser Phe Gly Met Ser Trp Val Arg Gln Ala Pro Gly Lys Gly
        195                 200                 205

Leu Glu Trp Val Ser Ser Ile Ser Gly Ser Gly Ser Asp Thr Leu Tyr
    210                 215                 220

Ala Asp Ser Val Lys Gly Arg Phe Thr Ile Ser Arg Asp Asn Ala Lys
225                 230                 235                 240

Thr Thr Leu Tyr Leu Gln Met Asn Ser Leu Arg Pro Glu Asp Thr Ala
                245                 250                 255

Val Tyr Tyr Cys Thr Ile Gly Gly Ser Leu Ser Arg Ser Gln Gly
                260                 265                 270

Thr Leu Val Thr Val Ser Ser Gly Gly Gly Ser Gly Gly Gly Gly
                275                 280                 285

Ser Gly Gly Gly Gly Ser Gly Gly Gly Gly Ser Gly Gly Gly Ser
    290                 295                 300

Gly Gly Gly Ser Gly Gly Gly Ser Glu Val Gln Leu Val Glu
305             310                 315                 320

Ser Gly Gly Gly Leu Val Gln Pro Gly Gly Ser Leu Arg Leu Ser Cys
                325                 330                 335

Ala Ala Ser Gly Gly Thr Phe Ser Ser Tyr Ala Met Gly Trp Phe Arg
            340                 345                 350

Gln Ala Pro Gly Lys Glu Arg Glu Phe Val Ala Ala Ile Ser Trp Arg
        355                 360                 365

Ser Gly Ser Thr Tyr Tyr Ala Asp Ser Val Lys Gly Arg Phe Thr Ile
    370                 375                 380

Ser Arg Asp Asn Ser Lys Asn Thr Val Tyr Leu Gln Met Asn Ser Leu
385                 390                 395                 400

Arg Pro Glu Gly Thr Ala Val Tyr Tyr Cys Ala Ala Asp Pro Arg Gly
                405                 410                 415

Tyr Gly Val Ala Tyr Val Ser Ala Tyr Tyr Glu Tyr Trp Gly Gln Gly
                420                 425                 430

Thr Leu Val Thr Val Ser Ser Gly Ala Ala Glu Gln Lys Leu Ile Ser
                435                 440                 445

Glu Glu Asp Leu Asn Gly Ala Ala His His His His His
    450                 455                 460

<210> SEQ ID NO 38
<211> LENGTH: 463
<212> TYPE: PRT
<213> ORGANISM: Artificial Sequence
<220> FEATURE:
<223> OTHER INFORMATION: VHH construct F013500018

<400> SEQUENCE: 38

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Leu Thr Phe Ser Arg Tyr
                20                  25                  30

Thr Met Gly Trp Phe Arg Gln Ala Pro Gly Lys Glu Arg Glu Phe Val
                35                  40                  45

Ala Ala Ile Asn Arg Ser Gly Ser Thr Tyr Tyr Ser Asp Ser Val
                50                  55                  60

Lys Gly Arg Phe Thr Ile Ser Arg Asp Asn Ser Lys Asn Thr Val Tyr
65                      70                  75                  80

Leu Gln Met Asn Ser Leu Arg Pro Glu Asp Thr Ala Val Tyr Tyr Cys
                85                  90                  95

Ala Ala Asp Arg Arg Gly Arg Gly Glu Asn Tyr Ser Leu Leu Tyr Ser
                100                 105                 110

Ser Asn Arg Tyr Glu Tyr Trp Gly Gln Gly Thr Leu Val Thr Val Ser
                115                 120                 125

Ser Gly Gly Gly Gly Ser Gly Gly Gly Gly Ser Gly Gly Gly Gly Ser
                130                 135                 140

Gly Gly Gly Gly Ser Gly Gly Gly Ser Gly Gly Gly Ser Gly
145                     150                 155                 160

Gly Gly Gly Ser Glu Val Gln Leu Val Glu Ser Gly Gly Gly Leu Val
                165                 170                 175

Gln Pro Gly Asn Ser Leu Arg Leu Ser Cys Ala Ala Ser Gly Phe Thr
                180                 185                 190

Phe Ser Ser Phe Gly Met Ser Trp Val Arg Gln Ala Pro Gly Lys Gly
                195                 200                 205

Leu Glu Trp Val Ser Ser Ile Ser Gly Ser Gly Ser Asp Thr Leu Tyr
                210                 215                 220

Ala Asp Ser Val Lys Gly Arg Phe Thr Ile Ser Arg Asp Asn Ala Lys
225                     230                 235                 240

Thr Thr Leu Tyr Leu Gln Met Asn Ser Leu Arg Pro Glu Asp Thr Ala
                245                 250                 255

Val Tyr Tyr Cys Thr Ile Gly Gly Ser Leu Ser Arg Ser Ser Gln Gly
                260                 265                 270

Thr Leu Val Thr Val Ser Ser Gly Gly Gly Ser Gly Gly Gly Gly
                275                 280                 285

Ser Gly Gly Gly Gly Ser Gly Gly Gly Gly Ser Gly Gly Gly Gly Ser
                290                 295                 300

Gly Gly Gly Gly Ser Gly Gly Gly Ser Glu Val Gln Leu Val Glu
305                     310                 315                 320

Ser Gly Gly Gly Leu Val Gln Pro Gly Gly Ser Leu Arg Leu Ser Cys
                325                 330                 335

Val Ala Ser Gly Arg Thr Phe Ser Ser Tyr Ala Met Gly Trp Phe Arg
                340                 345                 350

Gln Ala Pro Gly Lys Glu Arg Glu Phe Val Ala Ala Ile Ser Arg Ser
                355                 360                 365

Gly Gly Arg Thr Tyr Tyr Ala Asp Ser Val Lys Gly Arg Phe Thr Ile
                370                 375                 380

Ser Arg Asp Asn Ser Lys Asn Thr Val Tyr Leu Gln Met Asn Ser Leu
385                     390                 395                 400

Arg Pro Glu Asp Thr Ala Val Tyr Tyr Cys Ala Ala Asp Arg Arg Val
                405                 410                 415

Tyr Ser Thr Leu Pro Pro Thr Ser Arg Tyr Asn Tyr Trp Gly Gln
                420                 425                 430
```

```
Gly Thr Leu Val Thr Val Ser Ser Gly Ala Ala Glu Gln Lys Leu Ile
        435                 440                 445

Ser Glu Glu Asp Leu Asn Gly Ala Ala His His His His His His
450                 455                 460
```

<210> SEQ ID NO 39
<211> LENGTH: 461
<212> TYPE: PRT
<213> ORGANISM: Artificial Sequence
<220> FEATURE:
<223> OTHER INFORMATION: VHH construct F013500021

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Arg Arg Ser Gly Arg Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Arg Arg Val Arg Ser Ser Thr Arg Tyr Asn Thr Gly Thr
            100                 105                 110

Trp Trp Trp Glu Tyr Trp Gly Gln Gly Thr Leu Val Thr Val Ser Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Gly Gly
145                 150                 155                 160

Gly Gly Ser Glu Val Gln Leu Val Glu Ser Gly Gly Gly Leu Val Gln
                165                 170                 175

Pro Gly Asn Ser Leu Arg Leu Ser Cys Ala Ala Ser Gly Phe Thr Phe
            180                 185                 190

Ser Ser Phe Gly Met Ser Trp Val Arg Gln Ala Pro Gly Lys Gly Leu
        195                 200                 205

Glu Trp Val Ser Ser Ile Ser Gly Ser Gly Ser Asp Thr Leu Tyr Ala
    210                 215                 220

Asp Ser Val Lys Gly Arg Phe Thr Ile Ser Arg Asp Asn Ala Lys Thr
225                 230                 235                 240

Thr Leu Tyr Leu Gln Met Asn Ser Leu Arg Pro Glu Asp Thr Ala Val
                245                 250                 255

Tyr Tyr Cys Thr Ile Gly Gly Ser Leu Ser Arg Ser Ser Gln Gly Thr
            260                 265                 270

Leu Val Thr Val Ser Ser Gly Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Ser Gly Gly Gly Gly Ser Glu Val Gln Leu Val Glu Ser
305                 310                 315                 320

Gly Gly Gly Leu Val Gln Pro Gly Gly Ser Leu Arg Leu Ser Cys Ala
                325                 330                 335
```

```
Ala Ser Gly Gly Thr Phe Ser Ser Tyr Ala Met Gly Trp Phe Arg Gln
            340                 345                 350

Ala Pro Gly Lys Glu Arg Glu Phe Val Ala Ala Ile Ser Trp Arg Ser
            355                 360                 365

Gly Ser Thr Tyr Tyr Ala Asp Ser Val Lys Gly Arg Phe Thr Ile Ser
            370                 375                 380

Arg Asp Asn Ser Lys Asn Thr Val Tyr Leu Gln Met Asn Ser Leu Arg
385                 390                 395                 400

Pro Glu Gly Thr Ala Val Tyr Tyr Cys Ala Ala Asp Pro Arg Gly Tyr
                405                 410                 415

Gly Val Ala Tyr Val Ser Ala Tyr Glu Tyr Trp Gly Gln Gly Thr
                420                 425                 430

Leu Val Thr Val Ser Ser Gly Ala Ala Glu Gln Lys Leu Ile Ser Glu
            435                 440                 445

Glu Asp Leu Asn Gly Ala Ala His His His His His His
            450                 455                 460

<210> SEQ ID NO 40
<211> LENGTH: 456
<212> TYPE: PRT
<213> ORGANISM: Artificial Sequence
<220> FEATURE:
<223> OTHER INFORMATION: VHH construct F013500026

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Thr Val Gly Trp Phe Arg Gln Ala Pro Gly Lys Glu Arg Glu Phe Val
        35                  40                  45

Ala Ala Ile Arg Arg Arg Gly Ser Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Thr Arg Thr Val Ala Leu Leu Gln Tyr Arg Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Gly Ser Glu Val
145                 150                 155                 160

Gln Leu Val Glu Ser Gly Gly Gly Leu Val Gln Pro Gly Asn Ser Leu
                165                 170                 175

Arg Leu Ser Cys Ala Ala Ser Gly Phe Thr Phe Ser Ser Phe Gly Met
            180                 185                 190

Ser Trp Val Arg Gln Ala Pro Gly Lys Gly Leu Glu Trp Val Ser Ser
        195                 200                 205

Ile Ser Gly Ser Gly Ser Asp Thr Leu Tyr Ala Asp Ser Val Lys Gly
    210                 215                 220

Arg Phe Thr Ile Ser Arg Asp Asn Ala Lys Thr Thr Leu Tyr Leu Gln
225                 230                 235                 240
```

```
Met Asn Ser Leu Arg Pro Glu Asp Thr Ala Val Tyr Tyr Cys Thr Ile
            245                 250                 255

Gly Gly Ser Leu Ser Arg Ser Ser Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Gly Ser Gly Gly Gly Gly Ser Gly
            290                 295                 300

Gly Gly Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Gly Thr
            325                 330                 335

Phe Ser Ser Tyr Ala Met Gly Trp Phe Arg Gln Ala Pro Gly Lys Glu
            340                 345                 350

Arg Glu Phe Val Ala Ala Ile Ser Trp Arg Ser Gly Ser Thr Tyr Tyr
            355                 360                 365

Ala Asp Ser Val Lys Gly Arg Phe Thr Ile Ser Arg Asp Asn Ser Lys
            370                 375                 380

Asn Thr Val Tyr Leu Gln Met Asn Ser Leu Arg Pro Glu Gly Thr Ala
385                 390                 395                 400

Val Tyr Tyr Cys Ala Ala Asp Pro Arg Gly Tyr Gly Val Ala Tyr Val
            405                 410                 415

Ser Ala Tyr Tyr Glu Tyr Trp Gly Gln Gly Thr Leu Val Thr Val Ser
            420                 425                 430

Ser Gly Ala Ala Glu Gln Lys Leu Ile Ser Glu Glu Asp Leu Asn Gly
            435                 440                 445

Ala Ala His His His His His His
            450                 455

<210> SEQ ID NO 41
<211> LENGTH: 461
<212> TYPE: PRT
<213> ORGANISM: Artificial Sequence
<220> FEATURE:
<223> OTHER INFORMATION: VHH construct F013500030

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Arg Ser Gly Arg Thr Tyr Tyr Ala Asp Ser Val
            50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Asp Arg Arg Val Tyr Ser Thr Leu Pro Pro Thr Ser Arg
            100                 105                 110

Tyr Asn Tyr Trp Gly Gln Gly Thr Leu Val Thr Val Ser Ser Gly Gly
            115                 120                 125

Gly Gly Ser Gly Gly Gly Gly Ser Gly Gly Gly Gly Ser Gly Gly Gly
            130                 135                 140
```

Gly Ser Gly Gly Gly Ser Gly Gly Gly Ser Gly Gly Gly
145                 150                 155                 160

Ser Glu Val Gln Leu Val Glu Ser Gly Gly Leu Val Gln Pro Gly
            165                 170                 175

Asn Ser Leu Arg Leu Ser Cys Ala Ala Ser Gly Phe Thr Phe Ser Ser
        180                 185                 190

Phe Gly Met Ser Trp Val Arg Gln Ala Pro Gly Lys Gly Leu Glu Trp
    195                 200                 205

Val Ser Ser Ile Ser Gly Ser Gly Ser Asp Thr Leu Tyr Ala Asp Ser
210                 215                 220

Val Lys Gly Arg Phe Thr Ile Ser Arg Asp Asn Ala Lys Thr Thr Leu
225                 230                 235                 240

Tyr Leu Gln Met Asn Ser Leu Arg Pro Glu Asp Thr Ala Val Tyr Tyr
            245                 250                 255

Cys Thr Ile Gly Gly Ser Leu Arg Ser Ser Gln Gly Thr Leu Val
                260                 265                 270

Thr Val Ser Ser Gly Gly Gly Gly Ser Gly Gly Gly Ser Gly Gly
        275                 280                 285

Gly Gly Ser Gly Gly Gly Ser Gly Gly Gly Ser Gly Gly Gly
290                 295                 300

Gly Ser Gly Gly Gly Ser Glu Val Gln Leu Val Glu Ser Gly Gly
305                 310                 315                 320

Gly Leu Val Gln Pro Gly Gly Ser Leu Arg Leu Ser Cys Ala Ala Ser
                325                 330                 335

Gly Arg Thr Phe Ser Asp Tyr Gly Met Gly Trp Phe Arg Gln Ala Pro
            340                 345                 350

Gly Lys Glu Arg Glu Phe Val Ala Ala Ile Ser Trp Ser Gly Arg
            355                 360                 365

Thr Tyr Tyr Ala Asp Ser Val Lys Gly Arg Phe Thr Ile Ser Arg Asp
    370                 375                 380

Asn Ser Lys Asn Thr Val Tyr Leu Gln Met Asn Ser Leu Arg Pro Glu
385                 390                 395                 400

Asp Thr Ala Val Tyr Tyr Cys Ala Ala Lys Arg Gly Arg Gly Ser
                405                 410                 415

Val Ser Pro Asn Ser Ser Arg Tyr Asn Tyr Trp Gly Gln Gly Thr
            420                 425                 430

Leu Val Thr Val Ser Ser Gly Ala Ala Glu Gln Lys Leu Ile Ser Glu
        435                 440                 445

Glu Asp Leu Asn Gly Ala Ala His His His His His
            450                 455                 460

<210> SEQ ID NO 42
<211> LENGTH: 460
<212> TYPE: PRT
<213> ORGANISM: Artificial Sequence
<220> FEATURE:
<223> OTHER INFORMATION: VHH construct F013500032

<400> SEQUENCE: 42

Glu Val Gln Leu Val Glu Ser Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

```
Ala Ala Ile Thr Arg Thr Gly Arg Arg Thr Tyr Tyr Ala Asp Ser Val
         50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Asp Arg Arg Gly Tyr Tyr Tyr Asp Ser Ser Phe Tyr Asp
             100                 105                 110

Tyr Trp Gly Gln Gly Thr Leu Val Thr Val Ser Ser Gly Gly Gly Gly
             115                 120                 125

Ser Gly Gly Gly Gly Ser Gly Gly Gly Gly Ser Gly Gly Gly Gly Ser
             130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Asn Ser
                 165                 170                 175

Leu Arg Leu Ser Cys Ala Ala Ser Gly Phe Thr Phe Ser Ser Phe Gly
             180                 185                 190

Met Ser Trp Val Arg Gln Ala Pro Gly Lys Gly Leu Glu Trp Val Ser
             195                 200                 205

Ser Ile Ser Gly Ser Gly Ser Asp Thr Leu Tyr Ala Asp Ser Val Lys
    210                 215                 220

Gly Arg Phe Thr Ile Ser Arg Asp Asn Ala Lys Thr Thr Leu Tyr Leu
225                 230                 235                 240

Gln Met Asn Ser Leu Arg Pro Glu Asp Thr Ala Val Tyr Tyr Cys Thr
                 245                 250                 255

Ile Gly Gly Ser Leu Ser Arg Ser Ser Gln Gly Thr Leu Val Thr Val
             260                 265                 270

Ser Ser Gly Gly Gly Gly Ser Gly Gly Gly Gly Ser Gly Gly Gly Gly
         275                 280                 285

Ser Gly Gly Gly Gly Ser Gly Gly Gly Gly Ser Gly Gly Gly Gly Ser
         290                 295                 300

Gly Gly Gly Gly Ser Glu Val Gln Leu Val Glu Ser Gly Gly Gly Leu
305                 310                 315                 320

Val Gln Pro Gly Gly Ser Leu Arg Leu Ser Cys Ala Ala Ser Gly Gly
             325                 330                 335

Thr Phe Ser Ser Tyr Ala Met Gly Trp Phe Arg Gln Ala Pro Gly Lys
             340                 345                 350

Glu Arg Glu Phe Val Ala Ala Ile Arg Arg Ser Gly Arg Arg Thr Tyr
             355                 360                 365

Tyr Ala Asp Ser Val Lys Gly Arg Phe Thr Ile Ser Arg Asp Asn Ser
    370                 375                 380

Lys Asn Thr Val Tyr Leu Gln Met Asn Ser Leu Arg Pro Glu Asp Thr
385                 390                 395                 400

Ala Val Tyr Tyr Cys Ala Ala Arg Arg Val Arg Ser Ser Thr Arg
                 405                 410                 415

Tyr Asn Thr Gly Thr Trp Trp Trp Glu Tyr Trp Gly Gln Gly Thr Leu
             420                 425                 430

Val Thr Val Ser Ser Gly Ala Ala Glu Gln Lys Leu Ile Ser Glu Glu
             435                 440                 445

Asp Leu Asn Gly Ala Ala His His His His His His
             450                 455                 460
```

```
<210> SEQ ID NO 43
<211> LENGTH: 462
<212> TYPE: PRT
<213> ORGANISM: Artificial Sequence
<220> FEATURE:
<223> OTHER INFORMATION: VHH construct F013500033

<400> SEQUENCE: 43
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |
| Ser | Leu | Arg | Leu | Ser | Cys | Val | Ala | Ser | Gly | Arg | Thr | Phe | Ser | Ser |
| | | | 20 | | | | | 25 | | | | | 30 | |
| Tyr | | | | | | | | | | | | | | |
| Ala | Met | Gly | Trp | Phe | Arg | Gln | Ala | Pro | Gly | Lys | Glu | Arg | Glu | Phe |
| | | 35 | | | | | 40 | | | | | 45 | | |
| Val | | | | | | | | | | | | | | |
| Ala | Ala | Ile | Ser | Arg | Ser | Gly | Gly | Arg | Thr | Tyr | Tyr | Ala | Asp | Ser |
| | 50 | | | | | 55 | | | | | 60 | | | |
| Val | | | | | | | | | | | | | | |
| Lys | Gly | Arg | Phe | Thr | Ile | Ser | Arg | Asp | Asn | Ser | Lys | Asn | Thr | Val |
| 65 | | | | | 70 | | | | | 75 | | | | |
| Tyr | | | | | | | | | | | | | | 80 |
| Leu | Gln | Met | Asn | Ser | Leu | Arg | Pro | Glu | Asp | Thr | Ala | Val | Tyr | Tyr |
| | | | | 85 | | | | | 90 | | | | | 95 |
| Cys | | | | | | | | | | | | | | |
| Ala | Ala | Asp | Arg | Arg | Val | Tyr | Ser | Thr | Leu | Pro | Pro | Thr | Thr | Ser |
| | | | 100 | | | | | 105 | | | | | 110 | |
| Arg | | | | | | | | | | | | | | |
| Tyr | Asn | Tyr | Trp | Gly | Gln | Gly | Thr | Leu | Val | Thr | Val | Ser | Ser | Gly |
| | | 115 | | | | | 120 | | | | | 125 | | |
| Gly | | | | | | | | | | | | | | |
| Gly | Gly | Ser | Gly | Gly | Gly | Gly | Ser | Gly | Gly | Gly | Ser | Gly | Gly | Gly |
| 130 | | | | | 135 | | | | | 140 | | | | |
| Gly | Ser | Gly | Gly | Gly | Gly | Ser | Gly | Gly | Gly | Ser | Gly | Gly | Gly | Gly |
| 145 | | | | | 150 | | | | | 155 | | | | 160 |
| Ser | Glu | Val | Gln | Leu | Val | Glu | Ser | Gly | Gly | Leu | Val | Gln | Pro | Gly |
| | | | | 165 | | | | | 170 | | | | | 175 |
| Asn | Ser | Leu | Arg | Leu | Ser | Cys | Ala | Ala | Ser | Gly | Phe | Thr | Phe | Ser |
| | | | 180 | | | | | 185 | | | | | 190 | |
| Ser | | | | | | | | | | | | | | |
| Phe | Gly | Met | Ser | Trp | Val | Arg | Gln | Ala | Pro | Gly | Lys | Gly | Leu | Glu |
| | | 195 | | | | | 200 | | | | | 205 | | |
| Trp | | | | | | | | | | | | | | |
| Val | Ser | Ser | Ile | Ser | Gly | Ser | Gly | Ser | Asp | Thr | Leu | Tyr | Ala | Asp |
| | 210 | | | | | 215 | | | | | 220 | | | |
| Ser | | | | | | | | | | | | | | |
| Val | Lys | Gly | Arg | Phe | Thr | Ile | Ser | Arg | Asp | Asn | Ala | Lys | Thr | Thr |
| 225 | | | | | 230 | | | | | 235 | | | | 240 |
| Leu | | | | | | | | | | | | | | |
| Tyr | Leu | Gln | Met | Asn | Ser | Leu | Arg | Pro | Glu | Asp | Thr | Ala | Val | Tyr |
| | | | | 245 | | | | | 250 | | | | | 255 |
| Tyr | | | | | | | | | | | | | | |
| Cys | Thr | Ile | Gly | Gly | Ser | Leu | Ser | Arg | Ser | Ser | Gln | Gly | Thr | Leu |
| | | | 260 | | | | | 265 | | | | | 270 | |
| Val | | | | | | | | | | | | | | |
| Thr | Val | Ser | Ser | Gly | Gly | Gly | Gly | Ser | Gly | Gly | Gly | Gly | Ser | Gly |
| | | 275 | | | | | 280 | | | | | 285 | | |
| Gly | | | | | | | | | | | | | | |
| Gly | Gly | Ser | Gly | Gly | Gly | Gly | Ser | Gly | Gly | Gly | Gly | Ser | Gly | Gly |
| | 290 | | | | | 295 | | | | | 300 | | | |
| Gly | | | | | | | | | | | | | | |
| Gly | Ser | Gly | Gly | Gly | Gly | Ser | Glu | Val | Gln | Leu | Val | Glu | Ser | Gly |
| 305 | | | | | 310 | | | | | 315 | | | | |
| Gly | | | | | | | | | | | | | | 320 |
| Gly | Leu | Val | Gln | Pro | Gly | Gly | Ser | Leu | Arg | Leu | Ser | Cys | Ala | Ala |
| | | | | 325 | | | | | 330 | | | | | 335 |
| Ser | | | | | | | | | | | | | | |
| Gly | Gly | Thr | Phe | Ser | Ser | Tyr | Ala | Met | Gly | Trp | Phe | Arg | Gln | Ala |
| | | | 340 | | | | | 345 | | | | | 350 | |
| Pro | | | | | | | | | | | | | | |
| Gly | Lys | Glu | Arg | Glu | Phe | Val | Ala | Ala | Ile | Arg | Arg | Ser | Gly | Arg |
| | | | | 355 | | | | | 360 | | | | | 365 |
| Arg | | | | | | | | | | | | | | |

```
Thr Tyr Tyr Ala Asp Ser Val Lys Gly Arg Phe Thr Ile Ser Arg Asp
    370             375                 380

Asn Ser Lys Asn Thr Val Tyr Leu Gln Met Asn Ser Leu Arg Pro Glu
385             390                 395                 400

Asp Thr Ala Val Tyr Tyr Cys Ala Ala Ala Arg Arg Val Arg Ser Ser
                405                 410                 415

Thr Arg Tyr Asn Thr Gly Thr Trp Trp Trp Glu Tyr Trp Gly Gln Gly
            420                 425                 430

Thr Leu Val Thr Val Ser Ser Gly Ala Ala Glu Gln Lys Leu Ile Ser
                435                 440                 445

Glu Glu Asp Leu Asn Gly Ala Ala His His His His His His
    450                 455                 460

<210> SEQ ID NO 44
<211> LENGTH: 456
<212> TYPE: PRT
<213> ORGANISM: Artificial Sequence
<220> FEATURE:
<223> OTHER INFORMATION: VHH construct F013500039

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Asn Trp Ser Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Ser Arg Ser Ser Tyr Ala Gly Arg Thr Tyr Tyr Glu Leu Tyr
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Gly Leu Val Gln Pro Gly Asn
            165                 170                 175

Ser Leu Arg Leu Ser Cys Ala Ala Ser Gly Phe Thr Phe Ser Ser Phe
        180                 185                 190

Gly Met Ser Trp Val Arg Gln Ala Pro Gly Lys Gly Leu Glu Trp Val
    195                 200                 205

Ser Ser Ile Ser Gly Ser Gly Ser Asp Thr Leu Tyr Ala Asp Ser Val
    210                 215                 220

Lys Gly Arg Phe Thr Ile Ser Arg Asp Asn Ala Lys Thr Thr Leu Tyr
225                 230                 235                 240

Leu Gln Met Asn Ser Leu Arg Pro Glu Asp Thr Ala Val Tyr Tyr Cys
            245                 250                 255

Thr Ile Gly Gly Ser Leu Ser Arg Ser Ser Gln Gly Thr Leu Val Thr
            260                 265                 270
```

```
Val Ser Ser Gly Gly Gly Ser Gly Gly Gly Ser Gly Gly
        275                 280                 285
Gly Ser Gly Gly Gly Ser Gly Gly Gly Ser Gly Gly Gly
        290                 295                 300
Ser Gly Gly Gly Ser Glu Val Gln Leu Val Glu Ser Gly Gly
305                 310                 315                 320
Leu Val Gln Pro Gly Gly Ser Leu Arg Leu Ser Cys Ala Ala Ser Gly
            325                 330                 335
Arg Thr Phe Ser Thr Tyr Thr Val Gly Trp Phe Arg Gln Ala Pro Gly
            340                 345                 350
Lys Glu Arg Glu Phe Val Ala Ala Ile Arg Arg Arg Gly Ser Ser Thr
            355                 360                 365
Tyr Tyr Ser Asp Ser Val Lys Gly Arg Phe Thr Ile Ser Arg Asp Asn
370                 375                 380
Ser Lys Asn Thr Val Tyr Leu Gln Met Asn Ser Leu Arg Pro Glu Asp
385                 390                 395                 400
Thr Ala Val Tyr Tyr Cys Ala Ala Asp Thr Arg Thr Val Ala Leu Leu
                405                 410                 415
Gln Tyr Arg Tyr Asp Tyr Trp Gly Gln Gly Thr Leu Val Thr Val Ser
            420                 425                 430
Ser Gly Ala Ala Glu Gln Lys Leu Ile Ser Glu Glu Asp Leu Asn Gly
        435                 440                 445
Ala Ala His His His His His His
        450                 455

<210> SEQ ID NO 45
<211> LENGTH: 463
<212> TYPE: PRT
<213> ORGANISM: Artificial Sequence
<220> FEATURE:
<223> OTHER INFORMATION: VHH construct F013500046

<400> SEQUENCE: 45

Glu Val Gln Leu Val Glu Ser Gly Gly Gly Leu Val Gln Pro Gly Gly
1               5                   10                  15
Ser Leu Arg Leu Ser Cys Ala Ala Ser Gly Leu Thr Phe Ser Arg Tyr
            20                  25                  30
Thr Met Gly Trp Phe Arg Gln Ala Pro Gly Lys Glu Arg Glu Phe Val
        35                  40                  45
Ala Ala Ile Asn Arg Ser Gly Gly Ser Thr Tyr Tyr Ser Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Val Tyr Tyr Cys
                85                  90                  95
Ala Ala Asp Arg Arg Gly Arg Gly Glu Asn Tyr Ser Leu Leu Tyr Ser
            100                 105                 110
Ser Asn Arg Tyr Glu Tyr Trp Gly Gln Gly Thr Leu Val Thr Val Ser
        115                 120                 125
Ser Gly Gly Gly Gly Ser Gly Gly Gly Gly Ser Gly Gly Gly Gly Ser
    130                 135                 140
Gly Gly Gly Gly Ser Gly Gly Gly Ser Gly Gly Gly Ser Gly
145                 150                 155                 160
Gly Gly Gly Ser Glu Val Gln Leu Val Glu Ser Gly Gly Gly Leu Val
                165                 170                 175
```

-continued

Gln Pro Gly Asn Ser Leu Arg Leu Ser Cys Ala Ala Ser Gly Phe Thr
                180                 185                 190

Phe Ser Ser Phe Gly Met Ser Trp Val Arg Gln Ala Pro Gly Lys Gly
            195                 200                 205

Leu Glu Trp Val Ser Ser Ile Ser Gly Ser Gly Ser Asp Thr Leu Tyr
        210                 215                 220

Ala Asp Ser Val Lys Gly Arg Phe Thr Ile Ser Arg Asp Asn Ala Lys
225                 230                 235                 240

Thr Thr Leu Tyr Leu Gln Met Asn Ser Leu Arg Pro Glu Asp Thr Ala
                245                 250                 255

Val Tyr Tyr Cys Thr Ile Gly Gly Ser Leu Ser Arg Ser Ser Gln Gly
            260                 265                 270

Thr Leu Val Thr Val Ser Ser Gly Gly Gly Ser Gly Gly Gly Gly
        275                 280                 285

Ser Gly Gly Gly Gly Ser Gly Gly Gly Ser Gly Gly Gly Ser
    290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Gly Ser Leu Arg Leu Ser Cys
                325                 330                 335

Ala Ala Ser Gly Arg Thr Phe Ser Ser Tyr Ala Met Gly Trp Phe Arg
            340                 345                 350

Gln Ala Pro Gly Lys Glu Arg Glu Phe Val Ala Ala Ile Ser Trp Ser
        355                 360                 365

Gly Gly Ser Thr Tyr Tyr Ala Asp Ser Val Lys Gly Arg Phe Thr Ile
    370                 375                 380

Ser Arg Asp Asn Ser Lys Asn Thr Val Tyr Leu Gln Met Asn Ser Leu
385                 390                 395                 400

Arg Pro Glu Asp Thr Ala Val Tyr Tyr Cys Ala Ala Ser Pro Ile Pro
                405                 410                 415

Tyr Gly Ser Leu Leu Arg Arg Arg Asn Asn Tyr Asp Tyr Trp Gly Gln
            420                 425                 430

Gly Thr Leu Val Thr Val Ser Ser Gly Ala Ala Glu Gln Lys Leu Ile
        435                 440                 445

Ser Glu Glu Asp Leu Asn Gly Ala Ala His His His His His His
450                 455                 460

<210> SEQ ID NO 46
<211> LENGTH: 457
<212> TYPE: PRT
<213> ORGANISM: Artificial Sequence
<220> FEATURE:
<223> OTHER INFORMATION: VHH construct F013500047

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Thr Val Gly Trp Phe Arg Gln Ala Pro Gly Lys Glu Arg Glu Phe Val
        35                  40                  45

Ala Ala Ile Arg Arg Arg Gly Ser Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

```
Leu Gln Met Asn Ser Leu Arg Pro Glu Asp Thr Ala Val Tyr Tyr Cys
                85                  90                  95

Ala Ala Asp Thr Arg Thr Val Ala Leu Leu Gln Tyr Arg Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Glu Val
145                 150                 155                 160

Gln Leu Val Glu Ser Gly Gly Leu Val Gln Pro Gly Asn Ser Leu
                165                 170                 175

Arg Leu Ser Cys Ala Ala Ser Gly Phe Thr Phe Ser Ser Phe Gly Met
                180                 185                 190

Ser Trp Val Arg Gln Ala Pro Gly Lys Gly Leu Glu Trp Val Ser Ser
            195                 200                 205

Ile Ser Gly Ser Gly Ser Asp Thr Leu Tyr Ala Asp Ser Val Lys Gly
    210                 215                 220

Arg Phe Thr Ile Ser Arg Asp Asn Ala Lys Thr Thr Leu Tyr Leu Gln
225                 230                 235                 240

Met Asn Ser Leu Arg Pro Glu Asp Thr Ala Val Tyr Tyr Cys Thr Ile
                245                 250                 255

Gly Gly Ser Leu Ser Arg Ser Ser Gln Gly Thr Leu Val Thr Val Ser
                260                 265                 270

Ser Gly Gly Gly Gly Ser Gly Gly Gly Gly Ser Gly Gly Gly Gly Ser
            275                 280                 285

Gly Gly Gly Ser Gly Gly Gly Gly Ser Gly Gly Gly Ser Gly
    290                 295                 300

Gly Gly Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Arg Thr
                325                 330                 335

Phe Ser Ser Tyr Ala Met Gly Trp Phe Arg Gln Ala Pro Gly Lys Glu
                340                 345                 350

Arg Glu Phe Val Ala Ala Ile Ser Trp Ser Gly Gly Ser Thr Tyr Tyr
                355                 360                 365

Ala Asp Ser Val Lys Gly Arg Phe Thr Ile Ser Arg Asp Asn Ser Lys
                370                 375                 380

Asn Thr Val Tyr Leu Gln Met Asn Ser Leu Arg Pro Glu Asp Thr Ala
385                 390                 395                 400

Val Tyr Tyr Cys Ala Ala Ser Pro Ile Pro Tyr Gly Ser Leu Leu Arg
                405                 410                 415

Arg Arg Asn Asn Tyr Asp Tyr Trp Gly Gln Gly Thr Leu Val Thr Val
                420                 425                 430

Ser Ser Gly Ala Ala Glu Gln Lys Leu Ile Ser Glu Glu Asp Leu Asn
                435                 440                 445

Gly Ala Ala His His His His His His
    450                 455
```

<210> SEQ ID NO 47
<211> LENGTH: 462
<212> TYPE: PRT
<213> ORGANISM: Artificial Sequence
<220> FEATURE:
<223> OTHER INFORMATION: VHH construct F013500053

<400> SEQUENCE: 47

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Arg | Thr | Phe | Ser | Ser | Tyr |
| | | | 20 | | | | | 25 | | | | | 30 | | |
| Ala | Met | Gly | Trp | Phe | Arg | Gln | Ala | Pro | Gly | Lys | Glu | Arg | Glu | Phe | Val |
| | | 35 | | | | | 40 | | | | | 45 | | | |
| Ala | Ala | Ile | Ser | Trp | Ser | Gly | Ser | Thr | Tyr | Tyr | Ala | Asp | Ser | Val | |
| | 50 | | | | | 55 | | | | | 60 | | | | |
| Lys | Gly | Arg | Phe | Thr | Ile | Ser | Arg | Asp | Asn | Ser | Lys | Asn | Thr | Val | Tyr |
| 65 | | | | | 70 | | | | | 75 | | | | | 80 |
| Leu | Gln | Met | Asn | Ser | Leu | Arg | Pro | Glu | Asp | Thr | Ala | Val | Tyr | Tyr | Cys |
| | | | | 85 | | | | | 90 | | | | | 95 | |
| Ala | Ala | Ser | Pro | Ile | Pro | Tyr | Gly | Ser | Leu | Leu | Arg | Arg | Asn | Asn | |
| | | | 100 | | | | | 105 | | | | | 110 | | |
| Tyr | Asp | Tyr | Trp | Gly | Gln | Gly | Thr | Leu | Val | Thr | Val | Ser | Ser | Gly | Gly |
| | | | 115 | | | | | 120 | | | | | 125 | | |
| Gly | Gly | Ser | Gly | Gly | Gly | Gly | Ser | Gly | Gly | Gly | Ser | Gly | Gly | Gly | |
| | 130 | | | | | 135 | | | | | 140 | | | | |
| Gly | Ser | Gly | Gly | Gly | Gly | Ser | Gly | Gly | Gly | Ser | Gly | Gly | Gly | Gly | |
| 145 | | | | | 150 | | | | | 155 | | | | | 160 |
| Ser | Glu | Val | Gln | Leu | Val | Glu | Ser | Gly | Gly | Leu | Val | Gln | Pro | Gly | |
| | | | | 165 | | | | | 170 | | | | | 175 | |
| Asn | Ser | Leu | Arg | Leu | Ser | Cys | Ala | Ala | Ser | Gly | Phe | Thr | Phe | Ser | Ser |
| | | | 180 | | | | | 185 | | | | | 190 | | |
| Phe | Gly | Met | Ser | Trp | Val | Arg | Gln | Ala | Pro | Gly | Lys | Gly | Leu | Glu | Trp |
| | | 195 | | | | | 200 | | | | | 205 | | | |
| Val | Ser | Ser | Ile | Ser | Gly | Ser | Gly | Ser | Asp | Thr | Leu | Tyr | Ala | Asp | Ser |
| | 210 | | | | | 215 | | | | | 220 | | | | |
| Val | Lys | Gly | Arg | Phe | Thr | Ile | Ser | Arg | Asp | Asn | Ala | Lys | Thr | Thr | Leu |
| 225 | | | | | 230 | | | | | 235 | | | | | 240 |
| Tyr | Leu | Gln | Met | Asn | Ser | Leu | Arg | Pro | Glu | Asp | Thr | Ala | Val | Tyr | Tyr |
| | | | | 245 | | | | | 250 | | | | | 255 | |
| Cys | Thr | Ile | Gly | Gly | Ser | Leu | Ser | Arg | Ser | Ser | Gln | Gly | Thr | Leu | Val |
| | | | 260 | | | | | 265 | | | | | 270 | | |
| Thr | Val | Ser | Ser | Gly | Gly | Gly | Gly | Ser | Gly | Gly | Gly | Ser | Gly | Gly | |
| | | 275 | | | | | 280 | | | | | 285 | | | |
| Gly | Gly | Ser | Gly | Gly | Gly | Ser | Gly | Gly | Gly | Ser | Gly | Gly | Gly | |
| | 290 | | | | | 295 | | | | | 300 | | | | |
| Gly | Ser | Gly | Gly | Gly | Ser | Glu | Val | Gln | Leu | Val | Glu | Ser | Gly | Gly | |
| 305 | | | | | 310 | | | | | 315 | | | | | 320 |
| Gly | Leu | Val | Gln | Pro | Gly | Gly | Ser | Leu | Arg | Leu | Ser | Cys | Ala | Ala | Ser |
| | | | | 325 | | | | | 330 | | | | | 335 | |
| Gly | Gly | Thr | Phe | Ser | Ser | Tyr | Ala | Met | Gly | Trp | Phe | Arg | Gln | Ala | Pro |
| | | | 340 | | | | | 345 | | | | | 350 | | |
| Gly | Lys | Glu | Arg | Glu | Phe | Val | Ala | Ala | Ile | Arg | Arg | Ser | Gly | Arg | Arg |
| | | 355 | | | | | 360 | | | | | 365 | | | |
| Thr | Tyr | Tyr | Ala | Asp | Ser | Val | Lys | Gly | Arg | Phe | Thr | Ile | Ser | Arg | Asp |
| | 370 | | | | | 375 | | | | | 380 | | | | |
| Asn | Ser | Lys | Asn | Thr | Val | Tyr | Leu | Gln | Met | Asn | Ser | Leu | Arg | Pro | Glu |
| 385 | | | | | 390 | | | | | 395 | | | | | 400 |
| Asp | Thr | Ala | Val | Tyr | Tyr | Cys | Ala | Ala | Ala | Arg | Arg | Val | Arg | Ser | Ser |

```
                    405                 410                 415
Thr Arg Tyr Asn Thr Gly Thr Trp Trp Trp Glu Tyr Trp Gly Gln Gly
                420                 425                 430

Thr Leu Val Thr Val Ser Ser Gly Ala Ala Glu Gln Lys Leu Ile Ser
            435                 440                 445

Glu Glu Asp Leu Asn Gly Ala Ala His His His His His His
    450                 455                 460
```

<210> SEQ ID NO 48

<400> SEQUENCE: 48

000

<210> SEQ ID NO 49

<400> SEQUENCE: 49

000

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Gly Gly Gly Gly Ser Gly Gly Gly Gly Ser Gly Gly Gly Gly Ser
1               5                   10                  15
```

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 52
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 53
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Ser Gly Gly Gly Ser Gly Gly Gly Ser
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Ser Gly Gly Gly Ser Gly Gly Gly Ser Gly Gly Gly Ser
1               5                   10                  15

Gly Gly Gly Ser
            20

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser
            20                  25

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Gly Ser Ser Gly Gly Gly Ser Ser Gly Gly Gly Ser Ser
1               5                   10                  15

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Ser Ser Gly Gly Gly Ser Ser Gly Gly Gly Ser Ser Gly
1               5                   10                  15

Gly Gly Ser Ser Gly Gly Gly Ser Ser
            20                  25

<210> SEQ ID NO 58
<211> LENGTH: 35
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Gly Gly Ser Ser Gly Gly Gly Ser Ser Gly Gly Gly Ser Ser Gly
1               5                   10                  15

Gly Gly Ser Ser Gly Gly Gly Ser Ser Gly Gly Gly Ser Ser Gly Gly
            20                  25                  30

Gly Ser Ser
        35

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His His His His His His
1               5
```